United States Patent
Satoskar et al.

(10) Patent No.: US 10,174,072 B2
(45) Date of Patent: Jan. 8, 2019

(54) ANTILEISHMANIAL COMPOSITIONS AND METHODS OF USE

(71) Applicant: Ohio State Innovation Foundation, Columbus, OH (US)

(72) Inventors: Abhay R. Satoskar, Upper Arlington, OH (US); James F. Fuchs, Columbus, OH (US); Alan Douglas Kinghorn, Columbus, OH (US); Li Pan, Upper Arlington, OH (US); Claudio M. Lezama-Davila, Columbus, OH (US); Eric Bachelder, Dublin, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 15/411,249

(22) Filed: Jan. 20, 2017

(65) Prior Publication Data

US 2017/0305959 A1 Oct. 26, 2017

Related U.S. Application Data

(63) Continuation of application No. 14/300,191, filed on Jun. 9, 2014, now abandoned, which is a continuation of application No. 14/113,379, filed as application No. PCT/US2012/034604 on Apr. 22, 2012, now abandoned.

(60) Provisional application No. 61/478,481, filed on Apr. 22, 2011.

(51) Int. Cl.
| | |
|---|---|
| *C07J 9/00* | (2006.01) |
| *A61K 9/00* | (2006.01) |
| *A61K 47/34* | (2017.01) |
| *A61K 9/10* | (2006.01) |
| *A61K 9/107* | (2006.01) |
| *A61K 47/40* | (2006.01) |
| *A61K 47/44* | (2017.01) |
| *A61K 9/127* | (2006.01) |
| *A61K 9/16* | (2006.01) |
| *A61K 9/20* | (2006.01) |
| *A61K 9/51* | (2006.01) |
| *A61K 31/57* | (2006.01) |
| *A61K 31/575* | (2006.01) |
| *A61K 45/06* | (2006.01) |
| *C07J 7/00* | (2006.01) |

(52) U.S. Cl.
CPC .............. *C07J 9/00* (2013.01); *A61K 9/0019* (2013.01); *A61K 9/10* (2013.01); *A61K 9/1075* (2013.01); *A61K 9/1271* (2013.01); *A61K 9/1273* (2013.01); *A61K 9/1647* (2013.01); *A61K 9/2018* (2013.01); *A61K 9/2054* (2013.01); *A61K 9/2059* (2013.01); *A61K 9/5153* (2013.01); *A61K 31/57* (2013.01); *A61K 31/575* (2013.01); *A61K 45/06* (2013.01); *A61K 47/34* (2013.01); *A61K 47/40* (2013.01); *A61K 47/44* (2013.01); *C07J 7/002* (2013.01); *Y02A 50/409* (2018.01); *Y02A 50/411* (2018.01); *Y02A 50/414* (2018.01); *Y02A 50/415* (2018.01); *Y02A 50/492* (2018.01)

(58) Field of Classification Search
None
See application file for complete search history.

(56) References Cited

U.S. PATENT DOCUMENTS

| | | | |
|---|---|---|---|
| 4,766,046 A | 8/1988 | Abra et al. | |
| 2009/0326069 A1 | 12/2009 | Streeper et al. | |
| 2010/0222425 A1* | 9/2010 | Frincke | ............... A61K 31/343 514/468 |

OTHER PUBLICATIONS

Santalova et al., "Ketosteroids From the Far-East Marine Prosobranch Mollusk Onchidiopsis variegate" Chemistry of Natural Compounds, Jan. 2007, vol. 43, Issue 1, pp. 86-89.*
Ahmed, S. Ansar, Robert M. Gogal, and Jane E. Walsh. "A new rapid and simple non-radioactive assay to monitor and determine the proliferation of lymphocytes: an alternative to [3H] thymidine incorporation assay." Journal of immunological methods 170.2 (1994): 211-224.
Bazin, Marc-Antoine, et al. "Synthesis of oxysterols and nitrogenous sterols with antileishmanial and trypanocidal activities." European journal of medicinal chemistry 41.10 (2006): 1109-1116.
Cabrera, Gabriela, et al. "Steroidal derivatives from the roots of Mandevilla pentlandiana." Phytochemistry 30.4 (1991): 1239-1243.
Centers for Disease Control and Prevention (CDC). Parasites—Leishmaniasis. (2010) www.cdc.gov/parasites/leishmaniasis/disease. html, retrieved Jun. 23, 2016, 2 pages.
Chan-Bacab, Manuel Jesus, et al. "Variation of leishmanicidal activity in four populations of Urechites andrieuxii." Journal of ethnopharmacology 86.2 (2003): 243-247.
Conteh, Lesong, Thomas Engels, and David H. Molyneux. "Socio-economic aspects of neglected tropical diseases." The Lancet 375. 9710 (2010): 239-247.
de Souza, Wanderley, and Juliany Cola Fernandes Rodrigues. "Sterol biosynthesis pathway as target for anti-trypanosomatid drugs." Interdisciplinary perspectives on infectious diseases vol. 2009, article ID 642502 (2009), 19 pages.
Delgado, Gabriela, et al. "Flow cytometry, a useful tool for detecting the lethal effect of pentamidine on Leishmania viannia complex promastigote forms." Pharmacological research 44.4 (2001): 281-286.
Gupta, Vikas, and Payal Mittal. "Phytochemical and pharmacological potential of Nerium oleander: a review." Int J Pharm Sci Res 1.3 (2010): 21-27.

(Continued)

*Primary Examiner* — Svetlana M Ivanova
(74) *Attorney, Agent, or Firm* — Meunier Carlin & Curfman LLC

(57) ABSTRACT

In one aspect, the invention relates methods and compositions for treating parasitic diseases, for example, leishmaniasis. In a further aspect, the compounds of the methods and compositions are isolated from *Pentalinon andrieuxii*. This abstract is intended as a scanning tool for purposes of searching in the particular art and is not intended to be limiting of the present invention.

16 Claims, 12 Drawing Sheets

(56) References Cited

OTHER PUBLICATIONS

Haughan, P. A., M. L. Chance, and L. J. Goad. "Effects of an azasterol inhibitor of sterol 24-transmethylation on sterol biosynthesis and growth of Leishmania donovani promastigotes." Biochemical Journal 308.1 (1995): 31-38.

Hotez, Peter J., et al. "Rescuing the bottom billion through control of neglected tropical diseases." The Lancet 373.9674 (2009): 1570-1575.

Hotez, Peter J., et al. "Control of neglected tropical diseases." New England Journal of Medicine 357.10 (2007): 1018-1027.

Jiu, James. "A survey of some medicinal plants of Mexico for selected biological activities." Lloydia 29 (1966): 250-9.

International Search Report and Written Opinion dated Jul. 27, 2012, by the International Searching Authority for Application No. PCT/US2012/034604, 7 pages.

Magaraci, Filippo, et al. "Azasterols as Inhibitors of Sterol 24-Methyltransferase in Leishmania Species and Trypanosoma c ruzi." Journal of medicinal chemistry 46.22 (2003): 4714-4727.

Murray, Henry W. "Mononuclear cell recruitment, granuloma assembly, and response to treatment in experimental visceral leishmaniasis: intracellular adhesion molecule 1-dependent and-independent regulation." Infection and immunity 68.11 (2000): 6294-6299.

Rosas, Lucia E., et al. "Interleukin-27R (WSX-1/T-cell cytokine receptor) gene-deficient mice display enhanced resistance to leishmania donovani infection but develop severe liver immunopathology." The American journal of pathology 168.1 (2006): 158-169.

PubChem Open Chemistry Database, U.S. National Library of Medicine and National Center for Biotechnology Information. "Neridienone A." Compound Summary for CID 100630, create date: Mar. 26, 2005, retrieved from https://pubchem.ncbi.nlm.nih.gov/compound/Neridienone_A on Jun. 23, 2016, 14 pages.

PubMed Health; Diseases and Conditions. Leishmaniasis. (2009) www.ncbi.nlm.nih.gov/pubmedhealth/PMH0002362.

Santalova, E. A., et al. "Ketosteroids from the far-east marine prosobranch mollusk Onchidiopsis variegata." Chemistry of Natural Compounds 43.1 (2007): 86-89.

Sartorelli, Patricia, et al. "Isolation of antileishmanial sterol from the fruits of Cassia fistula using bioguided fractionation." Phytotherapy Research 21.7 (2007): 644-647.

Toreele, E., Martine Usdin, and Pierre Chirac. "A needs-based pharmaceutical R&D agenda for neglected diseases." World Health Organization (2004): 12, 58 pages.

Trouiller, Patrice, et al. "Drug development for neglected diseases: a deficient market and a public-health policy failure," The Lancet 359.9324 (2002): 2188-2194.

Pan et al., Sterols with antilesishmanial activity isolated from the roots of Pentalinon andrieuxii, Phytochemistry, vol. 82, pp. 128-135, (2012).

Yam-Puc, Alejandro, et al. "Trinorsesquiterpenoids from the Root Extract of Pentalinon andrieuxii." Journal of natural products 72.4 (2009): 745-748.

Werbovetz, Karl A. "Promising therapeutic targets for antileishmanial drugs." Expert opinion on therapeutic targets 6.4 (2002): 407-422.

* cited by examiner

Electron microscopy of promastigotes
Untreated (A; sham control) or treated with
Sodium stibogluconate (B; reference drug),
Compound 1 (C). "FP" : flagellar pocket;
"N" : nucleus; "L" – lipid droplet.
Scale bar = 1000 nm (A) and 500 nm (B, C)

ANTILEISHMANIAL COMPOSITIONS AND METHODS OF USE

CROSS-REFERENCE TO RELATED APPLICATIONS

This application is a continuation of U.S. Utility application Ser. No. 14/300,191, filed Jun. 9, 2014, which is a continuation of U.S. Utility application Ser. No. 14/113,379, filed Apr. 22, 2012, which claims the benefit of U.S. Provisional Application No. 61/478,481, filed Apr. 22, 2011, which are incorporated herein by reference in entirety.

STATEMENT REGARDING FEDERALLY SPONSORED RESEARCH

This invention was made with government support under R21 AI076309, R21 AT004160, and AI090803 awarded by the National Institutes of Health. The government has certain rights in the invention.

BACKGROUND

Leishmaniasis is a protozoan vector borne parasitic disease caused by protozoan parasites of the genus *Leishmania* and is transmitted through the bite of certain species of *Phlembotominae* sandfly. Of the approximately 30 species of *Leishmania* known to infect mammals, 21 of these species are believed to cause leishmaniasis in humans. Leishmaniasis has been reported on all continents except Australia and *Antarctica*, and has been found in parts of about 88 countries. Leishmaniasis is primarily a disease of the developing countries, and is more rare in the developed world. However, cases have been reported in military personnel who have served in the Persian Gulf. In the Americas, leishmaniasis can be found in Mexico and South America, but has recently been shown to be spreading to Texas.

Leishmaniasis manifests in three distinct forms including; cutaneous leishmaniasis (CL), visceral leishmaniasis (VL) and mucocutaneous leishmaniasis (ML). Of the three variants recognized by the Centers for Disease Control and Prevention (CDC), CL and VL are considered endemic diseases in tropical and subtropical regions throughout the world. Leishmaniasis threatens approximately 350 million humans in nearly 90 countries. Currently, approximately 12 million humans are believed to be infected, with over 2 million new cases being reported each year. Leishmaniasis disproportionally affects the poorest inhabitants of the world and significantly hinders the economic development of these developing societies.

Due to the complex life cycles of the causative parasites, leishmaniasis is rarely diagnosed in its early stages when therapeutic intervention is most effective. Leishmaniasis typically presents as skin sores or ulcers which erupt weeks to months after the person is bitten. However, if left untreated, the infection can progress and lead to splenomegaly, liver damage, renal damage, anemia, and death.

Therapeutic compounds containing antimony, specifically pentavalent antimonials (e.g., meglumine antimonate and sodium stibogluconate) were the first drugs introduced to treat leishmaniasis, and they remain the first-line therapeutic approach in many parts of the world. However, use of pentavalent antimonials is associated with significant adverse effects and are administered by intravenous or intramuscular injection. Moreover, the use of these drugs as first-line therapy for over 50 years has resulted in the emergence of drug-resistant parasites.

Unfortunately, despite the significant prevalence of this disease throughout large portions of the world, there remains a scarcity of therapeutic agents that have potent activity against *Leishmania* species with minimal adverse effect on the patient and an efficient route of administration. Therefore, there remains a need for methods and compositions that overcome these deficiencies and that provide a therapeutic alternative for leishmaniasis.

SUMMARY

In one aspect, the invention relates to sterol compounds useful as therapeutic agents for the treatment of leishmaniasis and related diseases including, but not limited to malaria, human African trypanomiasis, babesiosis, Chagas disease, microsporidiosis, pneumocystosis, primary amcobic meningoenchephalitis, and toxoplasmosis.

Disclosed are methods of treatment of a parasitic disease in a mammal diagnosed with the disease, the method comprising the step of administering to the mammal a therapeutically effective amount of at least one compound having a structure represented by a formula:

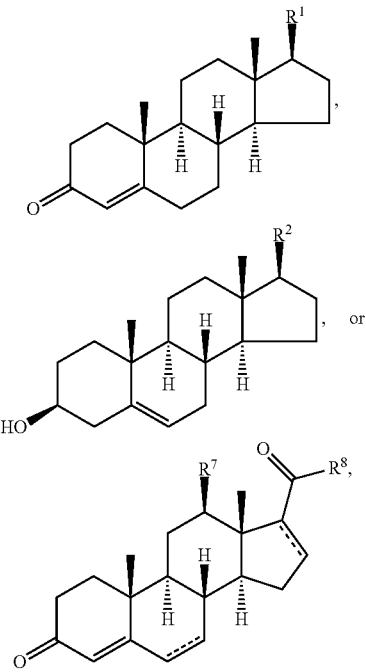

wherein each ---- is independently an optional covalent bond, wherein valence is satisfied; wherein $R^1$, when present, is selected from C1-C12 alkyl and C1-C12 alkenyl; wherein $R^2$, when present, is selected from C1-C12 alkyl and C1-C12 alkenyl; wherein $R^7$ is selected from hydrogen, hydroxyl, amino, and halogen; and wherein $R^8$ is selected from hydrogen and C1-C6 alkyl; or a pharmaceutically acceptable salt, solvate, or polymorph thereof.

Also disclosed are methods for the treatment of a parasitic disease comprising the steps of: a) identifying a mammal in need of treatment of a parasitic disease; and b) administering to the mammal an effective amount of at least one compound having a structure represented by a formula:

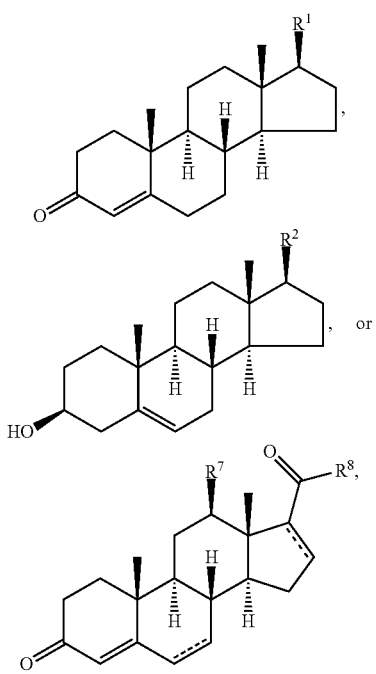

wherein each ---- is independently an optional covalent bond, wherein valence is satisfied; wherein $R^1$, when present, is selected from C1-C12 alkyl and C1-C12 alkenyl; wherein $R^2$, when present, is selected from C1-C12 alkyl and C1-C12 alkenyl; wherein $R^7$ is selected from hydrogen, hydroxyl, amino, and halogen; and wherein $R^8$ is selected from hydrogen and C1-C6 alkyl; or a pharmaceutically acceptable salt, solvate, or polymorph thereof.

Also disclosed are method for treating a parasitic disease, the method comprising the step of contacting a mammalian cell with an effective amount of at least one compound having a structure represented by a formula:

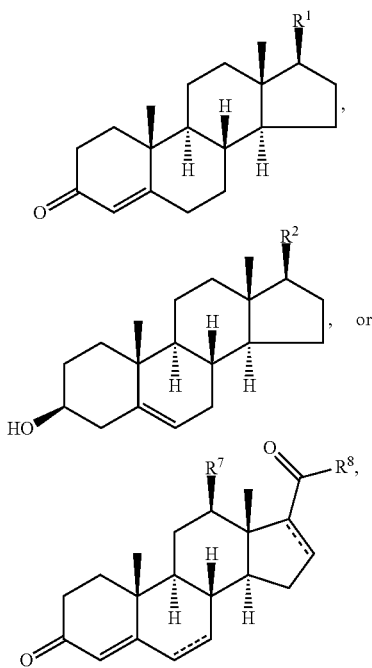

wherein each ---- is independently an optional covalent bond, wherein valence is satisfied; wherein $R^1$, when present, is selected from C1-C12 alkyl and C1-C12 alkenyl; wherein $R^2$, when present, is selected from C1-C12 alkyl and C1-C12 alkenyl; wherein $R^7$ is selected from hydrogen, hydroxyl, amino, and halogen; and wherein $R^8$ is selected from hydrogen and C1-C6 alkyl; or a pharmaceutically acceptable salt, solvate, or polymorph thereof.

Also disclosed are pharmaceutical compositions comprising a pharmaceutically acceptable carrier and an effective amount of a compound represented by a formula:

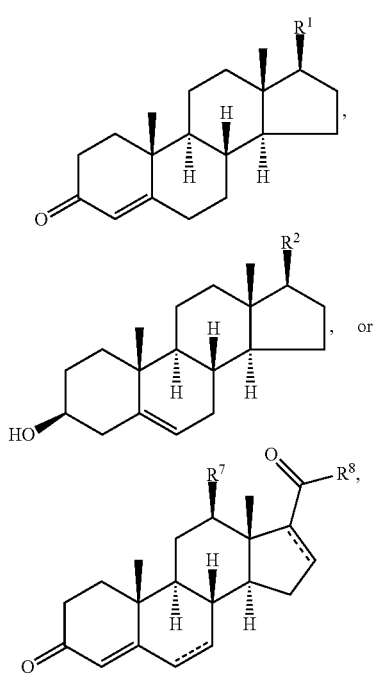

wherein each ---- is independently an optional covalent bond, wherein valence is satisfied; wherein $R^1$, when present, is selected from C1-C12 alkyl and C1-C12 alkenyl; wherein $R^2$, when present, is selected from C1-C12 alkyl and C1-C12 alkenyl; wherein $R^7$ is selected from hydrogen, hydroxyl, amino, and halogen; and wherein $R^8$ is selected from hydrogen and C1-C6 alkyl; or a pharmaceutically acceptable salt, solvate, or polymorph thereof.

Also disclosed are kits comprising at least one compound represented by a formula:

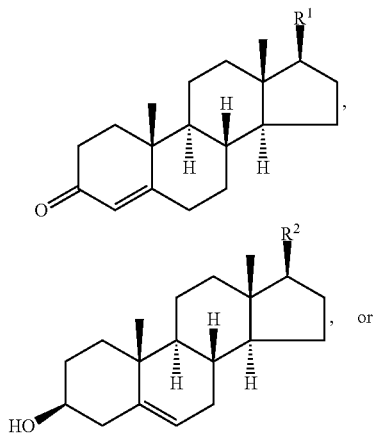

-continued

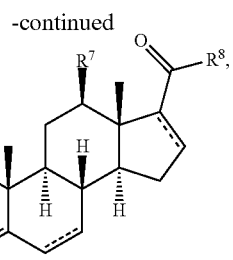

wherein each ---- is independently an optional covalent bond, wherein valence is satisfied; wherein $R^1$, when present, is selected from C1-C12 alkyl and C1-C12 alkenyl; wherein $R^2$, when present, is selected from C1-C12 alkyl and C1-C12 alkenyl; wherein $R^7$ is selected from hydrogen, hydroxyl, amino, and halogen; and wherein $R^8$ is selected from hydrogen and C1-C6 alkyl; or a pharmaceutically acceptable salt, solvate, or polymorph thereof, and one or more of: a) at least one agent known to increase the likelihood of a parasitic disease in a mammal; b) at least one agent known to decrease the likelihood of a parasitic disease in a mammal; c) at least one agent know to treat a parasitic disease in a mammal; or d) instructions for treating a parasitic disease.

Additionally, the invention also relates to a product comprising a disclosed compound as described herein and an additional pharmaceutical agent, as a combined preparation for simultaneous, separate or sequential use in the treatment or prevention of leishmaniasis and related diseases including, but not limited to malaria, human African trypanomiasis, babesiosis, Chagas disease, microsporidiosis, pneumocystosis, primary amoebic meningoenchephalitis, and toxoplasmosis.

Also disclosed are methods for manufacturing a medicament comprising combining at least one disclosed compound, or pharmaceutically acceptable salt, hydrate, solvate, or polymorph thereof, with a pharmaceutically acceptable carrier or diluent. Additionally, the invention relates to a compound as defined herein, or pharmaceutically acceptable salt, hydrate, solvate, or polymorph thereof, for use as a medicament, and to a compound as defined herein for use in the treatment or in the prevention of leishmaniasis and related diseases including, but not limited to malaria, human African trypanomiasis, babesiosis, Chagas disease, microsporidiosis, pneumocystosis, primary amoebic meningoenchephalitis, and toxoplasmosis.

Also disclosed are uses of a disclosed compound, or pharmaceutically acceptable salt, solvate, or polymorph thereof, in the manufacture of a medicament for the treatment of leishmaniasis and related diseases including, but not limited to malaria, human African trypanomiasis, babesiosis, Chagas disease, microsporidiosis, pneumocystosis, primary amoebic meningoenchephalitis, and toxoplasmosis.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
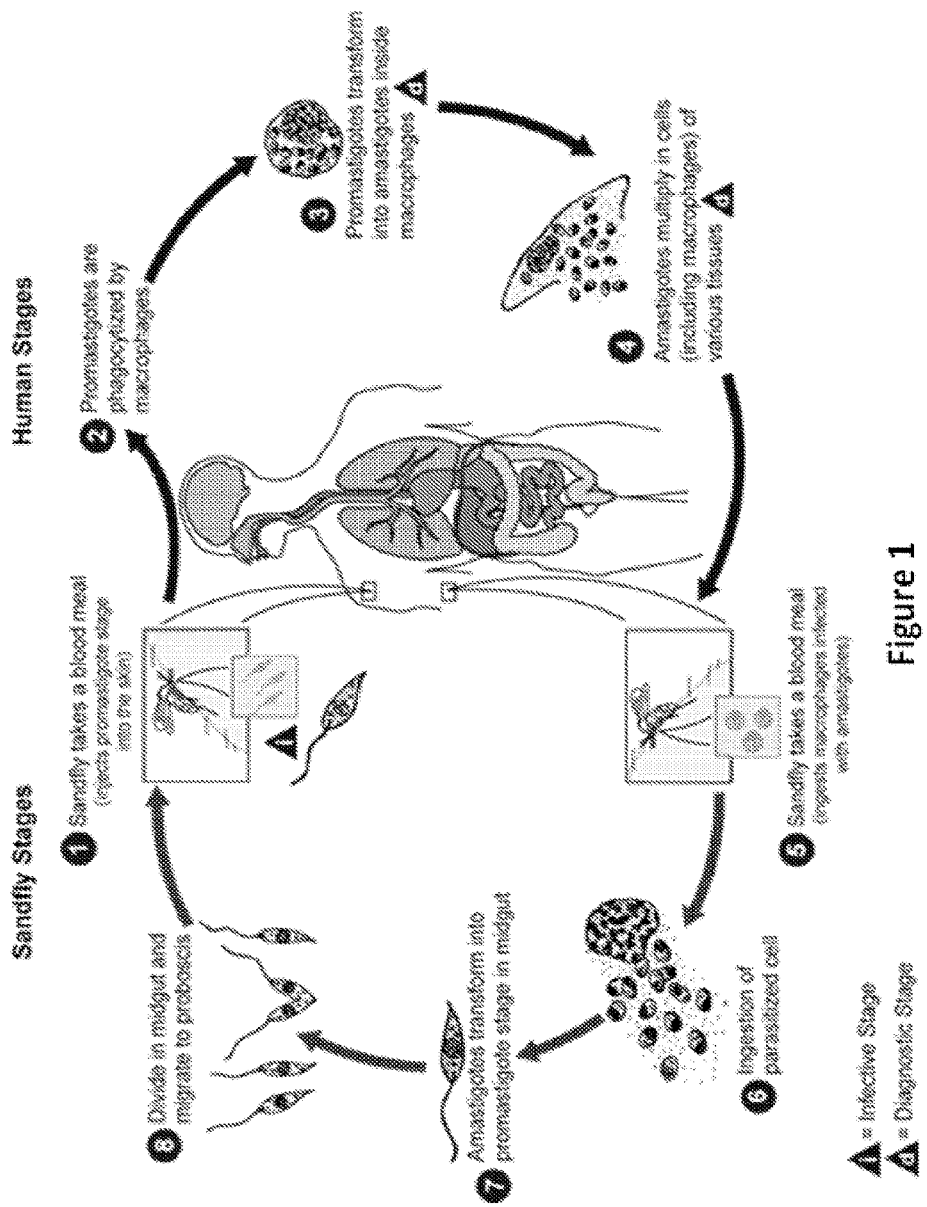
FIG. 1 shows a schematic illustrating the life cycle of *Leishmania*.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. DEFINITIONS

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the term "Leishmaniasis" means a protozoal infection caused by any member of the genus *Leishmania* and characterized by one or any combination of the following symptoms; skin sores, ulcers, fever, infection, damage to the liver, damage to the kidneys, anemia, and enlarged spleen.

As used herein, the terms "protozoa," "protozoan," and "protozoal" can be used interchangeably and mean any member of a diverse group of single-celled eukaryotic organisms which display motile properties.

As used herein, the terms "antileishmanial agent," "antileishmanial compound," and "antileishmanial drug" can be used interchangeably and means any molecule, therapeutic agent, or compound that inhibits, eliminates, and/or reduces the expression of leishmaniasis in infected mammals.

As used herein, the term "inhibit" means disinfect, inhibit, damage, eliminate, reduce, kill, or a combination thereof.

As used herein, the term "sterol" means any molecule from a group of predominately unsaturated solid alcohols of the steroid group, such as cholesterol and ergosterol, present in the fatty tissues of plants and animals.

As used herein, the term "coumarins" means any chemical compound characterized by a benzopyrone skeleton, which are typically found in plants. Coumarins are chemical compounds that typically have pleasantly fragrant aromas and typically serve as appetite suppressants when ingested.

As used herein, the term "triterpenes" means any chemical compound comprising six isoprene units and belonging to the oleanane subfamily.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of leishmaniasis and related diseases including, but not limited to malaria, human African trypanomiasis, babesiosis, Chagas disease, microsporidiosis, pneumocystosis, primary amoebic meningoenchephalitis, and toxoplasmosis, prior to the administering step. In some aspects of the disclosed method, the subject has been diagnosed with a need for inhibiting replication, growth or transmission of a parasite associated with leishmaniasis and related diseases including, but not limited to malaria, human African trypanomiasis, babesiosis, Chagas disease, microsporidiosis, pneumocystosis, primary amoebic meningoenchephalitis, and toxoplasmosis, prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by a disclosed compound" means having been subjected to a physical examination by a person of skill, for example, a physician, and found to have a condition that can be diagnosed or treated by a compound or composition that can inhibit replication, proliferation, growth or transmission of a parasite associated with leishmaniasis and related diseases including, but not limited to malaria, human African trypanomiasis, babesiosis, Chagas disease, microsporidiosis, pneumocystosis, primary amoebic meningoenchephalitis, and toxoplasmosis. As a further example, "diagnosed with a need for inhibition of a parasitic growth" refers to having been subjected to a physical examination by a person of skill, for example, a physician, and found to have a condition characterized by the presence of a parasite. Such a diagnosis can be in reference to a disorder, such as leishmaniasis and related diseases including, but not limited to malaria, human African trypanomiasis, babesiosis, Chagas disease, microsporidiosis, pneumocystosis, primary amoebic meningoenchephalitis, and toxoplasmosis, and the like, as discussed herein.

As used herein, the phrase "identified to be in need of treatment for a disorder," or the like, refers to selection of a subject based upon need for treatment of the disorder. For example, a subject can be identified as having a need for treatment of a disorder (e.g., leishmaniasis and related diseases including, but not limited to malaria, human African trypanomiasis, babesiosis, Chagas disease, microsporidiosis, pneumocystosis, primary amoebic meningoenchephalitis, and toxoplasmosis) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, intradermal administration and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, a target receptor, or other biological entity together in such a manner that the compound can affect the activity of the target (e.g., enzyme, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14 th edition), the Physicians' Desk Reference (64 th edition), and The Pharmacological Basis of Therapeutics (12 th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "$IC_{50}$," is intended to refer to the concentration of a substance (e.g., a compound or a drug) that is required for 50% inhibition of a biological process, or component of a process. For example, $IC_{50}$ refers to the half maximal (50%) inhibitory concentration (IC) of a substance as determined in a suitable assay. For example, an $IC_{50}$ can be determined in an in vitro or cell-based assay system. Frequently, cell-based assays are used to assay efficacy of therapeutic agents directed to leishmaniasis and trypanomiasis, e.g. an assay of promastigote replication or amastigote infection rates of bone marrow-derived macrophages. Alternatively, an $IC_{50}$ value can be determined from an analysis of expression levels of cytokines such as IFN-γ or IL-10 following stimulation of isolated T-cells with *L. donovani* antigen in the presence of varied concentrations of therapeutic agent.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, pegylated derivatives of a parent compound and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters), poly(anhydrides) and polyacetals. Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Alternatively, injectable formulations can be sterilized, for example, by irradiation such as gamma irradiation. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dode cyl, tetradecyl, hexadecyl, eicosyl, tetracosyl, and the like. It is understand that the alkyl group is acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The cycloalkenyl group can be substituted or unsubstituted. The cycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The cycloalkynyl group can be substituted or unsubstituted. The cycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the it clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The terms "halo," "halogen," or "halide," as used herein can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "hydroxyl" or "hydroxy" as used herein is represented by the formula —OH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkyl-carboxamide, dialkylcarboxamide, substituted dialkylcar-boxamide, alkylsulfonyl, alkylsulfinyl, thioalkyl, thioha-loalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound. For example, a compound prefixed with (−) or l meaning that the compound is levorotatory or a compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, sec e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

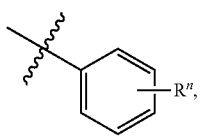

which is understood to be equivalent to a formula:

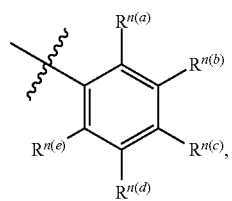

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, the invention relates to compounds useful as therapeutic agents for the treatment of leishmaniasis and related diseases including, but not limited to malaria, human African trypanomiasis, babesiosis, Chagas disease, microsporidiosis, pneumocystosis, primary amoebic meningoenchephalitis, and toxoplasmosis.

In various aspects, the invention pertains to a new cholesterol derivative, pentalinonsterol (1), and a new polyoxygenated pregnane sterol glycoside, pentalinonoside (2), together with 18 known compounds, including 14 sterols (3-16), three coumarins (17-19), and a triterpene (20), were isolated from the roots of Pentalinon andrieuxii. Isolated and purified compounds were evaluated in vitro for their antileishmanial activity. Among these compounds, 6,7-dihydroneridienone (15), a known C-21 sterol, was found to be potent against promastigotes of L. mexicana. The new cholesterol analogue, pentalinonsterol (cholest-4,20,24-trien-3-one, 1), together with other two known sterols, 24-methylcholest-4,24(28)-dien-3-one (3) and neridienone (16), also exhibited significant leishmanicidal activity. The intracellular parasites treated with compounds 1, 3, 4, 15, and 16 were further studied by electron microscopy, and morphological abnormalities and destruction of the amastigotes were observed, as a result of the treatment with these compounds.

1. Structure

In one aspect, the present invention pertains to compounds having a structure represented by a formula:

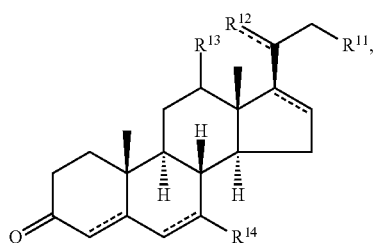

wherein each ---- is independently an optional covalent bond, wherein valence is satisfied; wherein R" is selected from the group consisting of H, alkyl, alkenyl, aryl, and heteroaryl; wherein $R^{12}$ is selected from the group consisting of =CH$_2$, =O, and —CH$_3$; $R^{13}$ is selected from the group consisting of hydrogen, hydroxyl, amino, halogen, and keto; and wherein $R^{14}$ is selected from the group consisting of hydrogen, hydroxyl, amino, halogen, and keto; or a pharmaceutically acceptable salt, solvate, or polymorph thereof.

In a further aspect, the present invention pertains to compound (1):

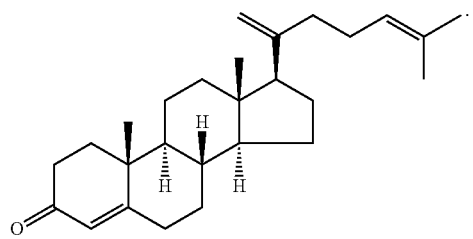

Compound 1 is also referred to herein as pentalinonsterol or alternatively as (3 S,8S,9S,10R,13S,14S,17R)-10,13-dimethyl-17-(6-methylhepta-1,5-dien-2-yl)-2,3,4,7,8,9,10,11,12,13,14,15,16,17-tetradecahydro-1H-cyclopenta[a]phenanthren-3-ol, or a pharmaceutically acceptable salt, solvate, or polymorph thereof.

In one aspect, the present invention pertains to compounds having a structure represented by a formula:

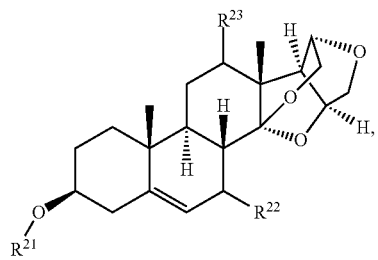

wherein $R^{21}$ is selected from the group consisting of H, alkyl, alkenyl, aryl, heteroaryl, silyl, and sugar; wherein $R^{22}$ is selected from the group consisting of hydrogen, hydroxyl, and keto; and wherein $R^{23}$ is selected from the group consisting of hydrogen, hydroxyl, and keto; or a pharmaceutically acceptable salt, solvate, or polymorph thereof.

In a further aspect, the present invention pertains to compound (2):

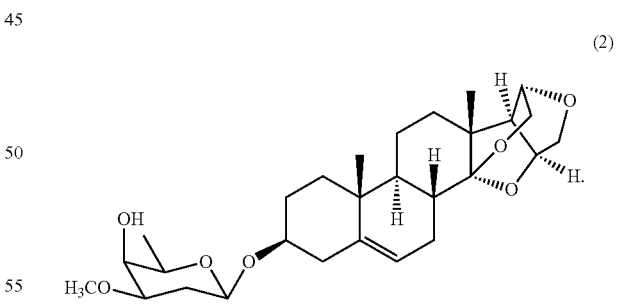

Compound 2 is a new polyoxygenated pregnane sterol glycoside, and is also referred to herein as pentalinonoside or alternatively as (2R,3S,4R,6R)-6-(((1S,3aS,5aR,5bR,9S,11aR,11bS,13aR,13bS)-11a,13a-dimethyl-1,2,3a,4,5b,6,8,9,10,11,11a,11b,12,13,13a,13b-hexadecahydro-1,5a-epoxyfuro[2,3-c]naphtho[1,2-h]chromen-9-yl)oxy)-4-methoxy-2-methyltetrahydro-2H-pyran-3-ol, or a pharmaceutically acceptable salt, solvate, or polymorph thereof In one aspect, the invention relates to a compound having a structure represented by a formula:

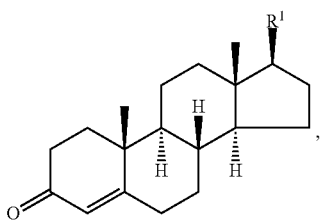

wherein $R^1$ is selected from C1-C12 alkyl and C1-C12 alkenyl; or a pharmaceutically acceptable salt, solvate, or polymorph thereof. In a further aspect, $R^1$ is C1-C12 alkyl. In a still further aspect, $R^1$ is C1-C12 alkenyl. In a yet further aspect, $R^1$ is C8-C12 alkenyl. In a yet further aspect, $R^1$ is C8-C11 alkenyl. In an even further aspect, $R^1$ is C8-C10 alkenyl. In a still further aspect, $R^1$ is C8-C9 alkenyl. In a yet further aspect, $R^1$ is C8 alkenyl. In an even further aspect, $R^1$ is selected from:

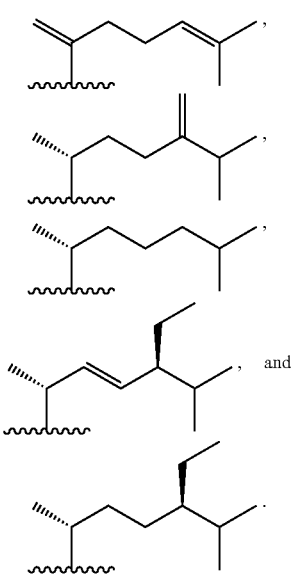

In a still further aspect, $R^1$ is selected from:

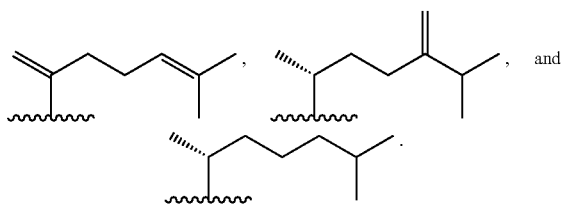

In a further aspect, the invention relates to a compound having a structure represented by a formula:

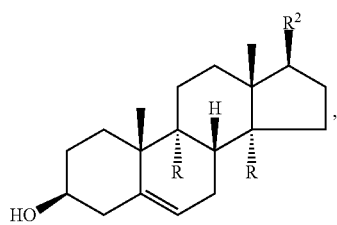

wherein $R^2$ is selected from C1-C12 alkyl and C1-C12 alkenyl; or a pharmaceutically acceptable salt, solvate, or polymorph thereof. In a further aspect, $R^2$ is C1-C12 alkyl. In a still further aspect, $R^2$ is C1-C12 alkenyl. In a yet further aspect, $R^2$ is C8-C12 alkenyl. In a yet further aspect, $R^2$ is C8-C11 alkenyl. In an even further aspect, $R^2$ is C8-C10 alkenyl. In a still further aspect, $R^2$ is C8-C9 alkenyl. In a yet further aspect, $R^2$ is C8 alkenyl. In an even further aspect, $R^2$ is selected from:

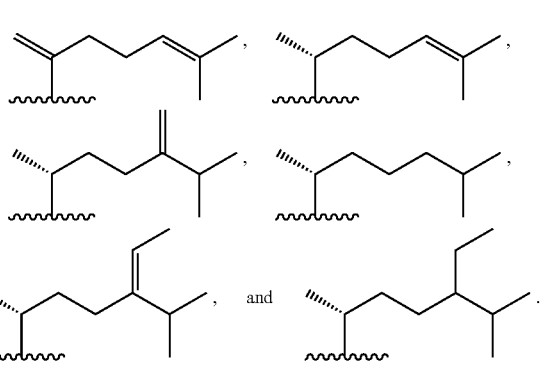

In a still further aspect, $R^2$ is:

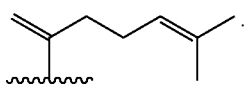 [SMILES: *C(=C)CCC=C(C)C]

In one aspect, the invention relates to a compound having a structure represented by a formula:

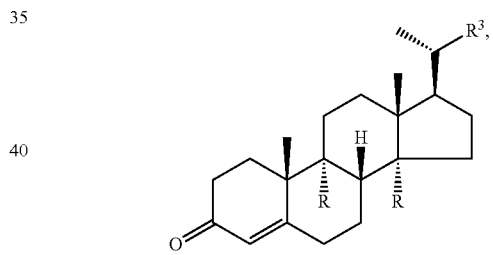

wherein $R^3$ is selected from C1-C8 alkyl and C1-C8 alkenyl; or a pharmaceutically acceptable salt, solvate, or polymorph thereof. In a further aspect, $R^3$ is C1-C8 alkyl. In a still further aspect, $R^3$ is C1-C8 alkenyl. In a yet further aspect, $R^3$ is C4-C8 alkenyl. In a yet further aspect, $R^3$ is C5-C7 alkenyl. In an even further aspect, $R^3$ is C6 alkenyl.

In one aspect, the invention relates to a compound having a structure represented by a formula:

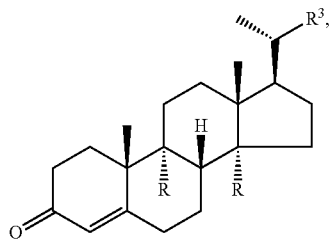

wherein $R^3$ is selected from C1-C12 alkyl and C1-C12 alkenyl; or a pharmaceutically acceptable salt, solvate, or polymorph thereof. In a further aspect, $R^3$ is C1-C8 alkyl. In a still further aspect, $R^3$ is C1-C8 alkenyl. In a yet further aspect, $R^3$ is C4-C8 alkenyl. In a yet further aspect, $R^3$ is C5-C7 alkenyl. In an even further aspect, $R^3$ is C6 alkenyl.

In one aspect, the invention relates to a compound having a structure represented by a formula:

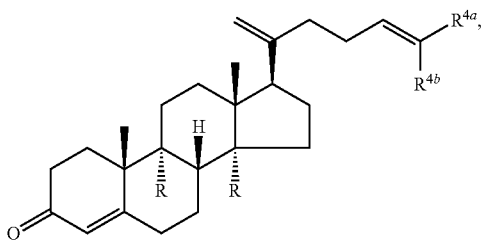

wherein each of $R^{4a}$ and $R^{4b}$ is independently selected from hydrogen and C1-C12 alkyl; or a pharmaceutically acceptable salt, solvate, or polymorph thereof. In a further aspect, each of $R^{4a}$ and $R^{4b}$ is independently selected from hydrogen, methyl, ethyl, propyl, and isopropyl. In a further aspect, each of $R^{4a}$ and $R^{4b}$ is independently selected from hydrogen, methyl, and ethyl. In a yet further aspect, each of $R^{4a}$ and $R^{4b}$ is independently selected from hydrogen and methyl.

In a further aspect, the invention relates to a compound having a structure represented by a formula:

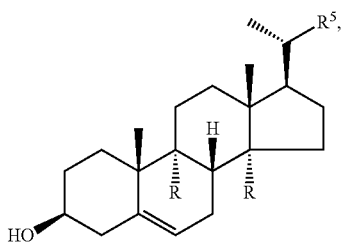

wherein $R^5$ is selected from C1-C8 alkyl and C1-C8 alkenyl; or a pharmaceutically acceptable salt, solvate, or polymorph thereof. In a further aspect, $R^5$ is C1-C8 alkyl. In a still further aspect, $R^5$ is C1-C8 alkenyl. In a yet further aspect, $R^5$ is C4-C8 alkenyl. In a yet further aspect, $R^5$ is C5-C7 alkenyl. In an even further aspect, $R^5$ is C6 alkenyl.

In a further aspect, the invention relates to a compound having a structure represented by a formula:

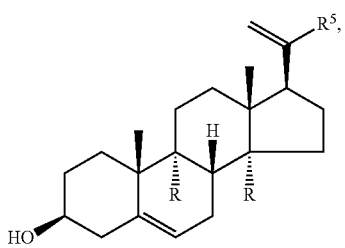

wherein $R^5$ is selected from C1-C8 alkyl and C1-C8 alkenyl; or a pharmaceutically acceptable salt, solvate, or polymorph thereof. In a further aspect, $R^5$ is C1-C8 alkyl. In a still further aspect, $R^5$ is C1-C8 alkenyl. In a yet further aspect, $R^5$ is C4-C8 alkenyl. In a yet further aspect, $R^5$ is C5-C7 alkenyl. In an even further aspect, $R^5$ is C6 alkenyl.

In a further aspect, the invention relates to a compound having a structure represented by a formula:

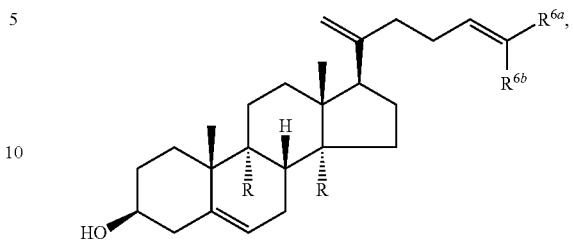

wherein each of $R^{6a}$ and $R^{6b}$ is independently selected from hydrogen and C1-C12 alkyl; or a pharmaceutically acceptable salt, solvate, or polymorph thereof. In a further aspect, each of $R^{6a}$ and $R^{6b}$ is independently selected from hydrogen, methyl, ethyl, propyl, and isopropyl. In a further aspect, each of $R^{6a}$ and $R^{6b}$ is independently selected from hydrogen, methyl, and ethyl. In a yet further aspect, each of $R^{6a}$ and $R^{6b}$ is independently selected from hydrogen and methyl.

In a further aspect, the invention relates to a compound having a structure represented by a formula:

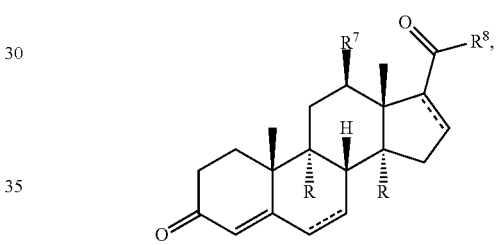

wherein each ---- is independently an optional covalent bond, wherein valence is satisfied; wherein $R^7$ is selected from hydrogen, hydroxyl, amino, and halogen; and wherein $R^8$ is selected from hydrogen and C1-C6 alkyl; or a pharmaceutically acceptable salt, solvate, or polymorph thereof. In a still further aspect, $R^7$ is hydroxyl. In a yet further aspect, $R^8$ is selected from hydrogen, methyl, ethyl, propyl, and isopropyl. In an even further aspect, $R^8$ is methyl. In a still further aspect, $R^7$ is hydroxyl and $R^8$ is methyl.

In a further aspect, the invention relates to a compound having a structure represented by a formula:

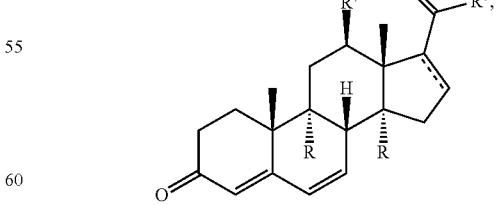

wherein ---- is an optional covalent bond, wherein valence is satisfied; wherein $R^7$ is selected from hydrogen, hydroxyl, amino, and halogen; and wherein $R^8$ is selected from hydrogen and C1-C6 alkyl; or a pharmaceutically acceptable salt, solvate, or polymorph thereof.

In a further aspect, the invention relates to a compound having a structure represented by a formula:

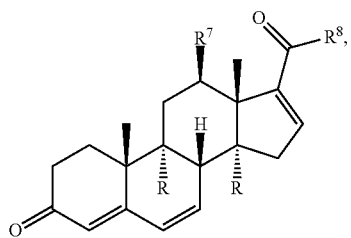

wherein R[7] is selected from hydrogen, hydroxyl, amino, and halogen; and wherein R[8] is selected from hydrogen and C1-C6 alkyl; or a pharmaceutically acceptable salt, solvate, or polymorph thereof.

In a further aspect, the invention relates to a compound having a structure represented by a formula:

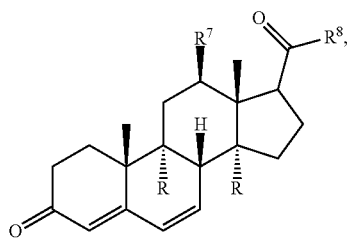

wherein R[7] is selected from hydrogen, hydroxyl, amino, and halogen; and wherein R[8] is selected from hydrogen and C1-C6 alkyl; or a pharmaceutically acceptable salt, solvate, or polymorph thereof.

In a further aspect, the invention relates to a compound having a structure represented by a formula:

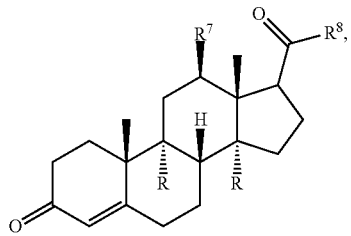

wherein R[7] is selected from hydrogen, hydroxyl, amino, and halogen; and wherein R[8] is selected from hydrogen and C1-C6 alkyl; or a pharmaceutically acceptable salt, solvate, or polymorph thereof.

In various aspects, disclosed herein is the isolation and structure elucidation of new sterols 1 and 2, as well as the in vitro leishmanicidal activity of all isolates obtained when evaluated against promastigotes and amastigotes of *L. mexicana*.

In a further aspect, disclosed herein is a new cholesterol derivative, pentalinonsterol (1), and a new polyoxygenated pregnane sterol glycoside, pentalinonoside [(2), FIG. 1].

Figure 3:
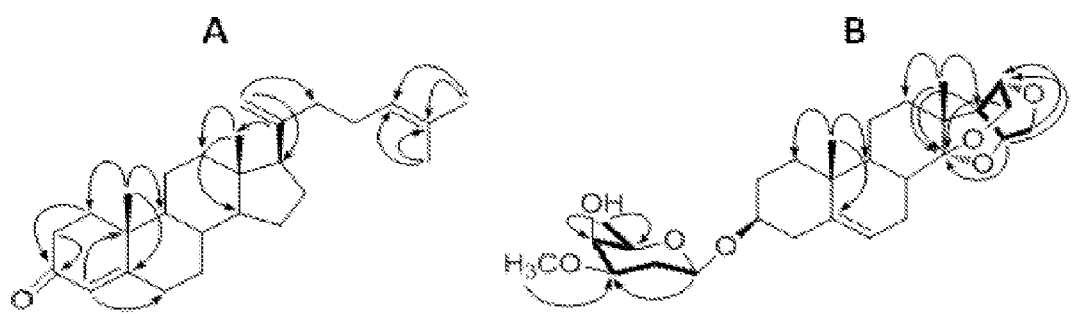
FIG. 3 shows $^1$H-$^1$H COSY (—) and HMBC (→) correlations observed for compounds 1 and 2.
Figure 4:
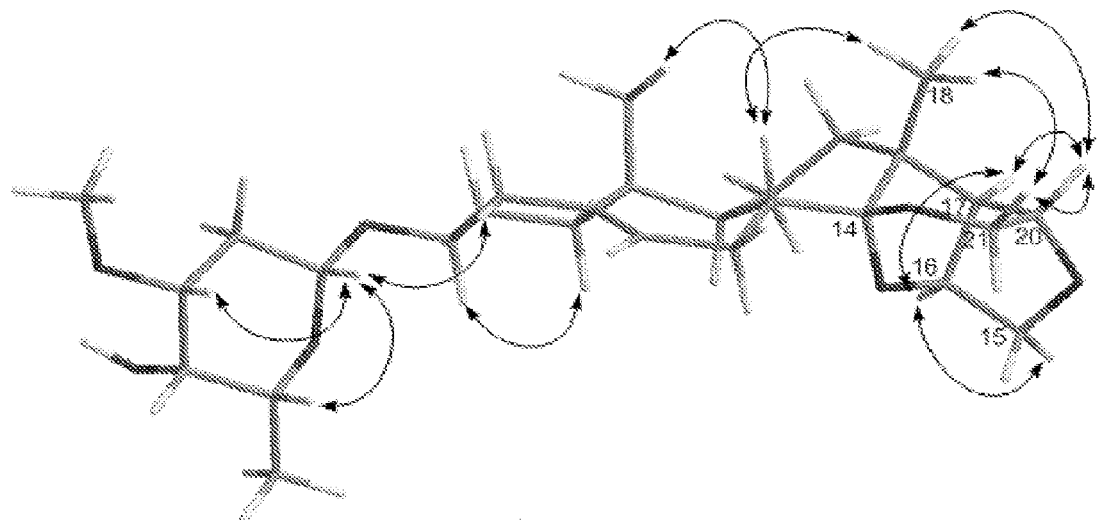
FIG. 4 shows conformation and selected NOESY (↔) correlations observed for compound 2.

In a further aspect, disclosed herein is the spectroscopic characterization (FIGS. 3 and 4; Table 4) and biological evaluation of 1-20 (Table 5) in an in vitro model of *Leishmania mexicana* for leishmaniasis.

2. Example Compounds

In one aspect, a compound can be present as:

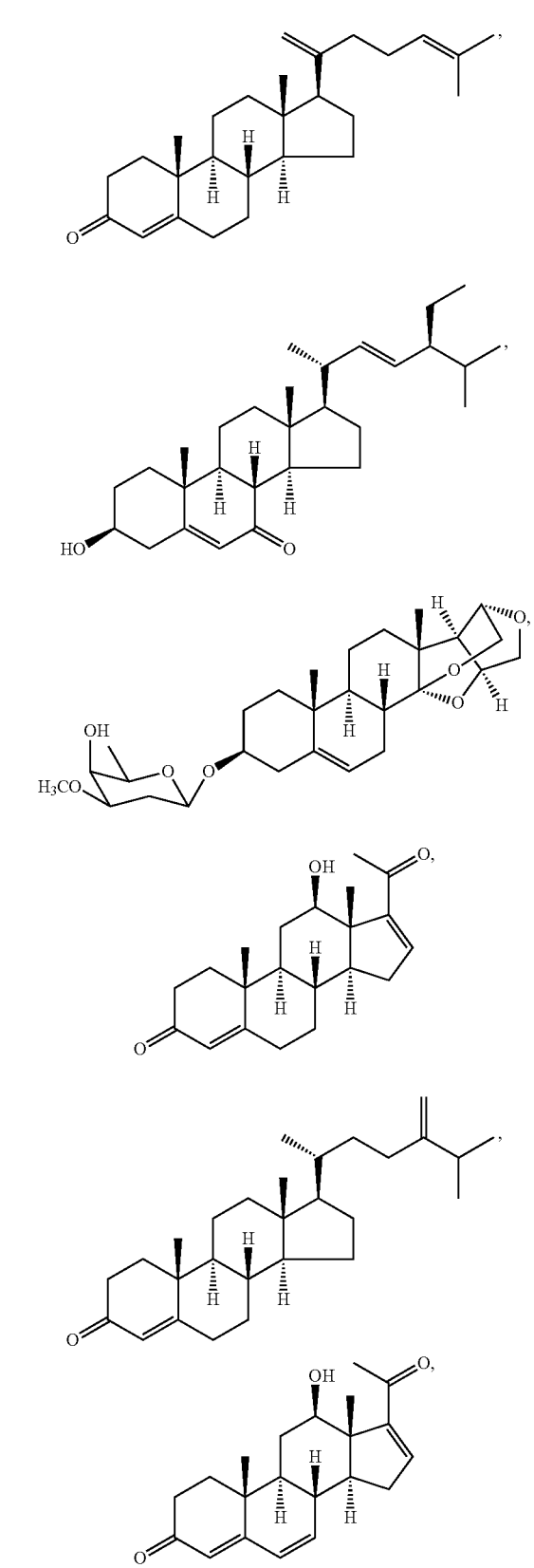

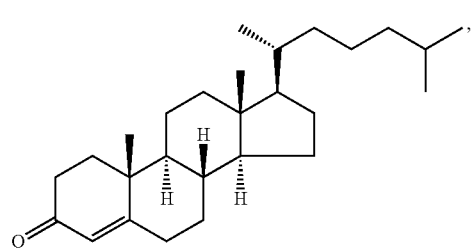
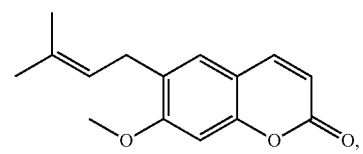
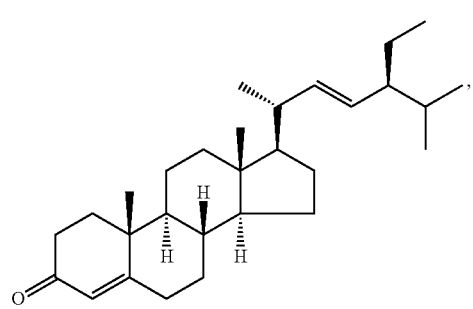
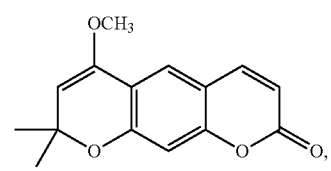
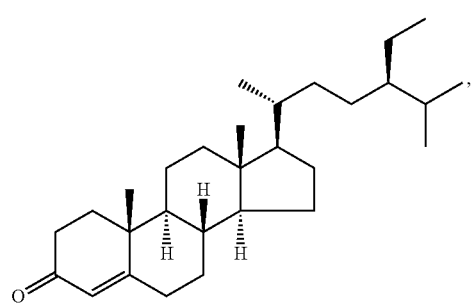
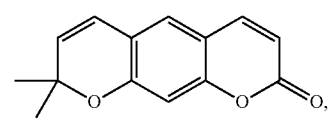
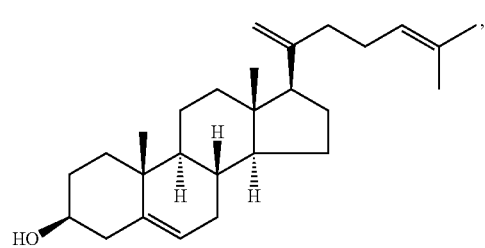
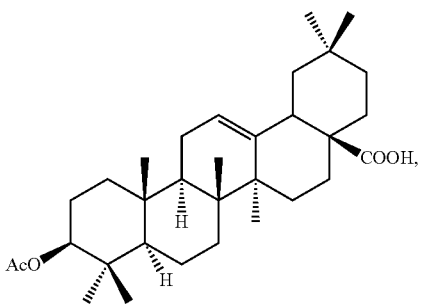
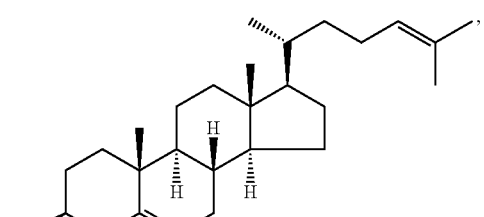
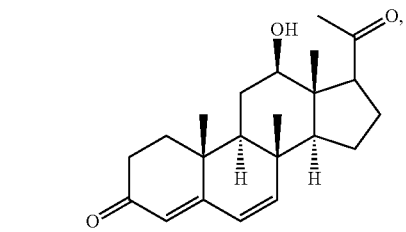
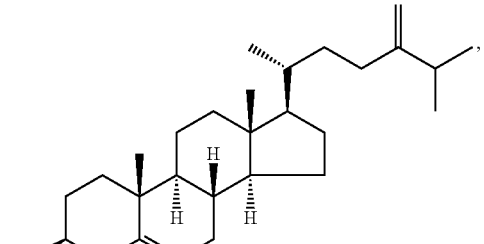
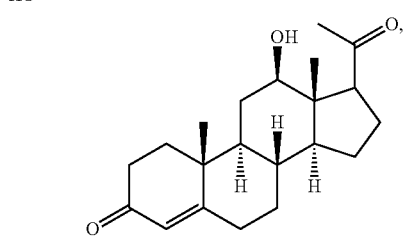
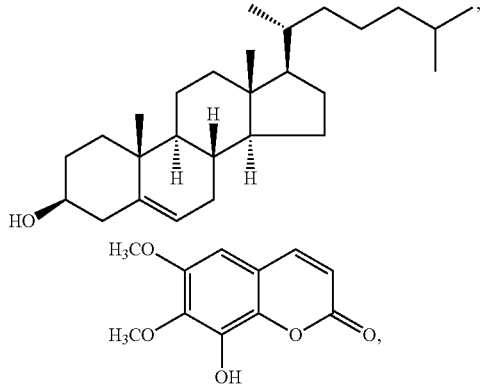

31
-continued
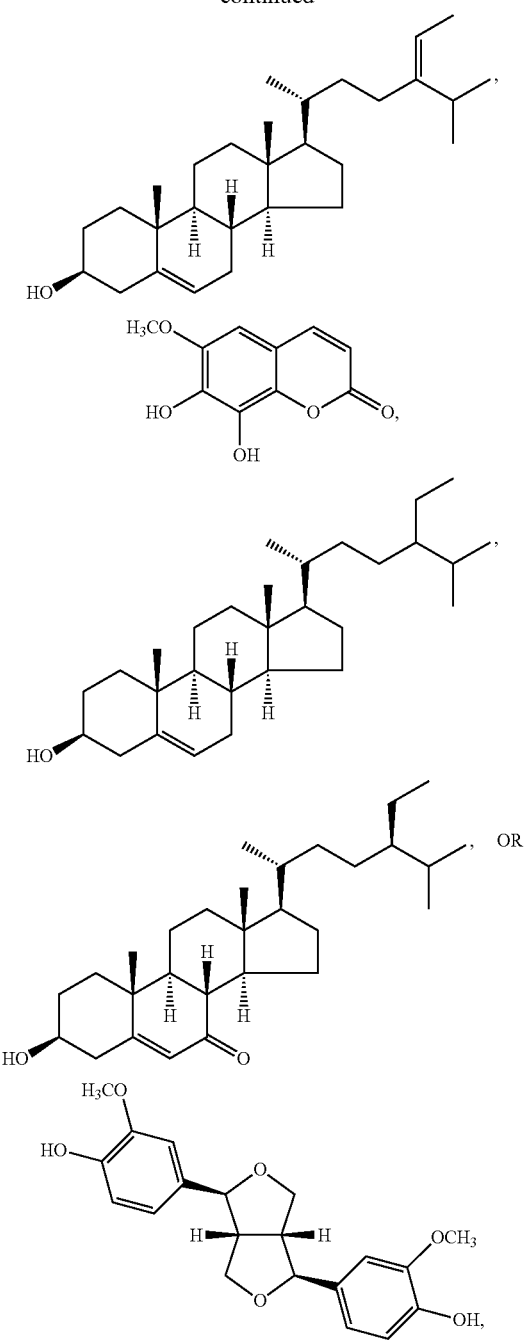
or a subgroup thereof.
In one aspect, a compound can be present as:
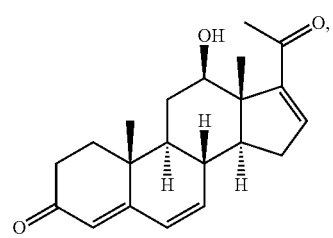
32
-continued
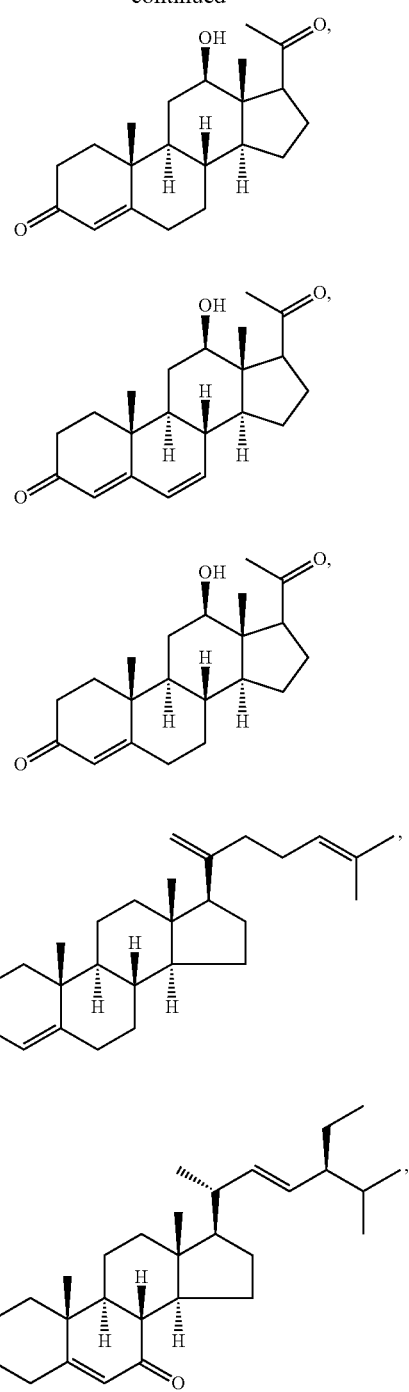
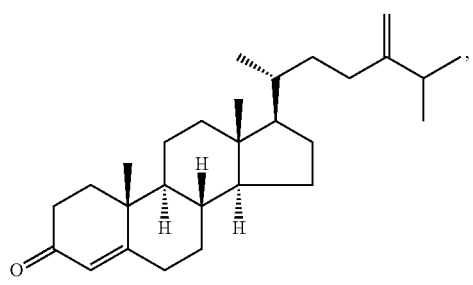

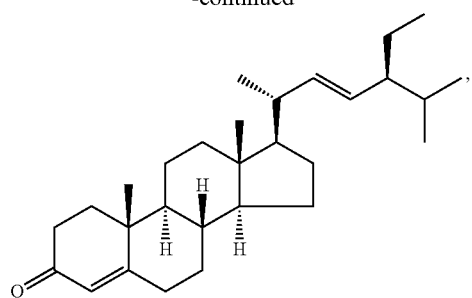
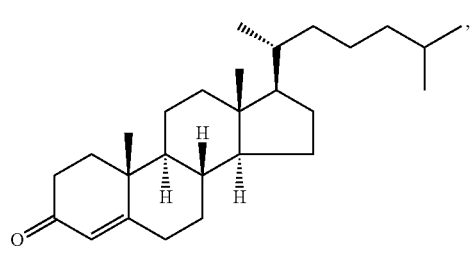
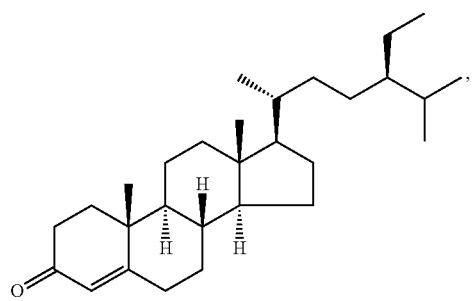
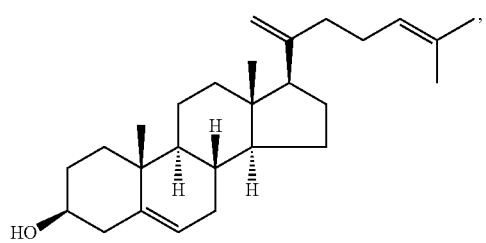
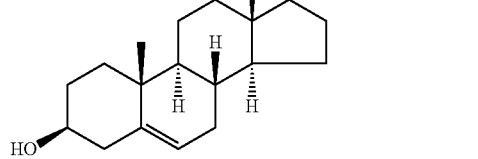
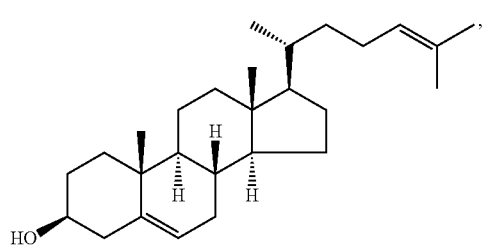
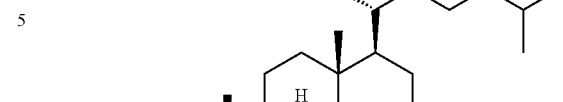
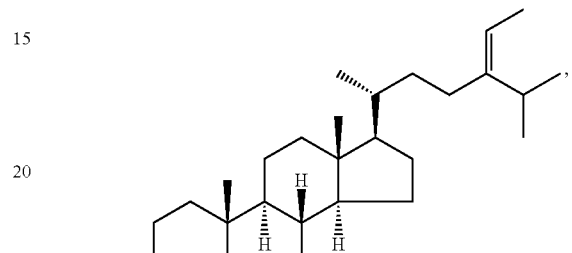
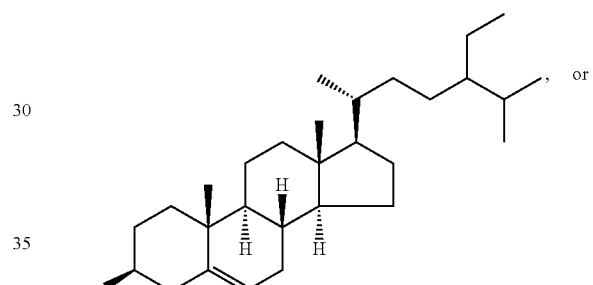
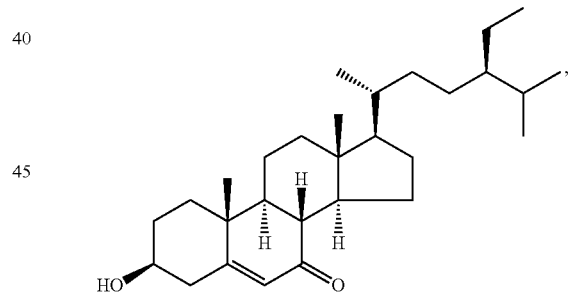
or a subgroup thereof.
In one aspect, a compound can be present as:
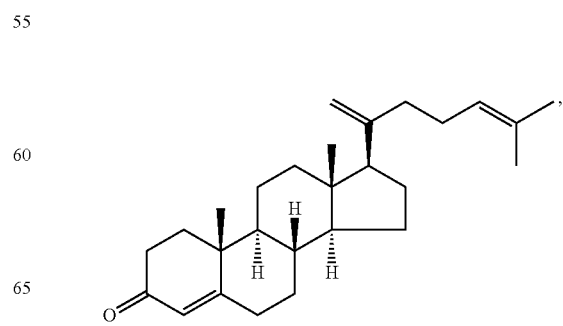

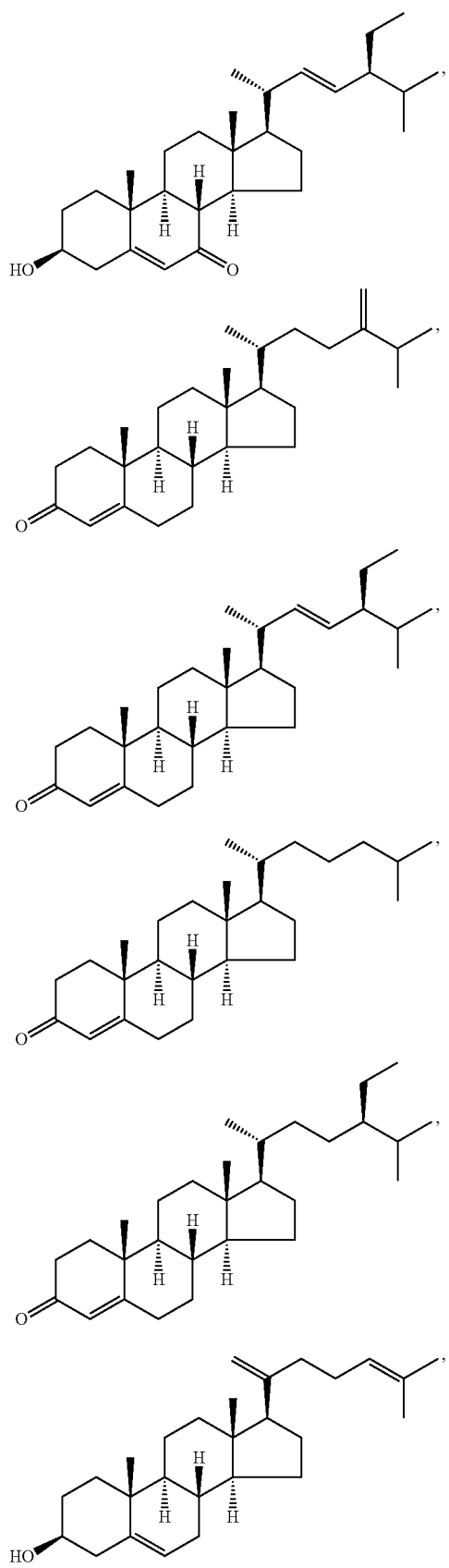
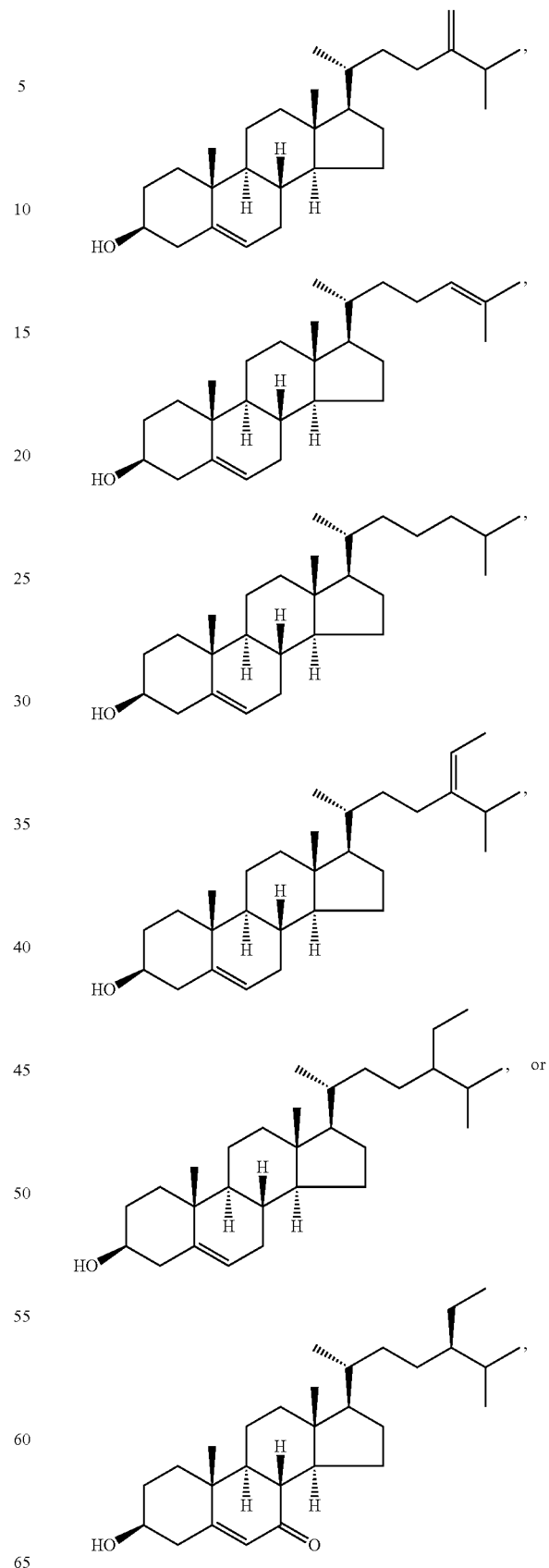
or a subgroup thereof.

In one aspect, a compound can be present as:
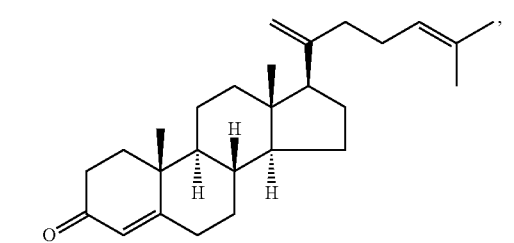
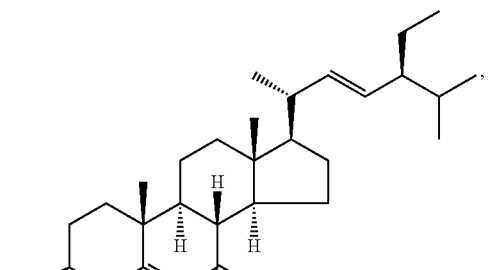
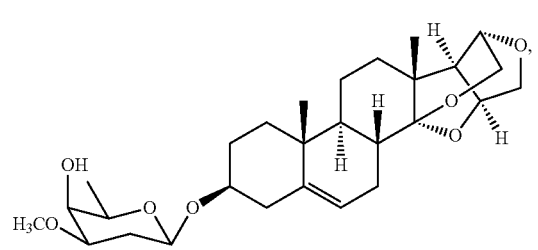
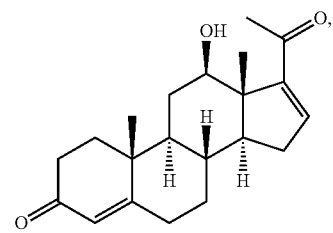
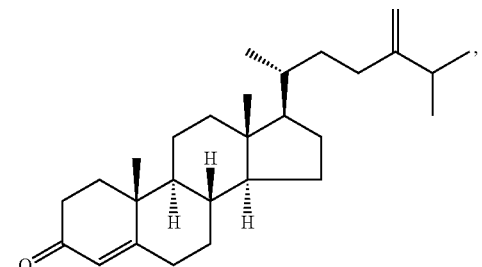
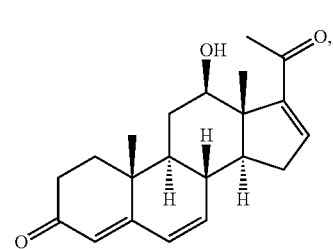
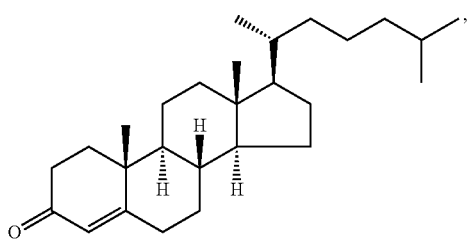
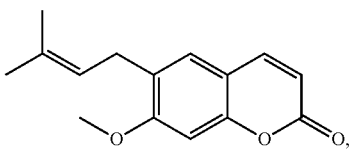
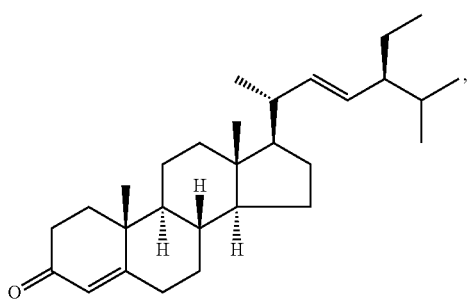
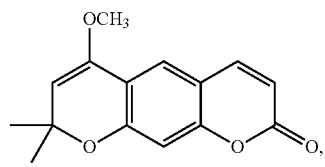
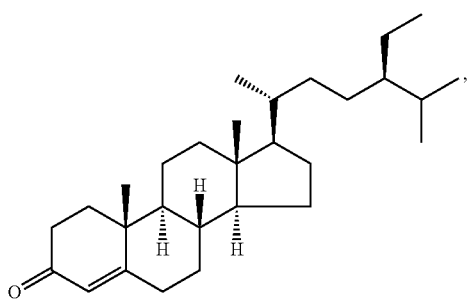
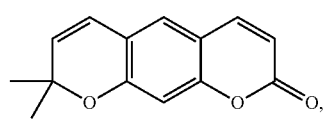
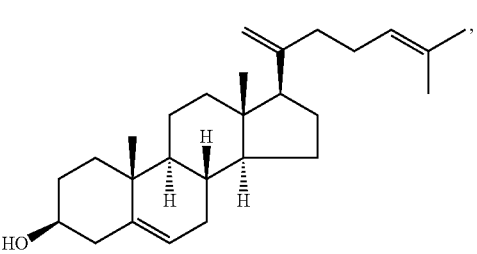

-continued
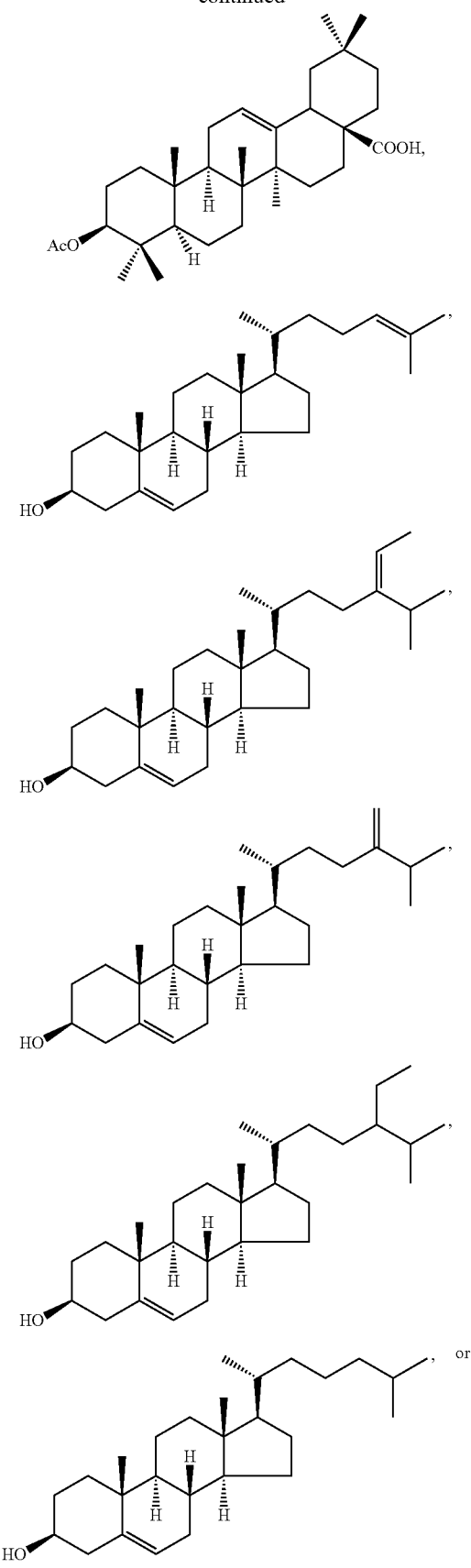
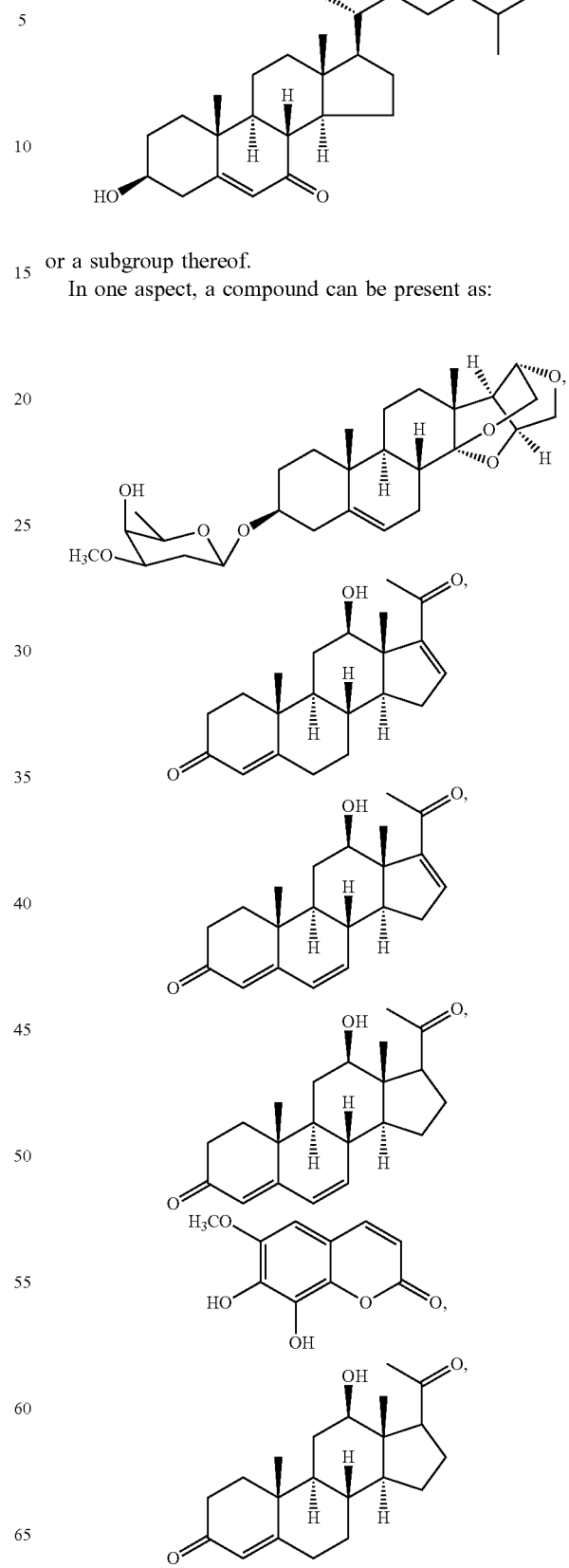
or a subgroup thereof.
In one aspect, a compound can be present as:

41
-continued
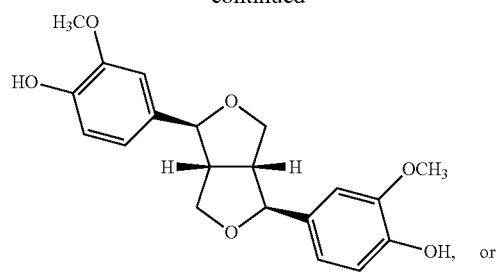
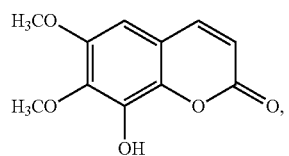
or a subgroup thereof.
In one aspect, a compound can be present as:
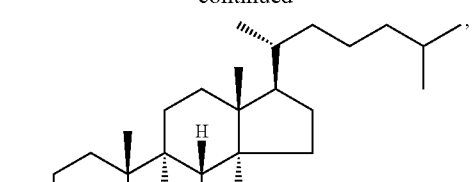
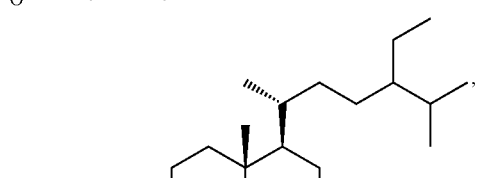
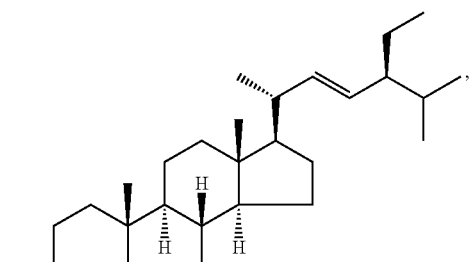
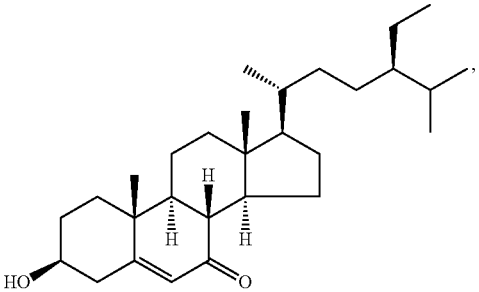
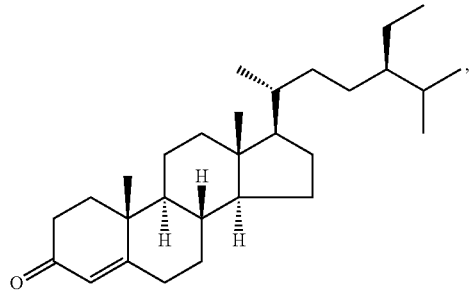
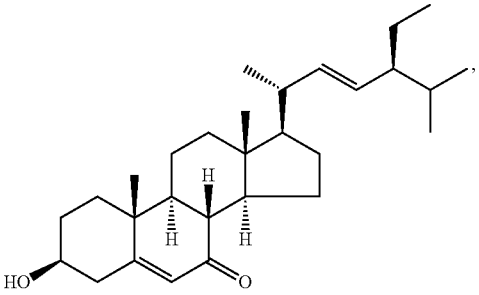
42
-continued -continued
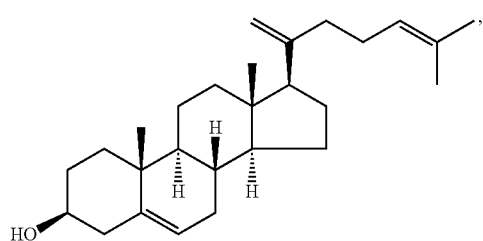
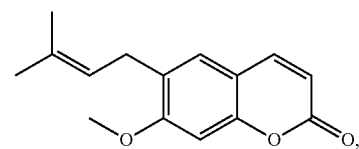
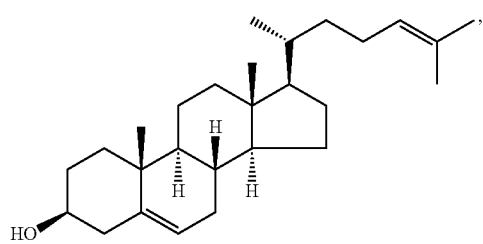
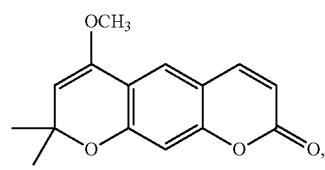
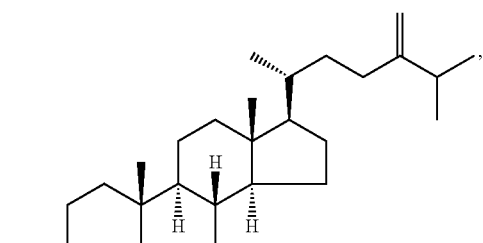
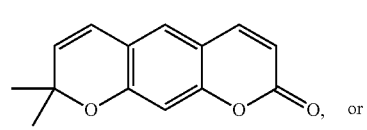, or
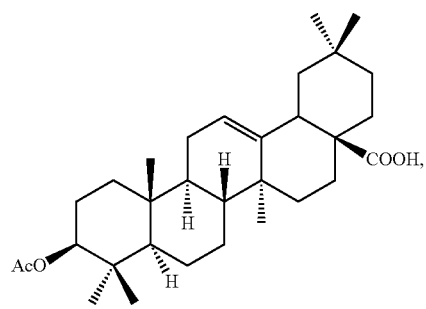
or a subgroup thereof.
In one aspect, a compound can be present as:
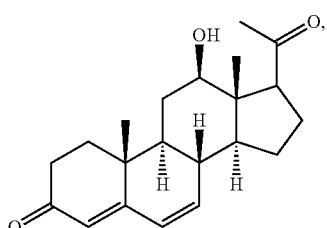
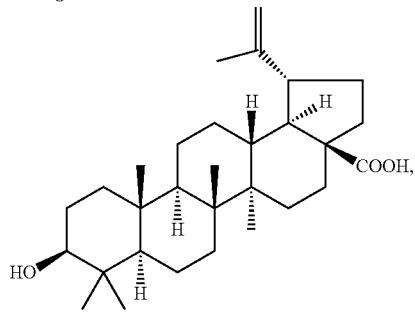
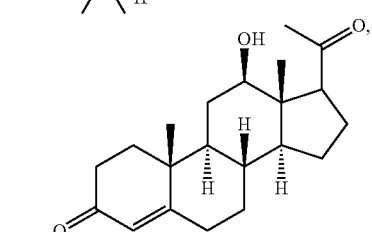
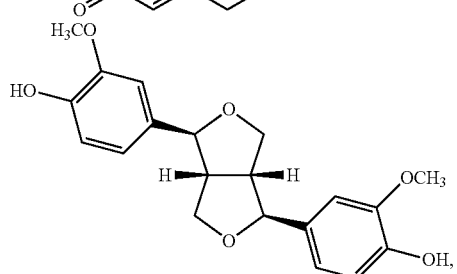
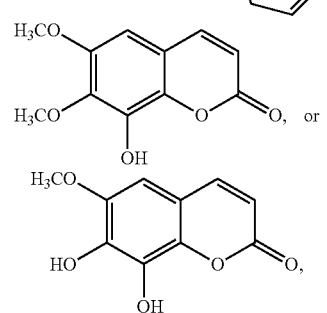, or
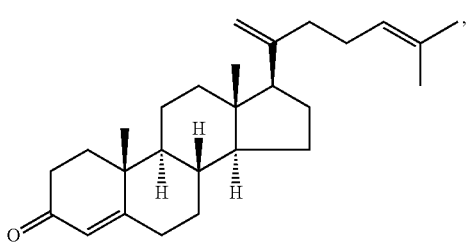
or a subgroup thereof.
In one aspect, a compound can be present as:
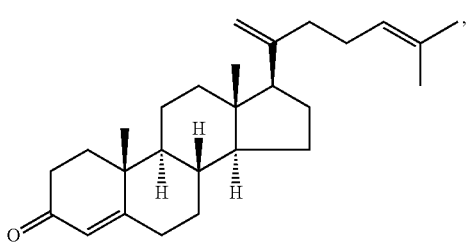

-continued
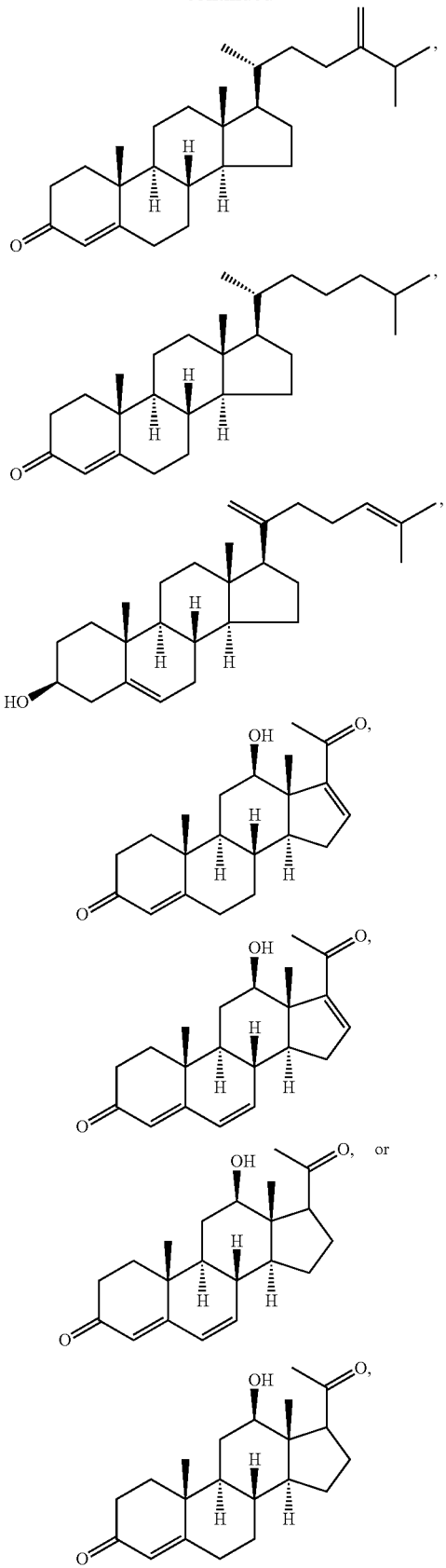
or a subgroup thereof.
In one aspect, a compound can be present as:
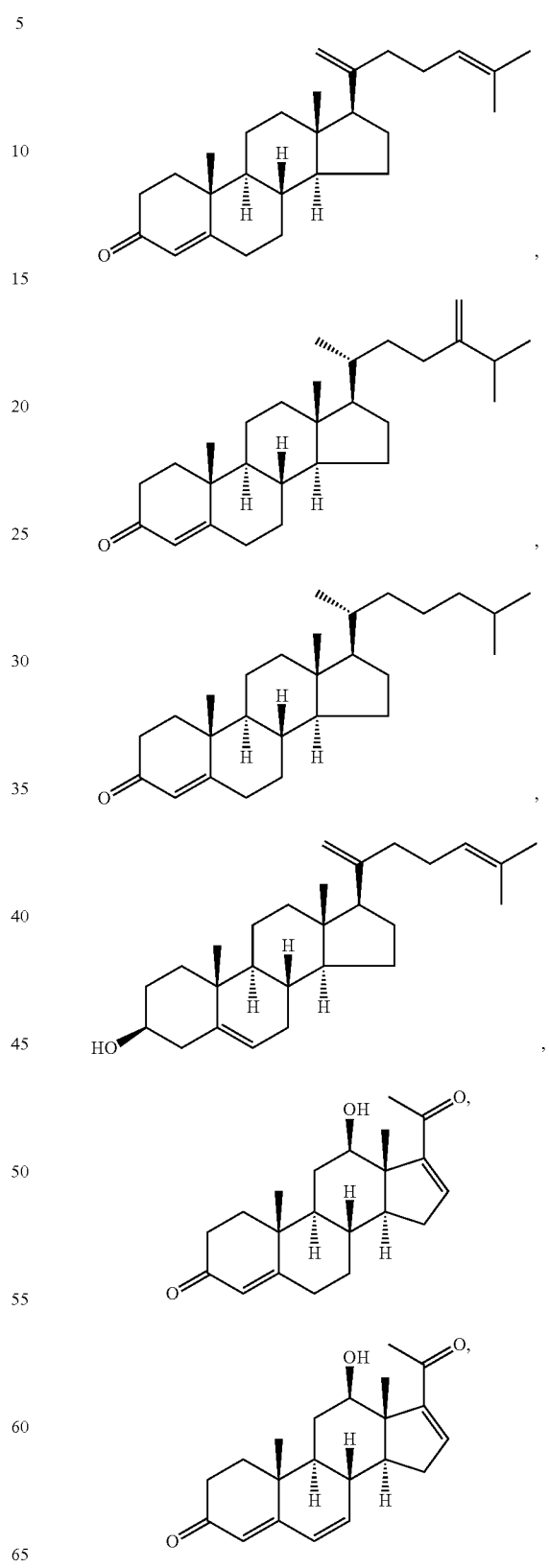
or a subgroup thereof.

In one aspect, a compound can be present as:
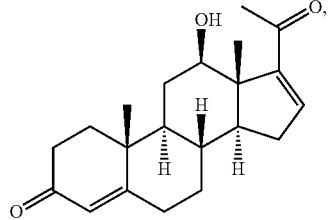
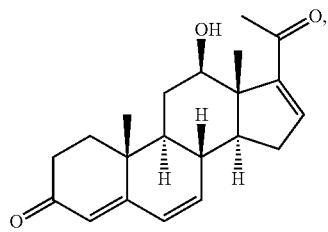
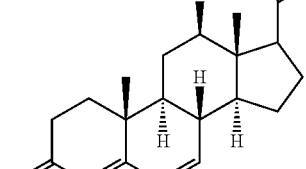
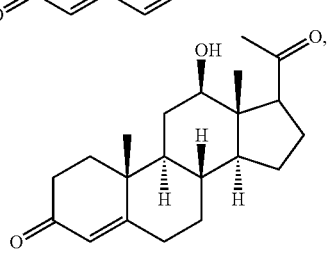
or a subgroup thereof.
In one aspect, a compound can be present as:
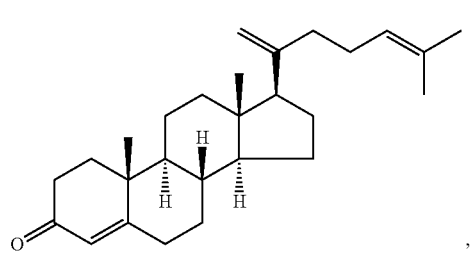
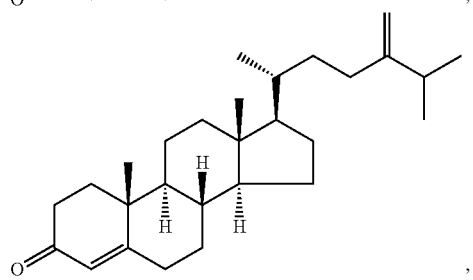
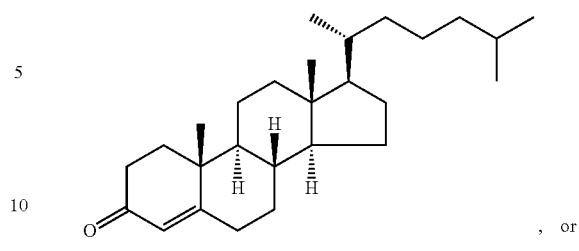
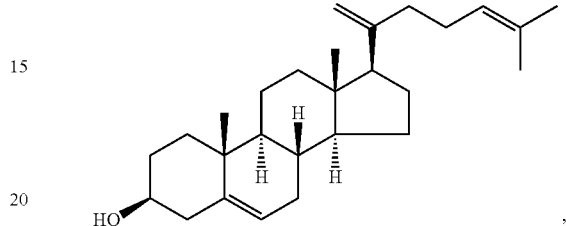
or a subgroup thereof.
In one aspect, a compound can be present as:
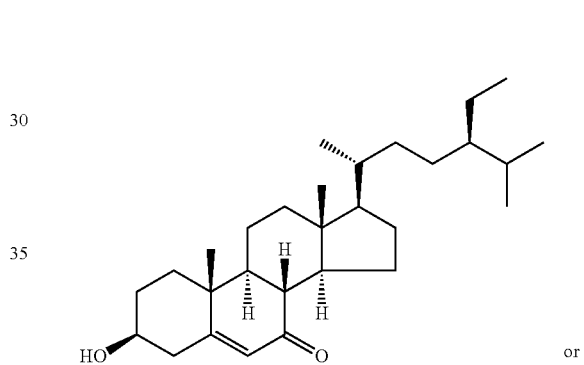
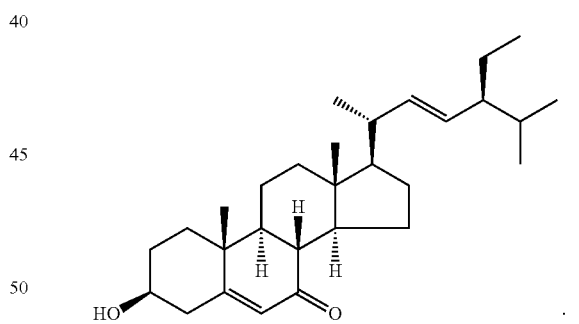
In one aspect, a compound can be present as:
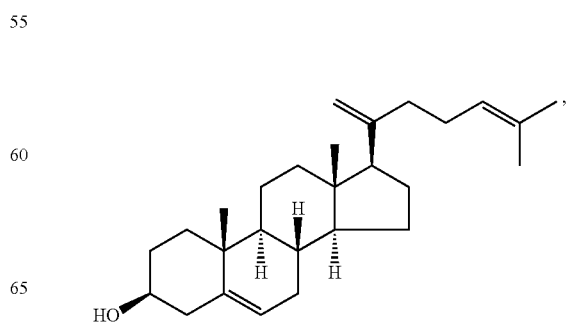

-continued
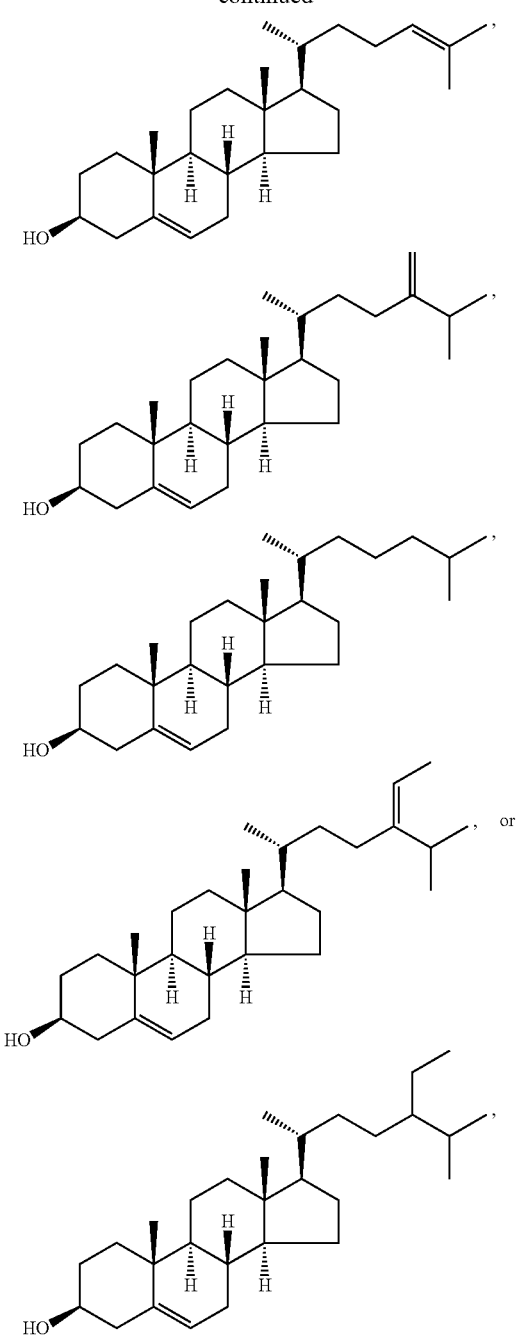
or a subgroup thereof.
In one aspect, a compound can be present as:
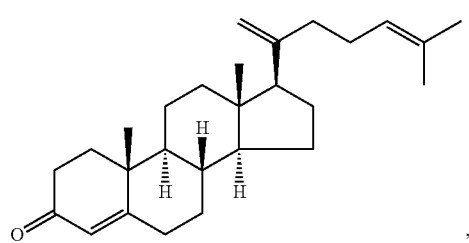
-continued
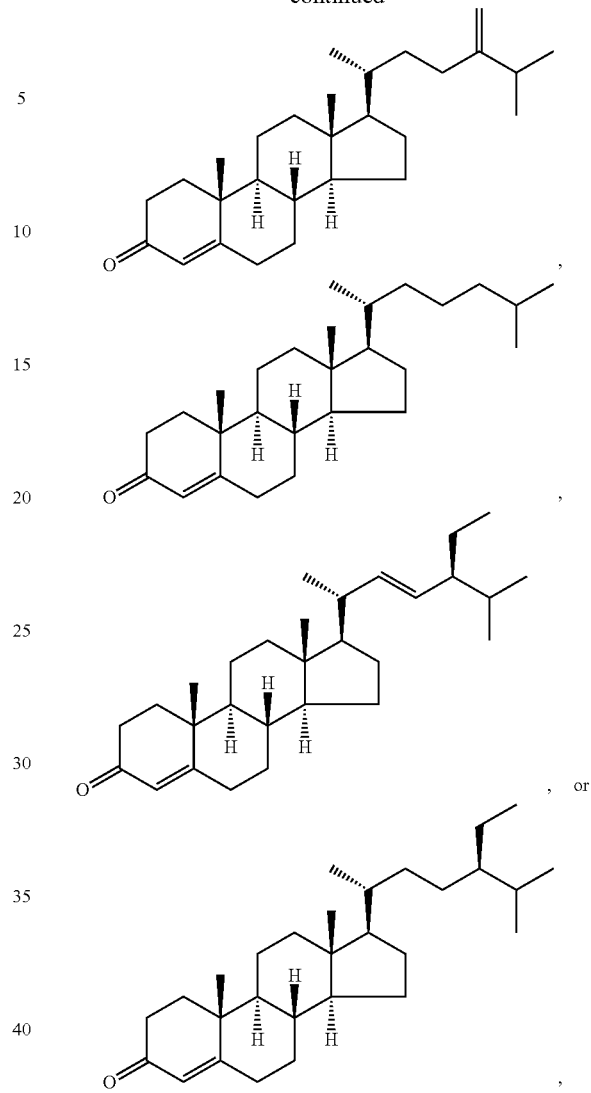
or a subgroup thereof.
In one aspect, a compound can be present as:
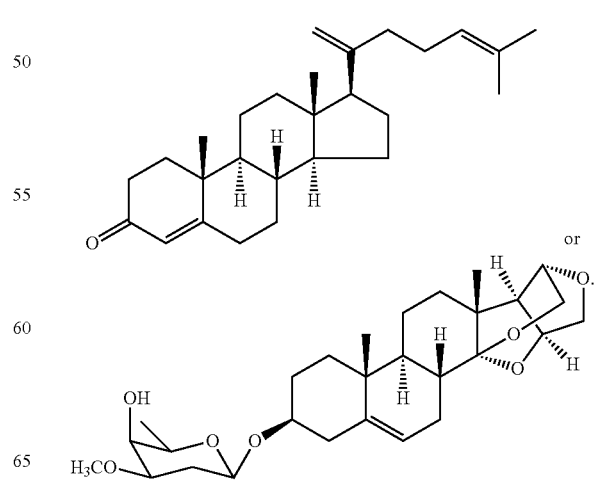

In one aspect, a compound can be present as:
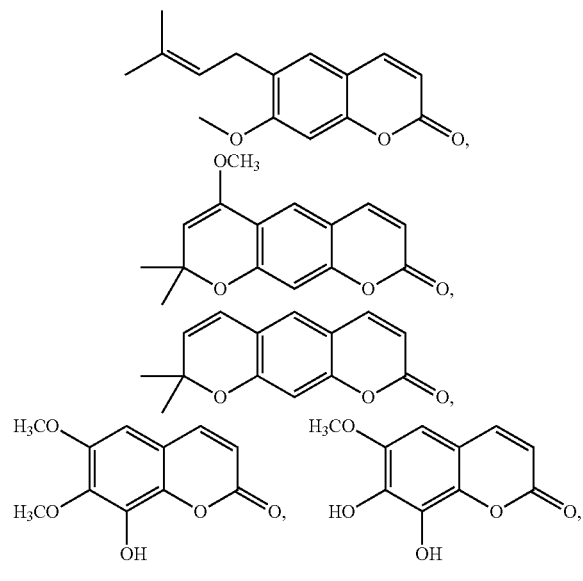
or a subgroup thereof.
In one aspect, a compound can be present as:
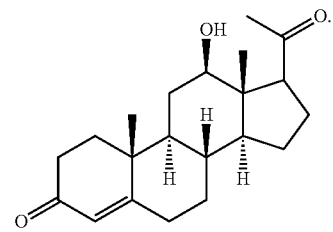
In one aspect, a compound can be present as:
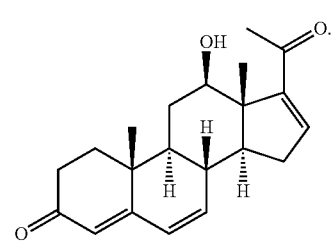
In one aspect, a compound can be present as:
In one aspect, a compound can be present as:
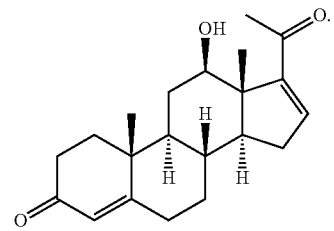
In one aspect, a compound can be present as:
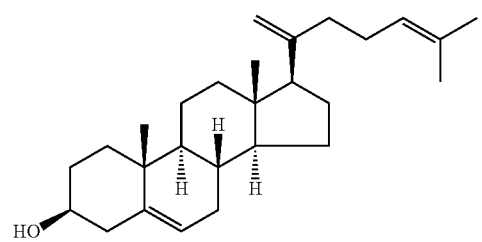
In one aspect, a compound can be present as:
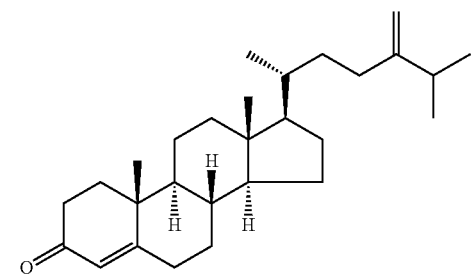
In one aspect, a compound can be present as:
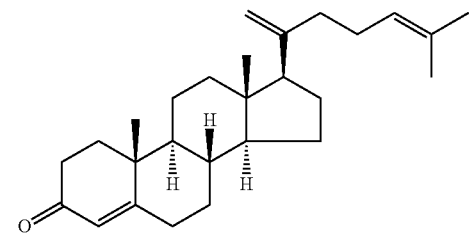

In one aspect, a compound can be present as:

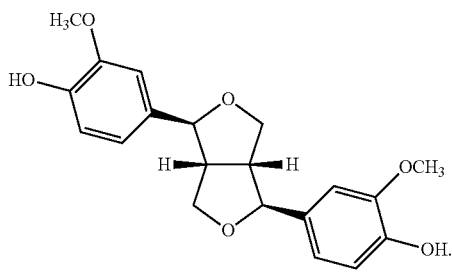 [SMILES: COc1cc([C@H]2OC[C@H]3[C@@H]2CO[C@@H]3c2ccc(O)c(OC)c2)ccc1O]

In one aspect, a compound can be present as:

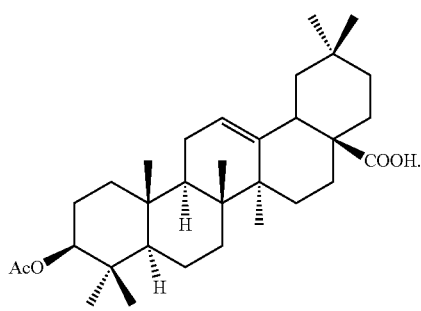

It is contemplated that one or more compounds can optionally be omitted from the disclosed invention.

C. METHODS OF ISOLATING THE COMPOUNDS FROM P. ANDRIEUXII

*Pentalinon andrieuxii* [(Muell.-Arg.); syn.: *Urechites andrieuxii* (B. F. Hansen & Wunderlin); Apocynaceae (Muell.-Arg.)], is a native plant in the Yucatan Peninsula of Mexico known as "bejuco guaco", "cantibteac", or "contrayerba". This plant is used in Mayan folk medicine to treat cutaneous leishmaniasis lesions (Chiclero's ulcer) in the states of Campeche and Quintana Roo, Mexico (Pulido, M. T.; Serralta, L. Centro de Investigaciones de Quintana Roo: Chetumal, Quintana Roo, Mexico, 1993, 6; Argücta, A.; Cano, L.; Rodartc, M. Instituto Nacional Indigenista: Mexico, D. F., 2, 204). Treatment of Chiclero's ulcer in Mayan traditional medicine uses the innermost part of the roots, which is fixed tightly to the skin lesions. This procedure is repeated each day after careful cleaning of lesions with an infusion of the roots, until visible healing is observed. In addition, this plant may be used also to treat snakebites as well as to alleviate headaches and nervous disturbances (Pulido and Serralta, op. cit.; Argüeta, et al., op. cit.). Previous biological studies on extracts of this plant have led to reports of antiatherogenic, anti-inflammatory, antileishmanial, and depressant activities (Jiu, J. Lloydia 1966, 29, 250; Lezama-Dávila, C. M.; Isaac-Márquez, A. P. Muell.-Arg. *Divulg. Bioméd.*, 1994, 2, 13; Chan-Bacab, M. J.; Balanza, E.; Deharo, E.; Muñoz, V.; Durán-García, R.; Peña-Rodríguez, L. M. *Journal of Ethnopharmacology* 2003, 86, 243; and Lezama-Davila, C. M.; Isaac-Marquez, A. P.; Zamora-Crescencio, P.; Úc-Encalada, M. R.; Justiniano-Apolinar, S. Y.; Angel-Robles, R.; Satoskar, A.; Hernandez-Rivero, L. *Fitoterapia* 2007, 78, 255).

Among these activities, the antileishmanial effect of this plant is of great interest. It has been reported that both aqueous and organic-solvent soluble extractives of *P. andrieuxii* roots showed in vitro antileishmanial activity, and the most active extract was ascribed to the hexane-soluble partition. A 10 μg/mL extract was effective in killing 1 million *L. mexicana* promastigotes cultured in vitro, with even more potent leishmanicidal activity than that of the control compound, meglumine antimoniate (Lezama-Davila, C. M.; Isaac-Marquez, A. P.; Zamora-Crescencio, P.; Úc-Encalada, M. R.; Justiniano-Apolinar, S. Y.; Angel-Robles, R.; Satoskar, A.; Hernandez-Rivero, L. *Fitoterapia* 2007, 78, 255). Thus far, the phytochemical investigation of this plant is very limited. Cardenolides, flavonoids, and two trinosesquiterpenoids were isolated as secondary metabolites from the roots of *P. andrieuxii* (Yam-Puc, A.; Escalante-Erosa, F.; Pech-López, M.; Chan-Bacab, M. J.; Arunachalampillai, A.; Wendt, O. F.; Sterner, O.; Peña-Rodríguez, L. M. *J. Nat. Prod.* 2009, 72, 745), but there are no active principles reported corresponding to the antileishmanial activity of this plant to date. The roots of *P. andrieuxii* were selected for an activity-guided fractionation following an initial screen for lethal effect on the protozoa of *Leishmania mexicana*.

In various aspects, the invention relates to methods of isolating compounds useful as therapeutic agents, which can be useful in the treatment of leishmaniasis and related diseases including, but not limited to malaria, human African trypanomiasis, babesiosis, Chagas disease, microsporidiosis, pneumocystosis, primary amoebic meningoenchephalitis, and toxoplasmosis. The compounds of this invention can be prepared by employing isolation methods as shown in the following schemes (e.g. see FIG. 2 and discussion in "Examples"), in addition to other standard manipulations that are known in the literature, exemplified in the experimental sections or clear to one skilled in the art.

In one aspect, the disclosed compounds comprise the products of the isolation methods described herein. In a further aspect, the disclosed compounds comprise a compound isolated by a method described herein. In a still further aspect, the invention comprises a pharmaceutical composition comprising a therapeutically effective amount of the product of the disclosed isolation methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

It is contemplated that each disclosed methods can further comprise additional steps, manipulations, and/or components. It is also contemplated that any one or more step, manipulation, and/or component can be optionally omitted from the invention. It is understood that a disclosed methods can be used to provide the disclosed compounds. It is also understood that the products of the disclosed methods can be employed in the disclosed methods of using.

D. HEMISYNTHESIS OF DISCLOSED COMPOUNDS

The compounds of the present invention can be obtained by isolation from *Pentalinon andrieuxii* as described herein. Alternatively, the compounds can be prepared by synthetic methods, e.g. hemisynthetic methods beginning with the appropriate commercially available sterol precursor. For example, an analogue of compound 1 can be prepared as shown in the synthetic scheme below.

55 56
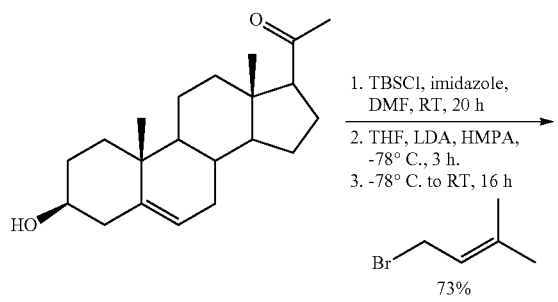
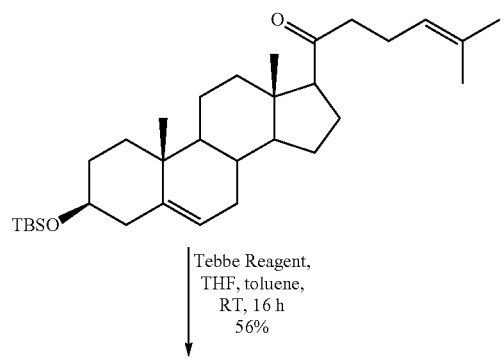
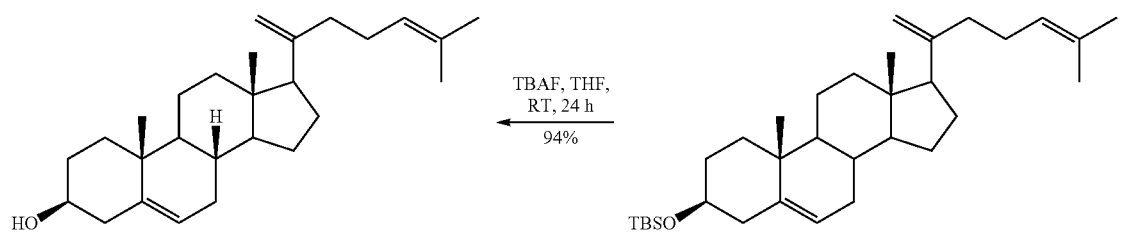
The reaction conditions shown above can be used to prepare additional analogues with alkyl substituents at the carbonyl. The above reaction with exemplary alkyl substituents is illustrated below.
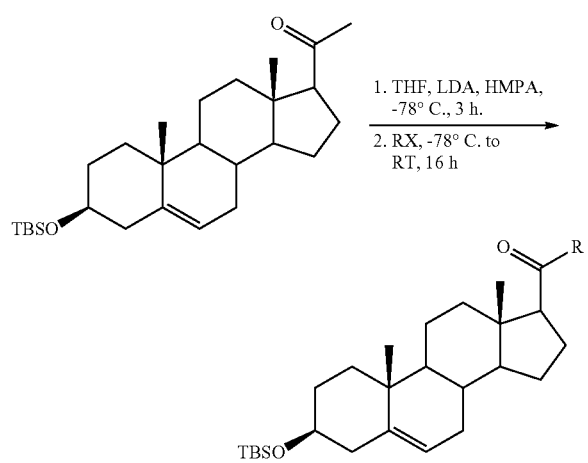
-continued
RX:
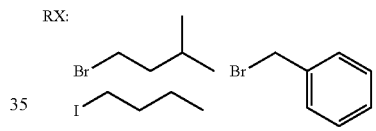
R:
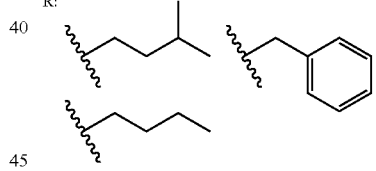
Alternatively, compounds can be prepared as described in the reaction scheme shown below.
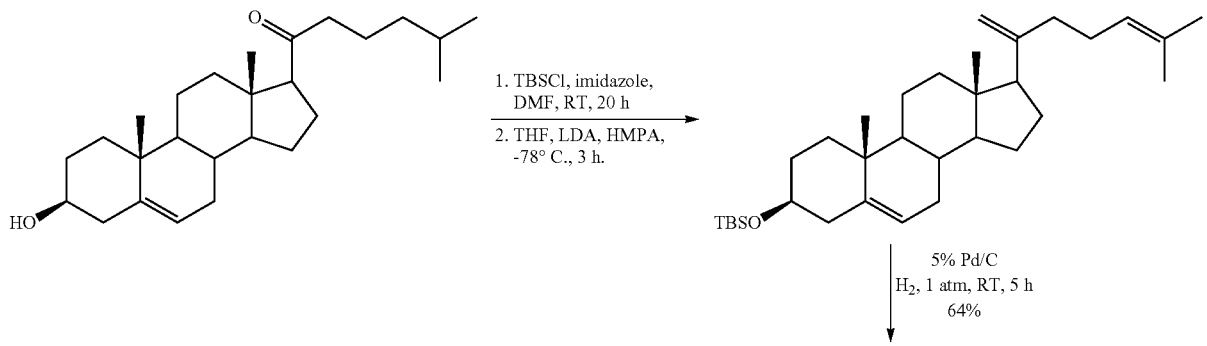

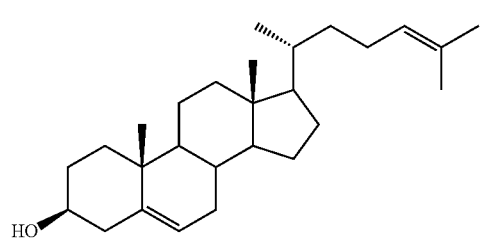
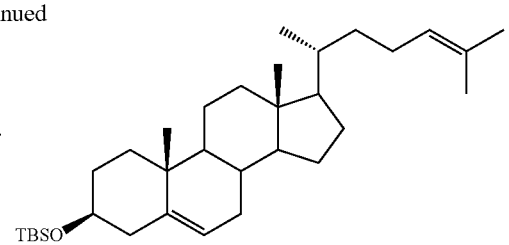

Alternatively, compounds of the invention can be prepared as described in the reaction scheme shown below.

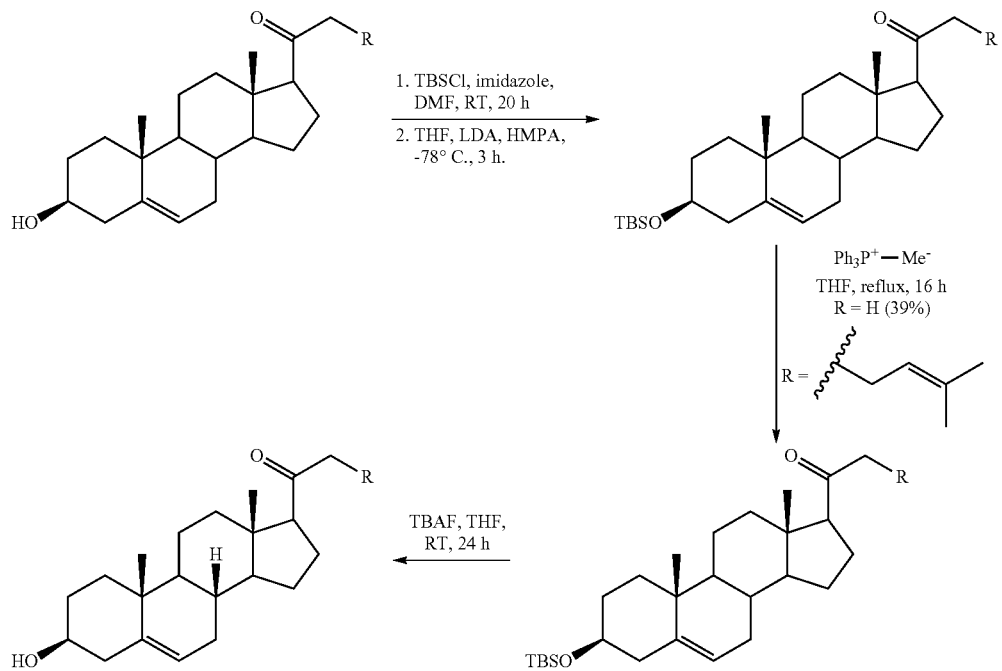

E. PHARMACEUTICAL COMPOSITIONS

In one aspect, the invention relates to a pharmaceutical composition comprising a pharmaceutically acceptable carrier and an effective amount of a compound represented by a formula:

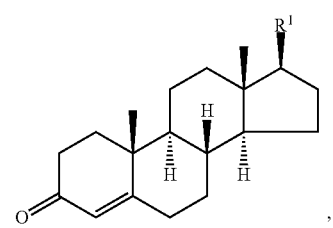

,

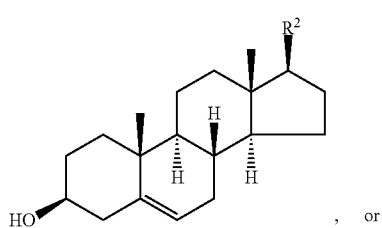

, or

-continued

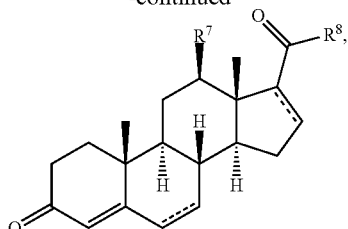

, wherein each ---- is independently an optional covalent bond, wherein valence is satisfied; wherein $R^1$, when present, is selected from C1-C12 alkyl and C1-C12 alkenyl; wherein $R^2$, when present, is selected from C1-C12 alkyl and C1-C12 alkenyl; wherein $R^7$ is selected from hydrogen, hydroxyl, amino, and halogen; and wherein $R^8$ is selected from hydrogen and C1-C6 alkyl; or a pharmaceutically acceptable salt, solvate, or polymorph thereof.

In a further aspects, the pharmaceutical composition comprises oral administration of compound 1, 2, derivatives thereof, and any combination of 1, 2, and related compounds to a mouse model, related biological models, human subjects, clinical subjects, and patients being treated for leishmaniasis and related diseases including, but not limited to malaria, human African trypanomiasis, babesiosis, Chagas disease, microsporidiosis, pneumocystosis, primary amoebic meningoenchephalitis, and toxoplasmosis.

In a further aspects, the pharmaceutical composition comprises intraperitoneal ("IP") injection, intravenous administration, or both methods of administering compound 1, 2, derivatives thereof, and any combination of 1, 2, and related compounds to a mouse model, related biological models, human subjects, clinical subjects, and patients being treated for leishmaniasis and related diseases including, but not limited to malaria, human African trypanomiasis, babesiosis, Chagas disease, microsporidiosis, pneumocystosis, primary amoebic meningoenchephalitis, and toxoplasmosis.

In a further aspect, the pharmaceutical composition comprises oral, topical, or both methods of administering compound 1, 2, derivatives thereof, and any combination of 1, 2, and related compounds to a mouse model, related biological models, human subjects, clinical subjects, and patients being treated for leishmaniasis and related diseases including, but not limited to malaria, human African trypanomiasis, babesiosis, Chagas disease, microsporidiosis, pneumocystosis, primary amoebic meningoenchephalitis, and toxoplasmosis.

In a further aspects, the pharmaceutical composition comprises intranasal administration, pulmonary delivery (e.g. using a metered dose dry powder inhaler), or both methods of administering compound 1, 2, derivatives thereof, and any combination of 1, 2, and related compounds to a mouse model, related biological models, human subjects, clinical subjects, and patients being treated for leishmaniasis and related diseases including, but not limited to malaria, human African trypanomiasis, babesiosis, Chagas disease, microsporidiosis, pneumocystosis, primary amoebic meningoenchephalitis, and toxoplasmosis.

In various aspects, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In a further aspect, the pharmaceutical composition further comprises an effective amount of a therapeutic agent selected from pentavalent antimonial, pentamidine, amphotericin B, allopurinol, ketaconazole, suramin, melarsoprol, paramomycin, miltefosine, sitamaquine, imiquimod, eflornitine, nifurtimox, benznidazole, crystal violet, amiodarone, ethidium, isomethamidium, and berenil.

In various aspects, the pharmaceutical composition further comprises a therapeutic agent, wherein the therapeutic agent is selected from eflornitine, ethidium, isomethamidium, and berenil. In a further aspect, the pharmaceutical composition further comprises a therapeutic agent, wherein the therapeutic agent is a pentavalent antimonial and wherein the pentavalent antimonial is selected from sodium stibogluoconate and meglumine antimoniate. In a still further aspect, the pharmaceutical composition further comprises a pentavalent antimonial, wherein the pentavalent antimonial is sodium stibogluoconate. In a yet further aspect, the pharmaceutical composition further comprises a pentavalent antimonial, wherein the pentavalent antimonial is meglumine antimoniate. In an even further aspect, the pharmaceutical composition further comprises a therapeutic agent, wherein the therapeutic agent is amphotericin B. In a still further aspect, the pharmaceutical composition further comprises a therapeutic agent, wherein the therapeutic agent is pentamidine. In a yet further aspect, the pharmaceutical composition further comprises a therapeutic agent, wherein the therapeutic agent is miltefosine.

In a further aspect, the pharmaceutical composition comprises an effective amount of the compound. In a still further aspect, the effective amount is a therapeutically effective amount. In a yet further aspect, the effective amount is a prophylatically effective amount.

In a further aspect, the pharmaceutically acceptable carrier is selected from a liposome, nanoparticle, microparticle, cyclodextrins, nanoemulsion, microemulsion, polymersome, surfactant, biocompatible organic solvent, and micelle. In a still further aspect, the surfactant is selected from a phospholipid, a poloxamer, and a polysorbate. In a yet further aspect, the biocompatible organic solvent is selected from propylene glycol, polyethylene glycols, ethanol), dimethyl sulfoxide, N-methyl-2-pyrrolidone, glycofurol, Solketal™, glycerol formal, acetone tetrahydrofurfuryl alcohol, diglyme, dimethyl isosorbide, cremophor, and ethyl lactate.

In a further aspect, the pharmaceutically acceptable carrier is a liposome. In a still further aspect, the liposome comprises a phospholipid. In a yet further aspect, the liposome comprises one or more lipids selected from phosphatidylcholine, tocopherol, cholesterol, and 1,2-distearoyl-phosphatidyl ethanolamine-methyl-polyethyleneglycol conjugate. In an even further aspect, the liposome comprises phosphatidylcholine and tocopherol. In a still further aspect, the liposome further comprises an effective amount of a therapeutic agent is selected from pentavalent antimonial, pentamidine, amphotericin B, allopurinol, ketaconazole, suramin, melarsoprol, paramomycin, miltefosine, sitamaquine, imiquimod, eflornitine, nifurtimox, benznidazole, crystal violet, amiodarone, ethidium, isomethamidium, and berenil.

In various aspects, the pharmaceutically acceptable carrier is a liposome, wherein the liposome further comprises a therapeutic agent, and wherein the therapeutic agent is selected from eflornitine, ethidium, isomethamidium, and berenil. In a further aspect, the pharmaceutically acceptable carrier is a liposome, wherein the liposome further comprises a therapeutic agent, wherein the therapeutic agent is a pentavalent antimonial and wherein the pentavalent antimonial is selected from sodium stibogluoconate and meglumine antimoniate. In a still further aspect, the pharmaceutically acceptable carrier is a liposome, wherein the liposome further comprises a therapeutic agent, wherein the therapeutic agent is a pentavalent antimonial and wherein the pentavalent antimonial is sodium stibogluoconate. In a yet further aspect, the pharmaceutically acceptable carrier is a liposome, wherein the liposome further comprises a therapeutic agent, wherein the therapeutic agent is a pentavalent antimonial and wherein the pentavalent antimonial is meglumine antimoniate. In an even further aspect, the pharmaceutically acceptable carrier is a liposome, wherein the liposome further comprises a therapeutic agent, wherein the therapeutic agent is amphotericin B. In a still further aspect, the pharmaceutically acceptable carrier is a liposome, wherein the liposome further comprises a therapeutic agent, wherein the therapeutic agent is pentamidine. In a yet further aspect, the pharmaceutically acceptable carrier is a liposome, wherein the liposome further comprises a therapeutic agent, wherein the therapeutic agent is miltefosine.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intradermal, intramuscular, intraperitoneal, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the invention also relates to a pharmaceutical composition comprising a pharmaceutically acceptable carrier or diluent and, as active ingredient, a therapeutically effective amount of a disclosed compound, a product of a disclosed method of making, a pharmaceutically acceptable salt thereof, a hydrate thereof, a solvate thereof, a polymorph thereof, or a stereochemically isomeric form thereof. In a further aspect, a disclosed compound, a product of a disclosed method of making, a pharmaceutically acceptable salt thereof, a hydrate thereof, a solvate thereof, a polymorph thereof, or a stereochemically isomeric form thereof, or any subgroup or combination thereof may be formulated into various pharmaceutical forms for administration purposes.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

For therapeutic use, salts of the disclosed compounds are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable acid and base addition salts as mentioned hereinabove or hereinafter are meant to comprise the therapeutically active non-toxic acid and base addition salt forms which the disclosed compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The disclosed compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Because of the ease in administration, oral administration is preferred, and tablets and capsules represent the most advantageous oral dosage unit forms in which case solid pharmaceutical carriers are obviously employed. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, intradermal, intraperitoneal, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations.

Pharmaceutical compositions of the present invention can be in a form suitable for topical use such as, for example, an aerosol, cream, ointment, lotion, dusting powder, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

The exact dosage and frequency of administration depends on the particular disclosed compound, a product of a disclosed method of making, a pharmaceutically acceptable salt thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

In the treatment conditions which require inhibition of parasitic activity in a cell, an appropriate dosage level will generally be about 0.01 to 1000 mg per kg patient body weight per day and can be administered in single or multiple doses. In various aspects, the dosage level will be about 0.1 to about 500 mg/kg per day, about 0.1 to 250 mg/kg per day, or about 0.5 to 100 mg/kg per day. A suitable dosage level can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

Such unit doses as described hereinabove and hereinafter can be administered more than once a day, for example, 2, 3, 4, 5 or 6 times a day. In various aspects, such unit doses can be administered 1 or 2 times per day, so that the total dosage for a 70 kg adult is in the range of 0.001 to about 15 mg per kg weight of subject per administration. In a further aspect, dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The present invention is further directed to a method for the manufacture of a medicament for inhibiting parasitic activity (e.g., treatment of one or more parasitic diseases) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

As already mentioned, the invention relates to a pharmaceutical composition comprising a therapeutically effective amount of a disclosed compound, a product of a disclosed method of making, a pharmaceutically acceptable salt thereof, a hydrate thereof, a solvate thereof, a polymorph thereof, and a pharmaceutically acceptable carrier. Additionally, the invention relates to a process for preparing a such pharmaceutical composition, characterized in that a pharmaceutically acceptable carrier is intimately mixed with a therapeutically effective amount of a compound according to the invention.

As already mentioned, the invention also relates to a pharmaceutical composition comprising a disclosed compound, a product of a disclosed method of making, a pharmaceutically acceptable salt thereof, a hydrate thereof, a solvate thereof, a polymorph thereof, and one or more other drugs in the treatment, prevention, control, amelioration, or reduction of risk of diseases or conditions for a disclosed compound or the other drugs may have utility as well as to the use of such a composition for the manufacture of a medicament. The present invention also relates to a combination of disclosed compound, a product of a disclosed of isolating a compound from *Pentalinon andrieuxii*, a pharmaceutically acceptable salt thereof, a hydrate thereof, a solvate thereof, a polymorph thereof, and an anti-parasitic compound that is not a disclosed compound. The present invention also relates to such a combination for use as a medicine. The present invention also relates to a product comprising (a) disclosed compound, a product of a disclosed method of making, a pharmaceutically acceptable salt thereof, a hydrate thereof, a solvate thereof, a polymorph thereof, and (b) an anti-parasitic compound known to treat an infection with a hemoflagellated protozoa, as a combined preparation for simultaneous, separate or sequential use in the treatment or prevention of a condition in a mammal, including a human, the treatment or prevention of which is affected or facilitated by the anti-parasitic compounds, in particular compounds which treat a disease associated with infection by a with a hemoflagellated protozoa such as *Leishmania* spp or *Trypanosoma* spp. The different drugs of such a combination or product may be combined in a single preparation together with pharmaceutically acceptable carriers or diluents, or they may each be present in a separate preparation together with pharmaceutically acceptable carriers or diluents.

F. METHODS OF USING THE COMPOUNDS AND COMPOSITIONS

Leishmaniasis is a protozoan vector borne parasitic disease caused by protozoan parasites of the genus *Leishmania* and is transmitted through the bite of certain species of *Phlembotominae* sandfly. Of the approximately 30 species of *Leishmania* known to infect mammals, 21 of these species are believed to cause leishmaniasis in humans. Leishmaniasis manifests in three distinct forms including; cutaneous leishmaniasis ("CL"), visceral leishmaniasis ("VL") and mucocutaneous leishmaniasis ("ML"). Leishmaniasis typically presents as skin sores or ulcers which erupt weeks to months after the person is bitten. However, if left untreated, the infection can progress and lead to splenomegaly, liver damage, renal damage, anemia, and death. Due to the complex life cycles (FIG. 2) of the causative parasites, leishmaniasis is rarely diagnosed in its early stages when therapeutic intervention is most effective. The parasite life cycle typically begins when sandflies transfer metacyclic promastigotes during blood meals. Metacyclic promastigotes that reach the puncture wound are ingested or phagocytized by macrophages. Inside the macrophages, the promastigotes transform into amastigotes. Here, the amastigotes multiply in infected cells and affect different tissues. These differing tissue specificities cause the differing clinical manifestations of the various forms of leishmaniasis as described above. The cycle is continued when sandflies become infected during blood meals from infected hosts when they ingest macrophages infected with amastigotes. In the sandfly's midgut, the parasites differentiate into promastigotes, then multiply, and differentiate into metacyclic promastigotes to repeat the cycle. Leishmaniasis typically presents as skin sores or ulcers which erupt weeks to months after the person is bitten. However, if left untreated, the infection can progress and lead to splenomegaly, liver damage, renal damage, anemia, and death.

Like fungi, the predominant endogenous sterols found in *Leishmania* species are ergosterol and its derivatives, and these sterols are constituents of cell membranes, which are essential for the normal structure and function of these parasites (de Souza, W.; Rodrigues, J. C. F. Interdiscip. Perspect. Infect. Dis. 2009, doi: 10.1155/2009/642502). Thus, the sterol biosynthesis pathway is considered as a promising target in the development of new therapeutic agents for the treatment of parasitic diseases (Werbovetz, K. A. Exert Opin. Ther. Targets. 2002, 6, 407-422). In recent years, studies have shown that a number of sterol-derived compounds exhibit antileishmanial activities, and some of them such as azasterols are reported as inhibitors of certain enzymes involved in the sterol biosynthesis pathway of these parasites (Haughan, P. A.; Chance, M. L.; Goad, L. J. Biochem. J. 1995, 308, 31-38; Magaraci, F.; Jimenez, C. J.; Rodrigues, C.; Rodrigues, J. C.; Braga, M. V.; Yardley, V.; de Luca-Fradley, K.; Croft, S. L.; de Souza, W.; Ruiz-Perez, L. M.; Urbina, J.; Gonzalez, J. *J. Med. Chem.* 2003, 46, 4714-4727; Bazin, M.-A.; Loiseau, P. M.; Bories, C.; Letourneux, Y.; Rault, S.; El Kihel, L. *Eur. J. Med. Chem.* 2006, 41, 1109-1116; and Sartorelli, P.; Andrade, S. P.; Melhem, M. S. C.; Prado, F. O.; Tempone, A. G. *Phytother. Res.* 2007, 21, 644-647).

The structure of the disclosed compounds, e.g. pentalionsterol, closely mimics *Leishmania*-synthesized sterols which are critical for lipid synthesis in the parasite. Without wishing to be bound by a particular theory, the active sterols isolated from *P. audriexii* in the present invention can exert their activity by acting as antagonists of endogenous sterols to interfere or inhibit sterol biosynthesis and lead to organism death. Thus, in one aspect, the disclosed sterols can have therapeutic anti-*Leishmania* activity via dysregulation of the synthesis of parasite lipids which are required for membrane integrity. Further, and without wishing to be bound by a particular theory, since similar pathways are also present in other protozoan parasites, it is believed that the disclosed compounds can display antiparasitic activity against other pathogens, such as *Trypanosoma, Plasmodium,* and *Toxoplasma.*

Hence, the present invention relates to compounds and compositions disclosed herein for use as a medicament, as well as to the use of a compound or composition disclosed herein or a pharmaceutical composition according to the invention for the manufacture of a medicament, including, for example, the manufacture of a medicament for treating or preventing, in particular treating, a condition in a mammal, including a human, the treatment or prevention of which is affected or facilitated by anti-protozoal activity, e.g. by anti-leishmanial activity. The present invention also relates to a compound disclosed herein or a pharmaceutical composition according to the invention for use in the treatment or prevention of a condition in a subject such as a mammal, including a human, the treatment or prevention of which is affected or facilitated by anti-protozoal activity, e.g. by anti-leishmanial activity.

a. Treatment of a Parasitic Disease: Administering a Compound

In one aspect, the invention relates to a method for the treatment of a parasitic disease in a mammal diagnosed with the disease, the method comprising the step of administering to the mammal a therapeutically effective amount of at least one compound having a structure represented by a formula:

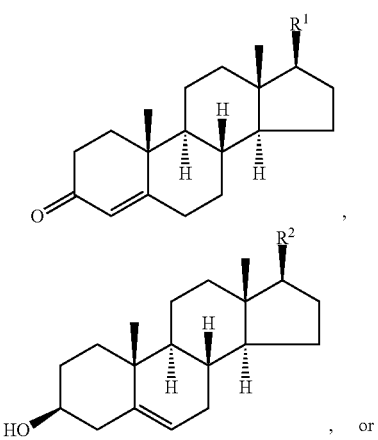

, or

-continued

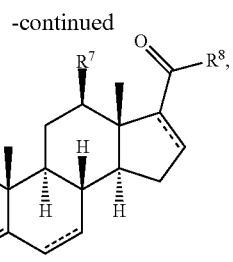

wherein each ---- is independently an optional covalent bond, wherein valence is satisfied; wherein $R^1$, when present, is selected from C1-C12 alkyl and C1-C12 alkenyl; wherein $R^2$, when present, is selected from C1-C12 alkyl and C1-C12 alkenyl; wherein $R^7$ is selected from hydrogen, hydroxyl, amino, and halogen; and wherein $R^8$ is selected from hydrogen and C1-C6 alkyl; or a pharmaceutically acceptable salt, solvate, or polymorph thereof.

In a further aspect, the invention relates to a method for the treatment of a parasitic disease in a mammal comprising the step of administering to the mammal an effective amount of at least one compound; or a pharmaceutically acceptable salt, hydrate, solvate, or polymorph thereof; wherein the compound is a disclosed compound or a product of a disclosed method of isolating a compound from *P. andrieuxii*.

In a further aspect, the invention relates to a method for the treatment of a parasitic disease in a mammal comprising the step of administering to the mammal at least one disclosed compound or a product of a disclosed method of isolating a compound from *P. andrieuxii*, in a dosage and amount effective to treat the disorder in the mammal.

In a further aspect. the parasitic disease is associated with a hemoflagellated protozoa.

In a further aspect, the parasitic disease is associated with infection of the mammal by *Leishmania* spp. In a still further aspect, the *Leishmania* spp. is selected from *Leishmania donovani, Leishmannia brasiliensis, Leishmania mexicana, Leishmania amazonensis, Leishmania aethiopica, Leishmania major, Leishmania chagasi, Leishmania panamensis, Leishmania infantum*, and *Leishmania tropica*.

In a further aspect, the parasitic disease is associated with infection of the mammal by *Trypanosoma* spp. In a still further aspect, the *Trypanosoma* spp. is selected from *Trypanosoma brucei, Trypanosoma cruzi, Trypanosoma brucei gambiense, Trypanosoma brucei rhodesiense, Trypanosoma congolense, Trypanosoma equinum, Trypanosoma equiperdum, Trypanosoma melophagium, Trypanosoma theileri*, and *Trypanosoma vivax*.

In a further aspect, the parasitic disease is a trypanosomiases. In a still further aspect, the trypanosomiases is Chaga's disease.

In a further aspect, the parasitic disease is a leishmaniases. In a still further aspect, the leishmaniases is visceral leishmaniasis, cutaneous leishmaniasis, mucocutaneous leishmaniasis, diffus cutaneous leishmaniasis, recidivans leishmaniasis, and post-kala-azar dermal leishmaniasis. In a yet further aspect, the leishmaniases is cutaneous leishmaniasis. In an even further aspect, the leishmaniases is visceral leishmaniasis.

In a further aspect, an effective amount is a therapeutically effective amount. In a still further aspect, an effective amount is a prophylatically effective amount. In a yet further aspect, treatment is symptom amelioration or prevention, and wherein an effective amount is a prophylatically effective amount.

In a further aspect, the mammal that the compound is administered to is a human. In a still further aspect, the mammal that the compound is administered to is a bovine. In a yet further aspect, the mammal that the compound is administered to is a canine. In a further aspect, the mammal has been diagnosed with a need for treatment of the disorder prior to the administering step. In a further aspect, the method further comprises the step of identifying a mammal in need of treatment of the disorder.

In a further aspect, the parasitic disease is leishmaniasis and related diseases including, but not limited to malaria, human African trypanomiasis, babesiosis, Chagas disease, microsporidiosis, pneumocystosis, primary amoebic meningoenchephalitis, and toxoplasmosis.

b. Treatment of a Parasitic Disease: Identifying a Need for Treatment and Administering a Compound In various aspects, the invention relates to a method for the treatment of a parasitic disease comprising the steps of: a) identifying a mammal in need of treatment of a parasitic disease; and b) administering to the mammal an effective amount of at least one compound having a structure represented by a formula:

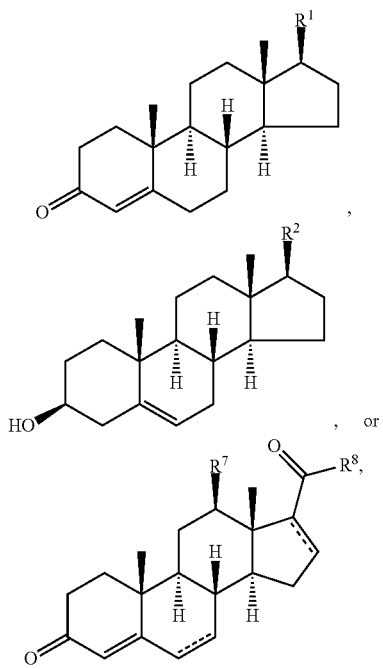

wherein each ---- is independently an optional covalent bond, wherein valence is satisfied; wherein $R^1$, when present, is selected from C1-C12 alkyl and C1-C12 alkenyl; wherein $R^2$, when present, is selected from C1-C12 alkyl and C1-C12 alkenyl; wherein $R^7$ is selected from hydrogen, hydroxyl, amino, and halogen; and wherein $R^8$ is selected from hydrogen and C1-C6 alkyl; or a pharmaceutically acceptable salt, solvate, or polymorph thereof.

In a further aspect, the mammal that the compound is administered to is a human. In a still further aspect, the mammal that the compound is administered to is a bovine. In a yet further aspect, the mammal that the compound is administered to is a canine.

In a further aspect, the identifying step is performed prior to the administering step. In a still further aspect, the mammal has been diagnosed with a parasitic disease prior to the administering step.

In a further aspect, the effective amount is a prophylatically effective amount. In a still further aspect, the effective amount is a therapeutically effective amount.

c. Treating a Parasitic Disease in a Cell

In one aspect, the invention relates to a method for treating a parasitic disease, the method comprising the step of contacting a mammalian cell with an effective amount of at least one compound having a structure represented by a formula:

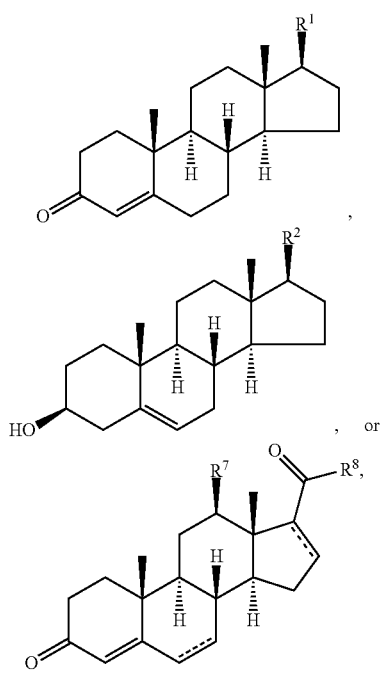

wherein each ---- is independently an optional covalent bond, wherein valence is satisfied; wherein $R^1$, when present, is selected from C1-C12 alkyl and C1-C12 alkenyl; wherein $R^2$, when present, is selected from C1-C12 alkyl and C1-C12 alkenyl; wherein $R^7$ is selected from hydrogen, hydroxyl, amino, and halogen; and wherein $R^8$ is selected from hydrogen and C1-C6 alkyl; or a pharmaceutically acceptable salt, solvate, or polymorph thereof.

In a further aspect, the invention relates to a method for treating a parasitic disease in at least one cell, comprising the step of contacting the at least one cell with an effective amount of at least one compound, or a pharmaceutically acceptable salt, hydrate, solvate, or polymorph thereof; wherein the compound is a disclosed compound or a product of a disclosed method of isolating a compound from *P. andrieuxii*.

In a further aspect, the invention relates to a method for treating a parasitic disease in a mammal by contacting at least one cell in a mammal, comprising the step of contacting the at least one cell with at least one disclosed compound or a product of a disclosed method of isolating a compound from *P. andrieuxii*, in an amount effective to inhibit growth of the parasite in the at least one cell.

In a further aspect, the effective amount is an amount sufficient to inhibit replication of the parasite. In a still further aspect, the effective amount is an amount sufficient to inhibit proliferation of the parasite. In a yet further aspect, the effective amount is an amount sufficient to be cytostatic to the parasite. In an even further aspect, the effective amount is an amount sufficient to kill the parasite.

In a further aspect, the cell is human. In a still further aspect, the cell is bovine. In a yet further aspect, the cell is canine.

In a further aspect, the cell has been isolated from a mammal prior to the contacting step. In a still further aspect, the contacting is via administration to the mammal.

In a further aspect, an effective amount is a therapeutically effective amount. In a yet further aspect, an effective amount is a prophylatically effective amount. In an even further aspect, treatment is symptom amelioration or prevention, and wherein an effective amount is a prophylatically effective amount.

In a further aspect, contacting is via administration to a mammal. In a still further aspect, the mammal has been diagnosed with a need for inhibiting parasitic activity prior to the administering step. In a yet further aspect, the mammal has been diagnosed with a parasitic infection prior to the administering step. In an even further aspect, the mammal has been diagnosed with a need for inhibiting parasitic replication prior to the administering step. In a still further aspect, the mammal has been diagnosed with a need for inhibiting parasitic proliferation prior to the administering step. In a yet further aspect, the mammal has been diagnosed with a need for a cytostatic effect on parasite prior to the administering step. In a further aspect, the mammal has been diagnosed with a need for treatment of a parasitic disease prior to the administering step.

In one aspect, the parasitic disease is leishmaniasis and related diseases including, but not limited to malaria, human African trypanomiasis, babcsiosis, Chagas disease, microsporidiosis, pneumocystosis, primary amoebic meningoenchephalitis, and toxoplasmosis 2. Manufacture of a Medicament In one aspect, the invention relates to a method for the manufacture of a medicament for treating a parasitic disease in a mammal comprising combining a therapeutically effective amount of a disclosed compound or a product of a disclosed method of isolating a compound from *P. andrieuxii* with a pharmaceutically acceptable carrier or diluent.

In various aspect, the invention relates methods for the manufacture of a medicament for treatment of a parasitic disease (e.g., treatment of leishmaniasis and related diseases including, but not limited to malaria, human African trypanomiasis, babesiosis, Chagas disease, microsporidiosis, pneumocystosis, primary amoebic meningoenchephalitis, and toxoplasmosis) in mammals (e.g., humans) comprising combining one or more disclosed compounds, products, or compositions or a pharmaceutically acceptable salt, solvate, hydrate, or polymorph thereof, with a pharmaceutically acceptable carrier. It is understood that the disclosed methods can be performed with the disclosed compounds, products, and pharmaceutical compositions. It is also understood that the disclosed methods can be employed in connection with the disclosed methods of using.

3. Use of Compounds

In one aspect, the invention relates to the use of a disclosed compound or a product of a disclosed method of isolating a compound from *P. andrieuxii*. In a further aspect, the use relates to the manufacture of a medicament for the treatment of a parasitic disease. In a further aspect, the parasitic disease is leishmaniasis and related diseases including, but not limited to malaria, human African trypanomiasis, babesiosis, Chagas disease, microsporidiosis, pneumocystosis, primary amoebic meningoenchephalitis, and toxoplasmosis. In a further aspect, a use relates to treatment of leishmaniasis and related diseases including, but not limited to malaria, human African trypanomiasis, babesiosis, Chagas disease, microsporidiosis, pneumocystosis, primary amoebic meningoenchephalitis, and toxoplasmosisin a mammal. In a further aspect, a use relates to treatment of a parasitic disease in a cell.

In one aspect, a use is treatment of leishmaniasis and related diseases including, but not limited to malaria, human African trypanomiasis, babesiosis, Chagas disease, microsporidiosis, pneumocystosis, primary amoebic meningoenchephalitis, and toxoplasmosis.

In one aspect, the invention relates to the use of a disclosed compound or a product of a disclosed method of isolating a compound from *P. andrieuxii* in the manufacture of a medicament for the treatment in a mammal of leishmaniasis and related diseases including, but not limited to malaria, human African trypanomiasis, babesiosis, Chagas disease, microsporidiosis, pneumocystosis, primary amoebic meningoenchephalitis, and toxoplasmosis.

In one aspect, the invention relates to the use of a disclosed compound or a product of a disclosed method of isolating a compound from *P. andrieuxii*, or a pharmaceutically acceptable salt, solvate, or polymorph thereof, or a pharmaceutical composition for use in treating or preventing leishmaniasis and related diseases including, but not limited to malaria, human African trypanomiasis, babesiosis, Chagas disease, microsporidiosis, pneumocystosis, primary amoebic meningoenchephalitis, and toxoplasmosis.

In one aspect, the invention relates to the use of a disclosed compound or a product of a disclosed method of isolating a compound from *P. andrieuxii*, or a pharmaceutically acceptable salt, solvate, or polymorph thereof, or a pharmaceutical composition, in combination with an additional pharmaceutical agent for use in the treatment of leishmaniasis and related diseases including, but not limited to malaria, human African trypanomiasis, babesiosis, Chagas disease, microsporidiosis, pneumocystosis, primary amoebic meningoenchephalitis, and toxoplasmosis.

In one aspect, the invention relates to a process for preparing a pharmaceutical composition comprising a therapeutically effective amount of a disclosed compound or a product of a disclosed method of isolating a compound from *P. andrieuxii*, or a pharmaceutically acceptable salt, solvate, or polymorph thereof, characterized in that a pharmaceutically acceptable carrier is intimately mixed with a therapeutically effective amount of the compound or the product of a disclosed method of making.

In a further aspect, the invention relates to a process for preparing a pharmaceutical composition comprising a therapeutically effective amount of a disclosed compound or a product of a disclosed method of isolating a compound from *P. andrieuxii*, or a pharmaceutically acceptable salt, solvate, or polymorph thereof, for use as a medicament.

4. Kits

In one aspect, the invention relates to a kit comprising at least one compound represented by a formula:

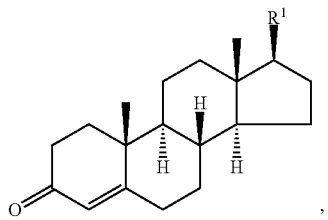

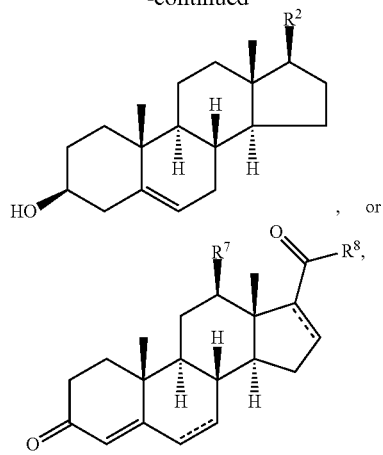

wherein each ---- is independently an optional covalent bond, wherein valence is satisfied; wherein $R^1$, when present, is selected from C1-C12 alkyl and C1-C12 alkenyl; wherein $R^2$, when present, is selected from C1-C12 alkyl and C1-C12 alkenyl; wherein $R^7$ is selected from hydrogen, hydroxyl, amino, and halogen; and wherein $R^8$ is selected from hydrogen and C1-C6 alkyl; or a pharmaceutically acceptable salt, solvate, or polymorph thereof, and one or more of: a) at least one agent known to increase the likelihood of a parasitic disease in a mammal; b) at least one agent known to decrease the likelihood of a parasitic disease in a mammal; c) at least one agent known to treat a parasitic disease in a mammal; or d) instructions for treating a parasitic disease.

In a further aspect, the at least one compound and the at least one agent are co-formulated.

In a further aspect, the at least one compound and the at least one agent are co-packaged.

In a further aspect, the at least one agent of the kit is selected from pentavalent antimonial, pentamidine, amphotericin B, allopurinol, ketaconazole, suramin, melarsoprol, paramomycin, miltefosine, sitamaquine, imiquimod, eflornitine, nifurtimox, benznidazole, crystal violet, amiodarone, ethidium, isomethamidium, and berenil. In a still further aspect, the at least one agent of the kit is selected from eflornitine, ethidium, isomethamidium, and berenil. In a yet further aspect, the at least one agent of the kit is selected from sodium stibogluoconate and meglumine antimoniate. In an even further aspect, the at least one agent of the kit is a pentavalent antimonial. In a still further aspect, the at least one agent of the kit is a pentavalent antimonial selected from is sodium stibogluoconate and meglumine antimoniate. In a yet further aspect, the at least one agent of the kit is a pentavalent antimonial, wherein the pentavalent antimonial is meglumine antimoniate. In a still further aspect, the at least one agent of the kit is amphotericin B. In a yet further aspect, the at least one agent of the kit is pentamidine. In an even further aspect, the at least one agent of the kit is miltefosine.

The kits of the present invention can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

5. Non-Medical Uses

Also provided are the uses of the disclosed compounds and products as pharmacological tools in the development and standardization of in vitro and in vivo test systems for the evaluation of the effects of a hemoflagellated protozoa activity in laboratory animals such as cats, dogs, rabbits, monkeys, rats and mice, as part of the search for new therapeutic agents for the treatment of a with a hemoflagellated protozoa infection, e.g. *Leishmania* spp. or *Trypanosoma* spp.

G. REFERENCES

PubMed Health; Diseases and Conditions. *Leishmaniasis*. (2009) www.ncbi.nlm.nih.gov/pubmedhealth/PMH0002362

Centers for Disease Control and Prevention (CDC). *Parasites—Leishmaniasis*. (2010) www.cdc.gov/parasites/leishmaniasis/disease.html Hotez, P. J.; Fenwick, A.; Savioli, L.; Molyneux, D. H. *Lancet* 2009, 373, 1570.

Liese, B.; Rosenberg, M.; Schratz, A. *Lancet* 2010, 375, 67.

Conteh, L.; Engels, T.; Molyneux, D. H. *Lancet* 2010, 375, 239.

Trouiller, P.; Olliaro, P.; Torreele, E.; Orbinski, J.; Laing, R.; Ford, N. *Lancet* 2002, 359, 2188.

Yamey, G.; Torreele, E. *Br. Med. J.* 2002, 325, 176.

Toreele, E.; Usdin, M.; Chirac, P. A *Needs-based Pharmaceutical R&D Agenda for Neglected Diseases*; World Health Organization: Geneva, 2004.

Hotez, P.; Ottesen, E.; Fenwick, A.; Molyneux, D. *Adv. Exp. Med. Biol.* 2006, 582, 23.

Hotez, P. J.; Molyneux, D. H.; Fenwick, A.; Kumaresan, J.; Sachs, S. E.; Sachs, J. D.; Savioli, L. *N. Engl. J. Med.* 2007, 357, 1018.

Pulido, M. T.; Serralta, L. Centro de Investigaciones de Quintana Roo: Chetumal, Quintana Roo, Mexico, 1993, 6.

Argüeta, A.; Cano, L.; Rodarte, M. Instituto Naeional Indigenista: Mexico, D. F., 2, 204.

Jiu, J. *Lloydia* 1966, 29, 250.

Lezama-Davila, C. M.; Isaac-Marquez, A. P. Muell.-Arg. *Divulg. Bioméd.*, 1994, 2, 13.

Chan-Bacab, M. J.; Balanza, E.; Deharo, E.; Muñoz, V.; Durán-Garcia, R.; Peña-Rodriguez, L. M. *Journal of Ethnopharmacology* 2003, 86, 243.

Lezama-Davila, C. M.; Isaac-Marquez, A. P.; Zamora-Crescencio, P.; Úc-Encalada, M. R.; Justiniano-Apolinar, S. Y.; Angel-Robles, R.; Satoskar, A.; Hernández-Rivero, L. *Fitoterapia* 2007, 78, 255.

Yam-Puc, A.; Escalante-Erosa, F.; Pech-López, M.; Chan-Bacab, M. J.; Arunachalampillai, A.; Wendt, O. F.; Sterner, O.; Peña-Rodriguez, L. M. *J. Nat. Prod.* 2009, 72, 745.

Kuroda, M.; Kubo, S.; Uchida, S.; Sakagami, H.; Mimaki, Y. *Steroids* 2010, 75, 83.

Delgado, G., Puentes, F., Moreno, A., Patarroyo M. E. *Pharmacological Research* 2001, 44, 281.

Sheikh, Y. M.; Djerassi, C. *Tetrahedron* 1974, 30, 4095.

Kontiza, I.; Abatis, D.; Malakate, K.; Vagias, C.; Roussis, V. *Steroids* 2006, 71, 177.

Cabrera, G.; Palermo, J. A.; Seldes, A. M.; Gros, E. G.; Oberti, J. C. *Phytochemistry* 1991, 30, 1239.

Yan, S.-J.; Su, J.-Y.; Zeng, L.-M.; Liu, L.-J.; Wang, Y.-H. *Redai Haiyang Xuebao* 2002, 21, 92.

Seo, S.; Yoshimura, Y.; Satoh, T.; Uomori, A.; Takeda, K. *Journal of the Chemical Societ, Perkin Transactions* 1 1986, 411.

Anastasia, M.; Allevi, P.; Ciuffreda, P.; Fiecchi, A.; Gariboldi, P.; Scala, A. *Journal of the Chemical Society, Perkin Transactions* 1 1985, 595.

McCarthy, F. O.; Chopra, J.; Ford, A.; Hogan, S. A.; Kerry, J. P.; O'Brien, N. M.; Ryan, E.; Maguire, A. R. *Organic and Biomolecular Chemistry* 2005, 3, 3059.

Cui, J.-G.; Fan, L.; Huang, L.-L.; Liu, H.-L.; Zhou, A.-M. *Steroids* 2009, 74, 62.

Schun, Y.; Cordell, G. A. *Journal of Natural Products* 1987, 50, 195.

Bai, L.; Wang, L.; Zhao, M.; Toki, A.; Hasegawa, T.; Ogura, H.; Kataoka, T.; Hirose, K.; Sakai, J.; Bai, J.; Ando, M. *Journal of Natural Products* 2007, 70, 14.

de Melo Cazal, C.; de Cássia Domingues, V.; Batalhão, J. R.; Corrêa Bueno, O.; Rodrigues Filho, E.; da Silva, M. F. G. F.; Cezar Vieira, P.; Fernandes, J. B. *J. Chromatography A* 2009, 1216, 4307.

Seo, S.; Tomita, Y.; Tori, K. *Tetrahedron Letters* 1975, 16, 7.

Gawronski, J. K. *Tetrahedron* 1982, 38, 3.

Zhao, M.; Bai, L.; Wang, L.; Toki, A.; Hasegawa, T.; Kikuchi, M.; Abe, M.; Sakai, J.-I.; Hasegawa, R.; Bai, Y.; Mitsui, T.; Ogura, H.; Kataoka, T.; Oka, S.; Tsushima, H.; Kiuchi, M.; Hirose, K.; Tomida, A.; Tsuruo, T.; Ando, M. *Journal of Natural Products* 2007, 70, 1098.

Kennard, O.; Fawcett, J. K.; Watson, D. G.; Kerr, K. Ann; Stöckel, K.; Stocklin, W.; Reichstein, T. *Tetrahedron Letters*. 1968, 35, 3799.

Lavault, M.; Richomme, P.; Bruneton, J. *Fitoterapia* 1999, 70, 216.

Chen, H.; Xu, N.; Zhou, Y.; Qiao, L.; Cao, J.; Yao, Y.; Hua, H.; Pei, Y. *Steroids* 2008, 73, 629.

Plaza, A.; Bifulco, G.; Hamed, A. I.; Pizza, C.; Piacente, S. *Tetrahedron Letters* 2003, 44, 8553.

Plaza, A.; Perrone, A.; Balestrieri, C.; Balestrieri, M. L.; Bifulco, G.; Carbone, V.; Hamed, A. I.; Pizza, C.; Piacente, S. *Tetrahedron* 2005, 61, 7470.

Perrone, A.; Plaza, A.; Ercolino, S. F.; Hamed, A. I.; Parente, L.; Pizza, C.; Piacente, S. *Journal of Natural Products* 2006, 69, 50.

Perrone, A.; Plaza, A.; Hamed, A. I.; Pizza, C.; Piacente, S. *Current Organic Chemistry* 2008, 12, 1648.

Niero, R.; Calixto, J. B.; Dias de Silva Filho, J.; Yunes, R. A.; Santana, A. E. G. *Natural Product Letters* 1999, 13, 63.

Yunes, R. A.; Brum, R. L.; Calixto, J. B.; Rimpler, H. *Phytochemistry* 1993, 34, 787.

Niero, R.; Alves, R. V.; Cechinel Filho, V.; Calixto, J. B.; Hawkes, J. E.; Sant'Ana, A. E. G.; Yunes, R. A. *Planta Medica* 2002, 68, 850.

de Souza, W.; Rodrigues, J. C. F. Interdisciplinary Perspectives on Infectious Diseases 2009, doi: 10.1155/2009/642502.

Werbovetz, K. A. Expert Opinion on Theropeutic Targets. 2002, 6, 407.

Haughan, P. A.; Chance, M. L.; Goad, L. J. *Biochemical Journal* 1995, 308, 31.

Magaraci, F.; Jimenez, C. J.; Rodrigues, C.; Rodrigues, J. C.; Braga, M. V.; Yardley, V.; de Luca-Fradley, K.; Croft, S. L.; de Souza, W.; Ruiz-Perez, L. M.; Urbina, J.; Gonzalez, J. *Journal of Medicinal Chemistry* 2003, 46, 4714.

Bazin, M.-A.; Loiseau, P. M.; Bories, C.; Letourneux, Y.; Rault, S.; El Kihel, L. *European Journal of Medicinal Chemistry* 2006, 41, 1109.

Sartorelli, P.; Andrade, S. P.; Melhem, M. S. C.; Prado, F. O.; Tempone, A. G. *Phytotherapy Reserch* 2007, 21, 644.

H. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

The following exemplary compounds of the invention were synthesized. The Examples are provided herein to illustrate the invention, and should not be construed as limiting the invention in any way. The Examples are typically depicted in free base form, according to the IUPAC naming convention. However, some of the Examples were obtained or isolated in salt form.

1. General Methods

Optical rotations were obtained on a Perkin-Elmer 343 automatic polarimeter. UV spectra were measured with a Perkin-Elmer Lambda 10 UV/vis spectrometer. IR spectra were run on a Thermo Scientific Nicolet 6700 FT-IR spectrometer. NMR spectroscopic data were obtained on a Bruker Avance DRX-400 or 600 MHz spectrometer (with TMS as an internal standard). Column chromatography was performed with 65-250 or 230-400 mesh silica gel (Sorbent Technologies, Atlanta, Ga.). Analytical thin-layer chromatography was conducted on precoated 250 µm thickness silica gel plates ($UV_{254}$, glass backed, Sorbent Technologies, Atlanta, Ga.), and preparative thin-layer chromatography was performed on precoated 20 cm×20 cm, 500 µm thickness silica gel plates ($UV_{254}$, glass backed, Sorbent Technologies, Atlanta, Ga.). Analytical HPLC was conducted on a 150 mm×4.6 mm i.d. Sunfire $PrepC_{18}$ column (Waters, Milford, Mass.), and semi-preparative HPLC was conducted on a 150 mm×10 mm i.d. or a 150 mm×19 mm i.d., 5 µm Sunfire $PrepC_{18}$ column (Waters, Milford, Mass.), along with a Waters system equipped with a 600 controller, a 717 Plus autosampler, and a 2487 dual wavelength absorbance detector. Electron micrographs were generated on JEOL JEM-1400 TEM (JEOL, Ltd. Tokyo, Japan), operating at 80K equipped with a Veleta digital camera (Olympus Soft Imaging Solutions GmbH, Munster, Germany).

2. Isolation of Compounds from *Pentalinon Andrieuxii* a. Harvesting of Plant Material.

The roots of *P. andrieuxii* Mueller-Argoviensis (syn. *Urechites andrieuxii*, Apocynaceae; hereinafter "*P. andrieuxii*") were collected from a region of riparian forest at coordinates 96° 16'N 90° 36W in Campeche, Mexico (muncipalities of Campeche and Escarcega) located in the Yucatan Peninsula of Mexico. The plant was identified in the Herbarium of the Autonomous University of Campeche (Universidad Autonoma de Campeche; UACAM), Campeche, Mexico, under voucher no. 6921 (Zamora-Crescencio & Lezama-Davila) and in the Herbarium of the Autonomous University of Yucatan (Universidad Autonoma de Yucatan), Mexico, under voucher no. 1 (Viscencio de la Rosa & Lezama-Davila). The collection and positive identification of this plant was supervised by the Director of the Herbarium of UACAM.

b. Extraction and Isolation of Compounds from Roots.

Figure 2:
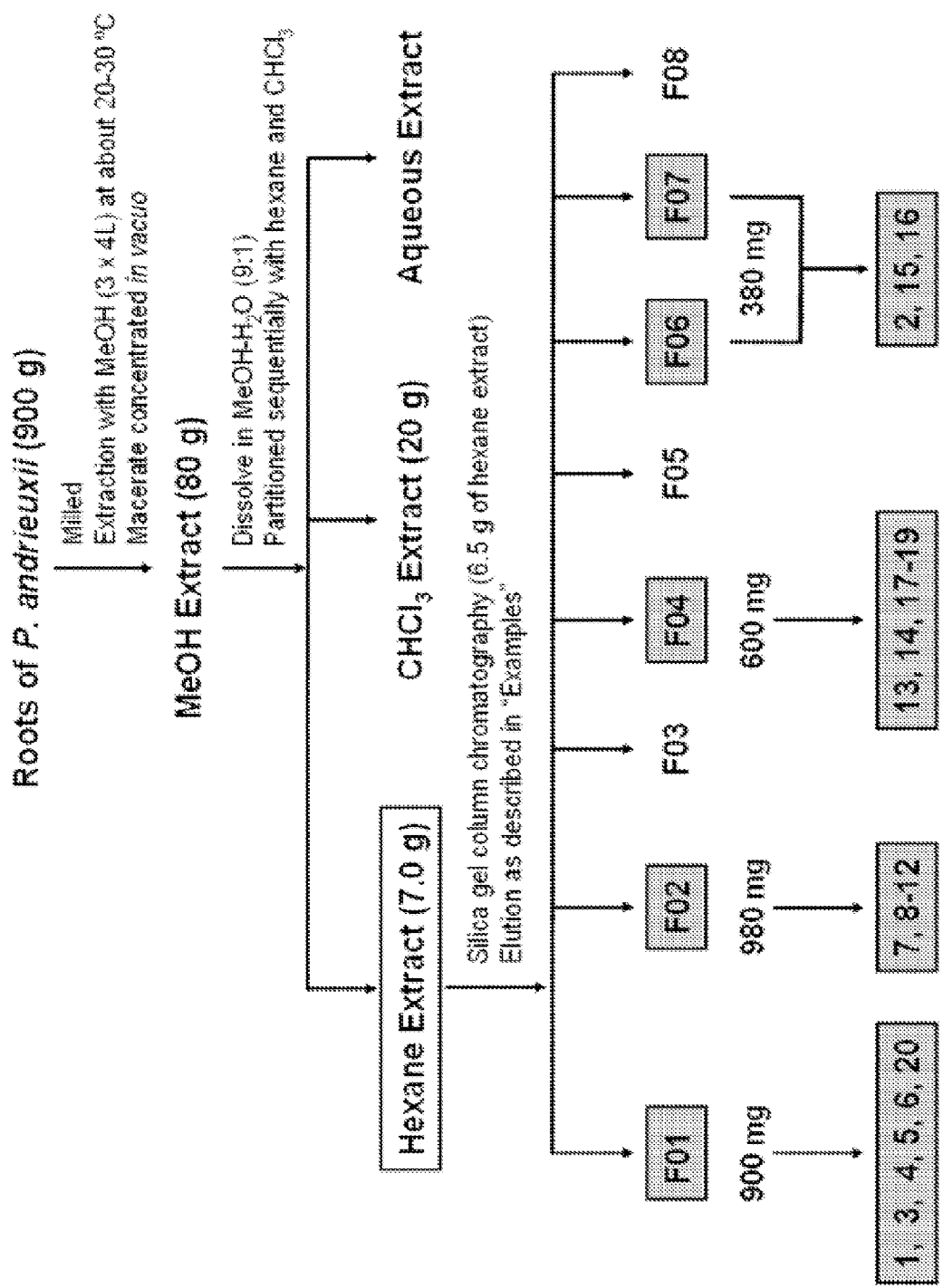
FIG. 2 shows a schematic illustrating the biologically guided extraction and isolation methods used to produce the leishmanicidal products.

The air-dried roots of *P. andrieuxii* (900 g) were milled and then extracted with methanol overnight at room temperature (3×4 L). The macerate was concentrated in vacuo (80 g) and partitioned to afford a hexane-soluble extract (7.0 g), and a $CHCl_3$-soluble extraction (20 g). The hexane-soluble extract was found to be active against promastigotes of *L. mexicana* ($IC_{50}$=35 µg/mL). Part of the hexane-soluble partition (6.5 g) was subjected to separation over a silica gel column using pure hexane initially, followed in turn by a gradient of increasing polarity using hexane-ethyl acetate and pure acetone to yield eight pooled fractions (F01-F08). FIG. 2 provides a schematic representation of the biologically guided extraction and isolation methods used to produce the leishmanicidal products from *Pentalinon andriuxii*.

Fraction F01 (900 mg) was chromatographed by passage over a fine silica gel (3.0×45 cm) column using a gradient solvent of hexane-EtOAc, with nine pooled fractions obtained (F01F1-F01F9). TLC detection showed that fraction F01F03 (120 mg) to contain compounds with similar TLC behavior to terpenoids or steroids. This fraction was further purified repeatedly by HPLC on a semi-preparative RP18 column (150 mm×10 mm i.d.), using $MeOH$—$H_2O$ (95:5; 5 mL/min) as the mobile phase, to yield compounds 1 (1.2 mg, $t_R$=11.2 min), 3 (4.0 mg, $t_R$=16.7 min), 4 (2.0 mg, $t_R$=19.2 min), 5 (6.0 mg, $t_R$=22.3 min), and 6 (8.0 mg, $t_R$=25.2 min).

Fraction F02 (980 mg) was subjected to separation over a silica gel column and eluted with a hexane-EtOAc gradient solvent system. Of the subfractions obtained, F0203 was determined by TLC to be a sterol-rich fraction, and was further chromatographed on a semi-preparative RP18 column (150 mm×10 mm i.d.) by HPLC using $MeOH$—$H_2O$ (90:10; 5 mL/min) as the solvent system, to yield compounds 20 (4.0 mg, $t_R$=7.2 min), 7 (4.0 mg, $t_R$=12.0 min), 8 (6.0 mg, $t_R$=15.7 min), 9 (6.0 mg, $t_R$=17.8 min), 10 (2.0 mg, $t_R$=20.2 min), 11 (4.0 mg, $t_R$=21.7 min), and 12 (24.0 mg, $t_R$=27.4 min). Compound 17 (2.0 mg) was purified from subfraction F0202 by repeated chromatography on silica gel columns, using hexane-acetone as eluent.

Fractions F06 and F07 were combined (380 mg) and chromatographed on a silica gel column and eluted with a $CH_2Cl_2$-acetone gradient solvent system (30:1 to pure acetone) to yield 14 subfractions. Compound 2 (5.0 mg) was purified from subfraction F06F12 by repeated chromatography using silica gel columns with $CH_2Cl_2$-acetone gradient solvent system (15:1 to 4:1). Subfraction F06F03 was chromatographed on a semi-preparative RP18 column (150 mm×10 mm i.d.) by HPLC using $CH_3CN$—$H_2O$ (35:65; 5 mL/min) as mobile phase, to give compounds 15 (1.0 mg, $t_R$=13.6 min), and 16 (0.8 mg, $t_R$=15.8 min).

In order to find certain common flavonoids or coumarins as potential marker compounds to provide a basis for extract standardization, fraction F04, which was found to be rich in compounds showing a fluorescence under UV light at 365 nm on TLC plates, was also investigated. Compounds 14 (1.5 mg, $t_R$=17.2 min) and 13 (4.0 mg, $t_R$=19.5 min) were purified from a less polar subfraction of F04 by preparative HPLC on a semi-preparative RP18 column (150 mm×10 mm i.d.), using MeOH—H$_2$O (92:8, 5 mL/min) as eluting solvent. Compounds 18 (3.0 mg, t$_R$=6.9 min) and 19 (2.0 mg, t$_R$=8.1 min) were purified from the more polar subfraction F04 by preparative HPLC on a semi-preparative RP18 column (150 mm×10 mm i.d.), using MeOH—H$_2$O (70:30, 5 mL/min) as the eluting solvent.

c. Extraction and Isolation of Compounds from Stems.

The stems of P. andrieuxii were also processed with a similar extraction and isolation method used for the roots (see above and FIG. 2 for description of root extraction procedure). Nine compounds (Table 3) were isolated and identified from pooled subfractions (PASD3F2, PASD3F3 and PASD3F4) of a CHCl$_3$-soluble extract (PASD3) of the stem of P. antrieuxii. The activity of the organic partition samples isolated from the stem of are shown below in Table 1. The activity is the IC50 determined in the promastigote assay described below.

TABLE 1

| Stem Fraction | Promastigote IC$_{50}$ (µg/mL) |
| --- | --- |
| PASD3F1 | 768 |
| PASD3F2 | 21.5 |
| PASD3F3 | 22.0 |
| PASD3F4 | 37.0 |
| PASD3F5 | 178 |
| PASD3F6 | 703 |
| PASD3F7 | 700 |

3. Structure Elucidation of Isolated Compounds

The hexane-soluble extract of P. andrieuxii led to the isolation, identification, structural elucidation and biological characterization of 16 sterol derivatives (1-16), as well as three coumarins (17-19), and a triterpenoid (20). Among these compounds, 1 was determined to be a novel cholestane derivative, and 2 a novel sterol glycoside bearing a rare polyoxygenated 14,15-secopregane skeleton. The structures of these two novel compounds were elucidated based on the analysis of their physical and spectroscopic data ([α]$_D$, CD, $^1$H NMR, $^{13}$C NMR, DEPT, 2D-NMR, and HRESIMS). The remaining compounds isolated were identified as 24-methylcholesta-4,24(28)-dien-3-one (3), cholest-4-en-3-one (4), stigmast-4,22-dien-3-one (5), stigmast-4-en-3-one (6), cholest-5,20,24-trien-3β-ol (7), cholest-5,24-dien-3β-ol (demosterol, 8), 24-methylcholest-5,24(28)-dien-3β-ol (9), cholesterol (10), isofucosterol (11), β-sitosterol (12), 7-ketositosterol (13), 7-ketostigmasterol (14), 6,7-dihydroneridienone (15), neridienone (16), serborosin (17), xanthoxyletin (18), xanthyletin (19), and oleanolic acid 3-acetate (20), using comparison of their physical and spectroscopic data with published values. Table 2 below lists the specific compound isolated from the root of P. antrieuxii.

TABLE 2

| Compound Number | Structure |
| --- | --- |
| 1 | |

TABLE 2-continued

| Compound Number | Structure |
| --- | --- |
| 2 | |
| 3 | |
| 4 | |
| 5 | |
| 6 | |
| 7 | |

TABLE 2-continued

| Compound Number | Stucture |
|---|---|
| 8 | |
| 9 | |
| 10 | |
| 11 | |
| 12 | |
| 13 | |
| 14 | |
| 15 | |
| 16 | |
| 17 | |
| 18 | |
| 19 | |

TABLE 2-continued

| Compound Number | Structure |
|---|---|
| 20 | 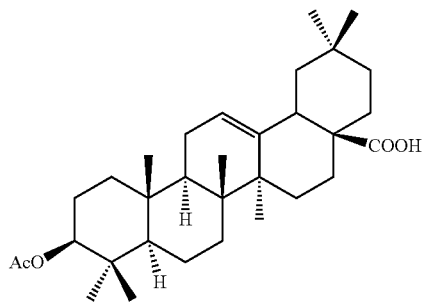 |

Nine compounds (Table 3) were isolated and identified from pooled active subfractions (PASD3F2, PASD3F3 and PASD3F4) of a CHCl$_3$-soluble extract (PASD3) of the stem of *P. antrieuxii*. The structures of these compounds were elucidated as pentalinonoside (2, novel compound, also found from root extract), 6,7-dihydroneridienone A (15), neridienone A (16), cybisterol (21), 12β-hydroxypregn-4-ene-3,20-dione (22), fraxidin (23), fraxetol (fratexin, 24), betulinic acid (25), and (+)-pinoresinol (26). Table 4 below lists the specific compound isolated from the stem of *P. antrieuxii*.

TABLE 3

| Compound Number | Structure |
|---|---|
| 2 | 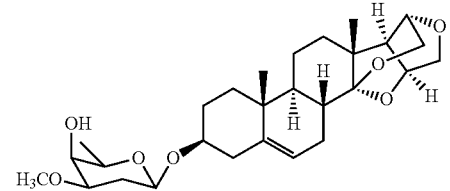 |
| 15 | 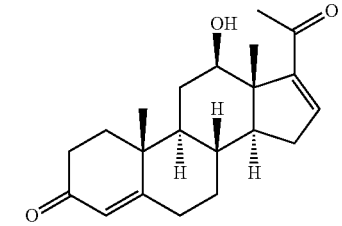 |
| 16 | 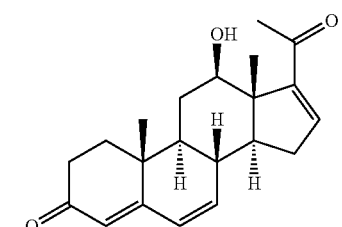 |
| 21 | 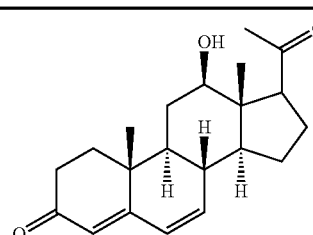 |
| 22 | 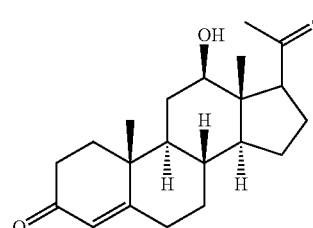 |
| 23 | 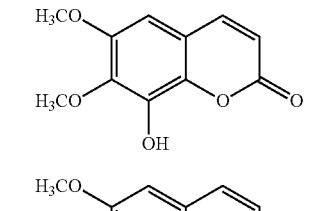 |
| 24 | 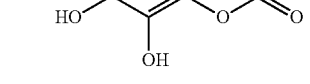 |
| 25 | 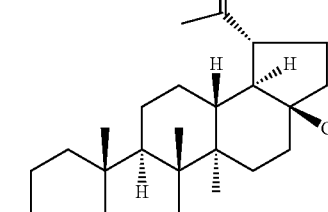 |
| 26 | 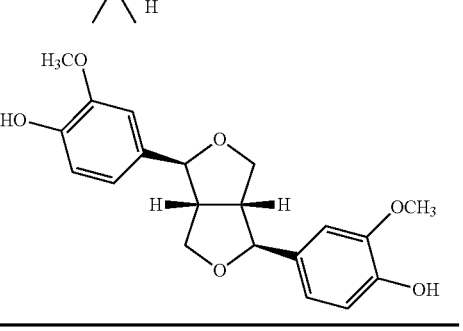 |

4. Structure Elucidation of Novel Compounds

Compound 1 was obtained as a colorless gum. The molecular formula was assigned as $C_{27}H_{40}O$, based on the ion peak at m/z 381.3154 [M+H]$^1$ (calcd for $C_{27}H_{41}O$ for $C_{27}H_{41}O$, 381.3157) in the HRESIMS. The typical IR absorptions supported the presence of methyl (2953 and 2873 cm$^{-1}$), methylene (2925 and 2852 cm$^{-1}$), ketone (1733 cm$^{-1}$), and double bond (1676 cm$^{-1}$) moieties. The UV maximum at 239 nm (log ε 3.99) suggested the presence of an α,β-unsaturated ketone group. The $^1$H NMR spectroscopic data of 1 (Table 2) showed two characteristic broad singlets at $δ_H$ 4.80 (1H) and 4.89 (1H), consistent with the presence of a vinylic group. A singlet at $δ_H$ 5.73 (1H, H-4) and a broad triplet at 5.11 (1H, br t, J=7.0 Hz, H-24) indicated the occurrence of two trisubstituted double bonds. In the high-field region, proton signals of two tertiary methyl groups at $δ_H$ 0.62 (3H, s, H-18) and 1.18 (3H, s, H-19), together with signals of two tertiary methyl groups linked to the double bond at $δ_H$ 1.61 (3H, s, H-26) and 1.69 (3H, s, H-27), could be recognized. Besides these methyl group protons, the highly overlapped signals distributed in the high field region from 0.8 to 2.4 ppm suggested the presence of a group of alkyl methylene and methine signals. Consistent with the $^1$H NMR data, the $^{13}$C NMR spectroscopic data of 1, which were sorted using DEPT and HSQC spectra, showed signals of a vinylic group at $δ_C$ 149.4 (C-20) and 110.1 (C-21), two trisubstituted double bonds at $δ_C$ 124.2 (C-4), 172.0 (C-5), 124.7 (C-24), and 131.3 (C-25), and four methyl carbons at $δ_C$ 13.3 (C-18), 17.8 (C-19 and C-26), and 26.2 (C-27). Furthermore, the other carbon signals in the $^{13}$C NMR spectrum could be classified into ten methylene carbons, four methine carbons, two quaternary carbons, and a ketone group. The NMR information combined with the molecular formula obtained from the HRESIMS, suggests that compound 1 is a cholestane steroid with an α,β-unsaturated ketone feature within the tetracyclic ring system and two double bonds in the side chain. In the HMBC spectrum of 1, correlations from H-4 to C-6 and C-10, and from H$_3$-19 to C-1, C-5, and C-9, confirmed the 3-keto-4-ene functionality of the A ring. The key HMBC correlations of the vinylic protons (H-21) with C-17 and C-22, H$_3$-26 and H$_3$-27 with C-24 and C-25, led to the placement of the two double bonds at C-20 and C-24 of the side chain, respectively (FIG. 3). Observed key NOE effects of H-8/H$_3$-19, H-8/H$_3$-18, H-14/H-9, H-14/H-17, and H-21/H-18 were used to establish the relative configuration of compound 1. The absolute configuration of 1 was determined from the CD spectrum, and 1 showed a weak negative band around 317 nm (Δε=−1.44), corresponding to an α,β-unsaturated carbonyl n-π* excitation, and an intensive positive band around 238 nm (Δε=+7.14), representing a π-π* transition. These observed Cotton effects were very similar to those of the known compound, (8S,9S,10R,13R,14S,17R,20R)-cholest-4-en-3-one. Thus, the structure of the new compound 1 was proposed as (8S,9S,10R,13R,14S,17R)-cholest-4,20,24-trien-3-one, and was accorded the trivial name, pentalinonsterol.

The specific characterization data of pentalinonsterol (1): colorless gum; [α]$^{20}_D$ +56.0 (c 0.1, CH$_2$Cl$_2$); UV (MeOH) λ$_{max}$ (log ε) 239 (3.99), 316 (0.90) nm; CD (c 1.31×10$^{-5}$ M, CH$_2$Cl$_2$/MeOH) λ$_{max}$ (Δε) 238 (+7.14), 317 (−1.44) nm; IR (film) ν$_{max}$ 2952, 2925, 2873, 2852, 1733, 1676, 1456, 1376, 1230, 1170 cm$^{-1}$; $^1$H NMR (400 MHz, CDCl$_3$) and $^{13}$C NMR (100 MHz, CDCl$_3$) data, see Table 2; HRESIMS m/z m/z 381.3154 [M+H]$^+$ (calcd for C$_{27}$H$_{41}$O, 381.3157).

Compound 2 was obtained as a colorless resin. The HRESIMS of 2 afforded a sodiated molecular ion peak at m/z 513.2817, corresponding to an elemental formula of C$_{28}$H$_{42}$O$_7$Na (calcd m/z 518.2828). The IR spectrum exhibited typical absorptions of hydroxy (3477 cm$^{-1}$), alkyl methyl (2949 and 2889 cm$^{-1}$), and methylene (2933 and 2870 cm$^{-1}$) moieties. In the UV spectrum, no obvious absorption was observed within the 200-400 nm region. In the $^1$H NMR spectrum of 2, a 2,6-deoxy sugar unit was evident from signals at $δ_H$ 4.84 (1H, dd, J=9.6, 2.0 Hz, H-1', the anomeric proton), 1.73 and 2.10 (each 1H, m, H-2'), 3.43 (1H, ddd, J=12.0, 5.0, 2.0 Hz, H-3'), 3.91 (1H, brs, H-4'), 3.60 (1H, q, J=6.5 Hz, H-5'), 1.55 (1H, d, J=6.5 Hz, H-6'), and 3.40 (3H, s, OCH$_3$-3'). The chemical shifts and the coupling pattern of these proton signals were found to be comparable with those of diagnose, and the large J value (9.6 Hz) of the anomeric proton indicated the β configuration of this 2,6-deoxyhexose sugar unit (Zhao et al., 2007; Kuroda et al., 2010). The corresponding $^{13}$C NMR data of this monosaccharide were observed at $δ_C$ 98.8 (C-1', anomeric carbon), 33.3 (C-2'), 79.3 (C-3'), 67.1 (C-4'), 71.5 (C-5'), 17.8 (C-6'), and 55.4 (OCH$_3$-3'). Besides the signals of the sugar unit, the $^1$H NMR spectrum also displayed signals of seven oxygenated protons at $δ_H$ 3.90 (1H, m, H-3), 4.02 (dd, J=10.0, 4.4 Hz, H$_a$-15), 4.23 (1H, d, J=10 Hz, H$_b$-15), 4.56 (1H, d, J=4.5 Hz, H-16), 4.49 (1H, ddd, J=7.7, 6.2, 1.5 Hz, H-20), 3.79 (dd, J=12.4, 1.3 Hz, H$_a$-21), 4.06 (dd, J=12.0, 6.0 Hz, H$_b$-21), and 4.02 (dd, J=10.0, 4.4 Hz, H$_a$-15), a signal for an olefinic proton at $δ_H$ 5.52 (1H, t, J=2.5 Hz, H-6), and the presence of two tertiary methyl groups at $δ_H$ 0.97 (3H, s, H-19) and 1.08 (3H, s, H-18), as well as a number of highly overlapped signals distributed in the high-field region from 0.8 to 2.4 ppm for alkyl methylenes and methines, all of which could be attributed to a highly oxygenated steroidal aglycone moiety. The 21 skeletal signals in the $^{13}$C NMR spectrum were classified by the DEPT and HSQC spectra into two methyls, six methylene groups, two alkyl methines, three quaternary alkyl carbons, six oxygenated carbons (including two primary, three secondary and one tertiary), and a trisubstituted double bond. This suggested that compound 2 is a 3-oxy-4-en-14,15-secopregnane derivative (Plaza et al., 2003 and 2005; Perrone et al, 2006 and 2008). In the COSY spectrum, the oxygenated methine proton at $δ_H$ 4.56 (1H, t, J=4.5 Hz, H-16) showed correlations with an alkyl methine proton at $δ_H$ 2.60 (1H, dd, J=7.6, 4.4 Hz, H-17) and one geminal proton of an oxygenated methylene at $δ_H$ 4.02 (1H, dd, J=10.0, 4.4 Hz, H$_a$-15). Another oxygenated methine proton at $δ_H$ 4.49 (1H, ddd, J=7.6, 6.0, 1.5 Hz, H-20) also showed correlations with H-17, and two geminal protons of an oxygenated methylene at $δ_H$ 4.06 (1H, dd, J=12.4, 6.0 Hz, H$_a$-21) and 3.79 (1H, d, J=12.4, 1.3 Hz, H$_b$-21), respectively. Thus, an important spin system including H-15, H$_2$-16, H-17, H-20 and H$_2$-21 in compound 2 was deduced as shown (FIG. 3). Furthermore, the key HMBC correlations from H-16, H-17 and H-21 to C-14, and from H-15 and H-16 to C-20, were used to construct a highly oxygenated unit. This unusual moiety in 2 involved the opening of the ring D of the pregnane skeleton between C-14 and C-15, and the connection through oxygen bridges of C-14 with C-16, C-15 with C-20, as well as C-21 with C-14 to generate a six-membered ring and two tetrahydrofuran rings with a ketal group on C-14.

The occurrence of 14,15-secopregnane derivatives with similar polyoxygenated features to 2 is rare in the plant kingdom, and other naturally occurring compounds of this class have been found from a limited number of plants such as species in the genera *Cynanchum* and *Solenostemma* of the family Asclepiadaceae, and the genus *Mandevilla* of the family Apocynaceae (Kennard et al., 1968; Lavault et al., 1999; Chen et al., 2008; Plaza et al., 2003 and 2005; Perrone et al, 2006 and 2008; Niero et al., 1999 and 2002; Yunes et al., 1993). These compounds are characterized by the cleavage of the D ring between C-14 and C-15, a hexahydrofuro[3,4-b]furan ring on ring C, with C-20 connected to C-14 or C-18 through an oxygen atom, to generate ketal groups at C-14 and/or C-20. A structurally unusual feature of compound 2 is that it exhibits for the first time a C-21 methyl group in the pregnane skeleton incorporated into two tetrohydrofuran rings to form a ketal; group at C-14. The relative configuration of 2 was deduced from a NOESY NMR experiment. The key NOE effects between H-17 with H-16 suggested a cis junction of the two tetrohydrofuran rings of the highly oxygenated ring system, and the NOE effects between H-18 with H-20 and H$_a$-21 indicated the n-orientation of the C-21 oxygenated methylene group. The relative configurations of the remaining portion of the aglycone were consistent with those of known pregnane steroids, based on an analysis of the NOE spectrum. The β position of the diginosyl group on C-3 was deduced by the NOE correlations of H-3 with H$_\alpha$-4 and H$_\alpha$-2. The configuration of the β-diginose unit was confirmed by NOE correlations between H-1'/H$_\alpha$-2', H-3', and H-5', H-4'/H-5, OCH$_3$-3'/H$_\beta$-2'. The sugar unit obtained by acid hydrolysis of compound 1 exhibited a positive optical rotation value, which demonstrated that the absolute configuration of the sugar is in the D form. Furthermore, an energy-minimized model generated by Chem3D Ultra 10.0 based on a presumed configuration matched well with all the observed NOESY correlations and served to explain the observed coupling patterns for H$_2$-15, H-16, H-17, H-20, and H$_2$-21 of the polyoxygenated ring system (FIG. 4). Thus, the structure of compound 2 (pentalinonside) was determined as 14,16-14,21-15,20-triepoxy-14,15-secopregnan-5-en-3-ol 3-O-β-D-diginopyranoside.

The specific characterization data of pentalinonside (2): colorless gum; $[\alpha]^{20}_D$ −30.0 (c 0.1, MeOH); UV (MeOH) end absorption; IR (film) $v_{max}$ 3477, 2949, 2933, 2889, 2870, 1640, 1460, 1381, 1258, 1168, 1098, 1067 1025, and 977 cm$^{-1}$; $^1$H NMR (400 MHz, CDCl$_3$) and $^{13}$C NMR (100 MHz, CDCl$_3$) data, see Table 2; HRESIMS m/z 513.2817m/z [M+Na]$^+$ (calcd for C$_{28}$H$_{42}$O$_7$Na, 518.2828).

For acid hydrolysis of compound 2, 2.0 mg dissolved in MeOH (0.8 mL) was added to 0.05 M H$_2$SO$_4$ (0.8 mL), and the solution was then heated at 70° C. for 3 h. The reaction mixture was neutralized by passage through a Dowex® 1×2 column (2.0×2.0 cm), and was then chromatographed on an ODS column (1.5×2.0 cm) with MeOH—H$_2$O (40:60 to 70:30) as eluent, to give diginose (0.2 mg). This 2,6-deoxyhexose sugar unit was assigned in the D-form based on its optical rotation value. D-diginose: $[\alpha]^{20}_D$+21.0 (0.02, 24 h after dissolution in H$_2$O) [lit. $[\alpha]^{27}_D$+16.4 (c 0.05, H$_2$O)].

$^1$H and $^{13}$C NMR data of compounds 1 and 2 is provided in Table 4. $^1$H NMR spectrum was measured at 400 MHz and $^{13}$C NMR was measured at 100 MHz. NMR data of 1 were obtained in CDCl$_3$ and the NMR data of 2 were obtained in pyrdine-d$_5$. Assignments are based on HSQC and HMBC NMR spectra. J values (Hz) are given in parentheses, and some geminal protons are indicated with the α- or β-orientation based on a NOESY experiment. Multiplicity was obtained from the DEPT spectra. For overlapped signals, only chemical shift values are given.

TABLE 4

| | Compound 1 | | Compound 2 | |
|---|---|---|---|---|
| position | $\delta_H$ (mult. J, Hz)$^b$ | $\delta_C$, mult.$^c$ | $\delta_H$ (mult. J, Hz)$^b$ | $\delta_C$, mult.$^c$ |
| 1 | 1.73$^d$ | 36.1, CH$_2$ | 1.05 α,$^d$ | 37.5, CH$_2$ |
|   | 2.02$^d$ |   | 1.75 β,$^d$ |   |
| 2 | 2.40$^d$ | 34.4, CH$_2$ | 2.13 α,$^d$ | 30.4, CH$_2$ |
|   |   |   | 1.68 β,$^d$ | 77.3, CH |
| 3 |   | 200.1, qC | 3.90,$^d$ | 39.4, CH$_2$ |

| | Compound 1 | | Compound 2 | |
|---|---|---|---|---|
| position | $\delta_H$ (mult. J, Hz)$^b$ | $\delta_C$, mult.$^c$ | $\delta_H$ (mult. J, Hz)$^b$ | $\delta_C$, mult.$^c$ |
| 4 | 5.73, s | 124.2, CH | 2.59 α,$^d$ | |
|   |   |   | 2.40 β,$^d$ | |
| 5 |   | 172.0, qC |   | 139.7, qC |
| 6 | 2.30$^d$ | 33.4, CH$_2$ | 5.52 t (2.5) | 122.6, CH |
|   | 2.40$^d$ |   |   |   |
| 7 | 1.02$^d$ | 32.4, CH$_2$ | 1.67$^d$ | 25.5, CH$_2$ |
|   | 1.84$^d$ |   | 2.50$^d$ |   |
| 8 | 1.58$^d$ | 36.4, CH | 1.85$^d$ | 36.2, CH |
| 9 | 1.00$^d$ | 54.4, CH | 1.42$^d$ | 46.1, CH$_2$ |
| 10 |   | 39.0, qC |   | 37.0, qC |
| 11 | 1.43$^d$ | 21.5, CH$_2$ | 1.43$^d$ | 20.6, CH$_2$ |
|   | 1.59$^d$ |   |   |   |
| 12 | 1.25 α,$^d$ | 38.9, CH$_2$ | 1.38 α,$^d$ | 34.9, CH$_2$ |
|   | 1.88 β,$^d$ |   | 2.40 β,$^d$ |   |
| 13 |   | 43.5, qC |   | 41.5, qC |
| 14 | 1.15$^d$ | 56.2, CH |   | 108.2, qC |
| 15 | 1.22$^d$ | 24.5, CH$_2$ | 4.02 a, dd (10.0, 4.4) | 74.3, CH$_2$ |
|   | 1.73$^d$ |   | 4.23 b, d (10.0) |   |
| 16 | 1.76$^d$ | 26.2, CH$_2$ | 4.56 t (4.5) | 80.9, CH |
|   | 1.80$^d$ |   |   |   |
| 17 | 2.10$^d$ | 56.3, CH | 2.60, dd (7.6, 4.4) | 54.6, CH |
| 18 | 0.62, s | 13.3, CH$_3$ | 1.08, s | 17.3, CH$_3$ |
| 19 | 1.18, s | 17.8, CH$_3$ | 0.97, s | 19.6, CH$_3$ |
| 20 |   | 149.4, qC | 4.49, ddd (7.6, 6.0, 1.5) | 76.3, CH |
| 21 | 4.80, brs | 110.1, CH$_2$ | 4.05 a, dd (12.4, 6.0) | 66.3, CH$_2$ |
|   | 4.89, br s |   | 3.79 b, dd (12.4, 1.3) |   |
| 22 | 2.06$^d$ | 38.0, CH$_2$ |   |   |
| 23 | 2.10$^d$ | 27.5, CH$_2$ |   |   |
| 24 | 5.11, br t (7.0) | 124.7, CH |   |   |
| 25 |   | 131.3, qC |   |   |

TABLE 4-continued

| | | | | |
|---|---|---|---|---|
| 26 | 1.61, s | 17.8, $CH_3$ | | |
| 27 | 1.69, s | 26.2, $CH_3$ | | |
| 1' | | | 4.84, dd (9.6, 2.0) | 98.8, CH |
| 2' | | | 1.73, m | 33.3, $CH_2$ |
| | | | 2.10, m | |
| 3' | | | 3.43, ddd (12.0, 5.0, 2.0) | 79.3, CH |
| 4' | | | 3.91, brs | 67.1, CH |
| 5' | | | 3.60, q (6.5) | 71.5, CH |
| 6' | | | 1.55, d (6.4) | 17.8, $CH_3$ |
| $OCH_3$-3' | | | 3.40, s | 55.4, $CH_3$ | a $^1$H NMR measured at 400 MHz, $^{13}$C NMR measured at 100 MHz; NMR data of 1 were obtained in $CDCl_3$, and those of 2 in pyridine-$d_5$; assignments based on HSQC and HMBC NMR spectra.
$^b$J values (Hz) are given in parentheses. Some geminal protons were indicated as α- or β-oriented based on a NOESY experiment.
$^c$Multiplicity obtained from the DEPT spectra.
$^d$For overlapped signals, only chemical shift values are given.

5. *Leishmania mexicana* Parasite Strain a. Promastigote Assay.

*Leishmania mexicana* (MNYC/BZ/62/M379) was maintained by serial passage of amastigotes inoculated subcutaneously into the shaven rumps of 129SvE mice and was obtained by in vitro culture of amastigotes in RPMI-1640 supplemented with 10% fetal calf serum (FCS, Sigma-Aldrich Corporation, St. Louis, Mo.) and incubated at 28° C. All work including experimental animals was approved by the Institutional Animal Care and Use Committee (IACUC) of The Ohio State University.

6. In Vitro Antilieshmanial Activity Studies a. Promastigote Assay.

One million log phase promastigotes of *L. mexicana* were seeded in 1 mL of complete RPMI-1640 medium, and parasite numbers, and their mobility and morphology were measured from 24 and 48 h. This was performed by flow cytometry measurements using experimental and control groups of parasites stained with propidium iodide and with *Quillaja saponaria* saponin as positive control, as reported in the literature. The test compounds isolated from *P. andrieuxii* were compared with a positive control: sodium stibogluconate, a pentavalent antimonial drug.

b. Amastigote Assay.

Bone marrow derived macrophages were obtained from C57BL/6 mice. Bone marrow-derived macrophages (BMDM) (0.5×10$^6$) were adhered on top of glass rounded coverslips deposited at the bottom of individual plate's well (24 well tissue culture plate, Corning, Inc.). Next, macrophages were infected overnight with 2.5×10$^6$ stationary phase promastigotes of the *L. mexicana* (ratio 5:1). After this period, cells were extensively washed with Hank's balanced salt solution (HBSS) to eliminate non-phagocytosed parasites, and, after treatment with test compounds for 48 hours, cells were stained with Giemsa stain (Sigma). In each experiment, infection rates were recorded by counting the number of parasites in 100 macrophages on each slide in triplicate in a blinded fashion.

7. Cytotoxicity Assay in Non-Infected Macrophages

Bone marrow derived-macrophages (0.5×10$^6$) from C57BL/6 mice were seeded into 24-well tissue culture plates (Corning, Inc.) and co-cultured (48 h) with a 100 µM concentration of each test compound, including non-treated sham controls. Cells were stained with trypan blue for viability determination (Ferreira et al., 2011). Viability of treated cells was similar to sham controls (more than 80%) in experiments ran in triplicate.

8. In Vitro Assay and Cell Sample Preparation for Electron Microscopy (EM)

Intracellular parasites were co-cultured, as previously described herein, by treating a 100 µM concentration of each pure compound for 2 h and suspending them in glutaraldehyde. Samples were further processed in an electron microscopy unit as follows: Incubation steps were carried out on a Lab-Line orbital shaker operating at 700 rpm (Barnstead/Thermolyne, Melrose Park, Ill.). After the initial fixation in 3% buffered glutaraldehyde, cell pellets were washed twice with sodium cacodylate buffer (pH 7.4, 10 minutes each) and spun down after each wash at 1500 rpm for 5 min. Cell samples were then post-fixed in 1% osmium tetroxide in sym-collidine buffer (pH 7.6) for 1 h at room temperature. Following two washes with sym-collidine buffer (10 min each) the cell pellet was stained with a saturated aqueous uranyl acetate solution (pH 3.3) for 1 h. Cell pellets were dehydrated in a graded EtOH series up to absolute (10 min each). Acetone was used as the transitional solvent, two changes for 10 min each. The cell suspensions were infiltrated overnight with a 1:1 mixture of acetone and Spurr's epoxy resin (Electron Microscopy Sciences, Fort Washington, Pa.). Finally, cell pellets were placed into BEEM™ embedding capsules containing 100% Spurr's resin. Polymerization of epoxy blocks was carried out at 70° C. overnight. Polymerized blocks were sectioned with a Leica Ultraut UCT ultramicrotome (Leica Microsystem GmbH, Wein, Austria). Methylene Blue-Basic Fuschin stained semithin (750 nm) sections were evaluated and two representative areas were thin-sectioned for ultrastructural examination. Ultrathin (80 nm) sections were collected on 200 mesh copper grids (Electron Microscopy Sciences) and post-stained with lead citrate (3 min).

9. In Vitro Activity of Compounds

Figure 5:
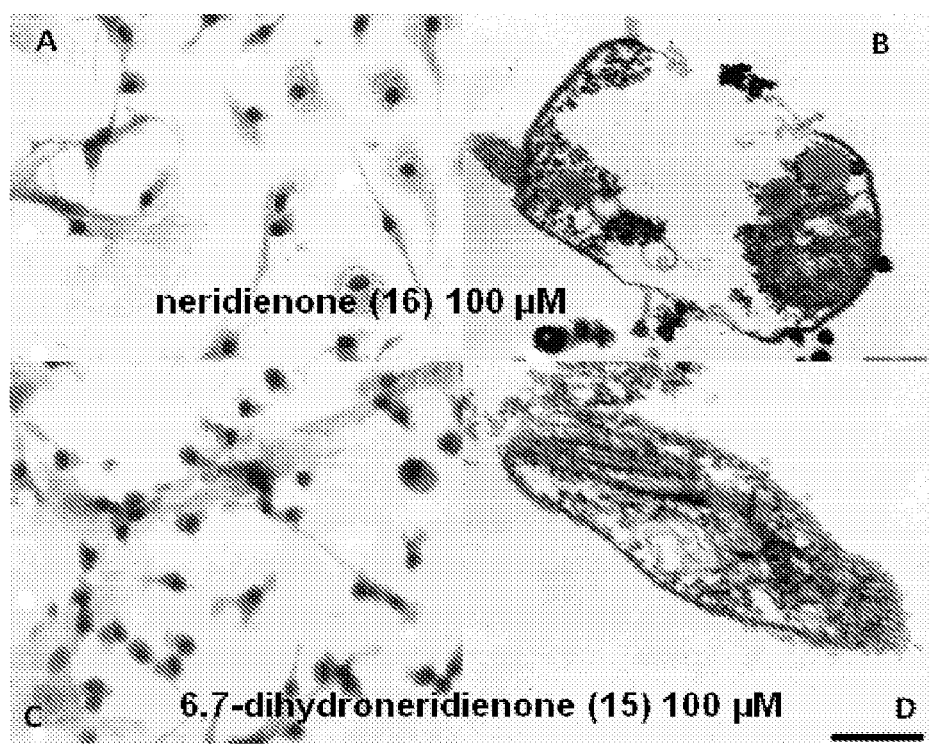
FIG. 5 shows representative data pertaining to in vitro antileishmanial activities of representative isolated *P. andrieuxii* compounds.
Figure 6:
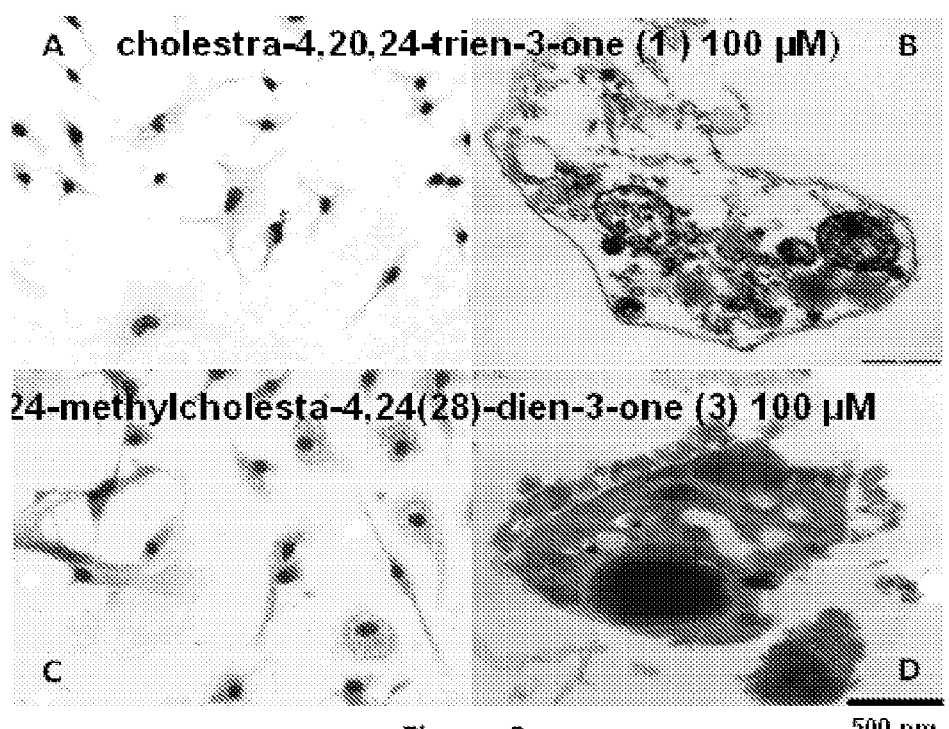
FIG. 6 shows representative data pertaining to in vitro antileishmanial activities of the isolated *P. andrieuxii* compounds.
Figure 7:
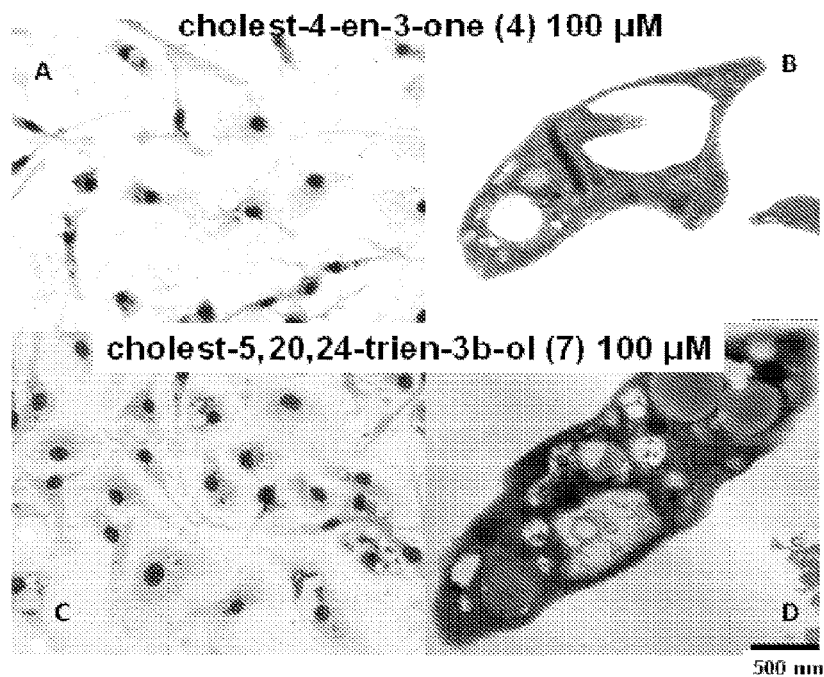
FIG. 7 shows representative data pertaining to in vitro antileishmanial activities of the isolated *P. andrieuxii* compounds.
Figure 8:
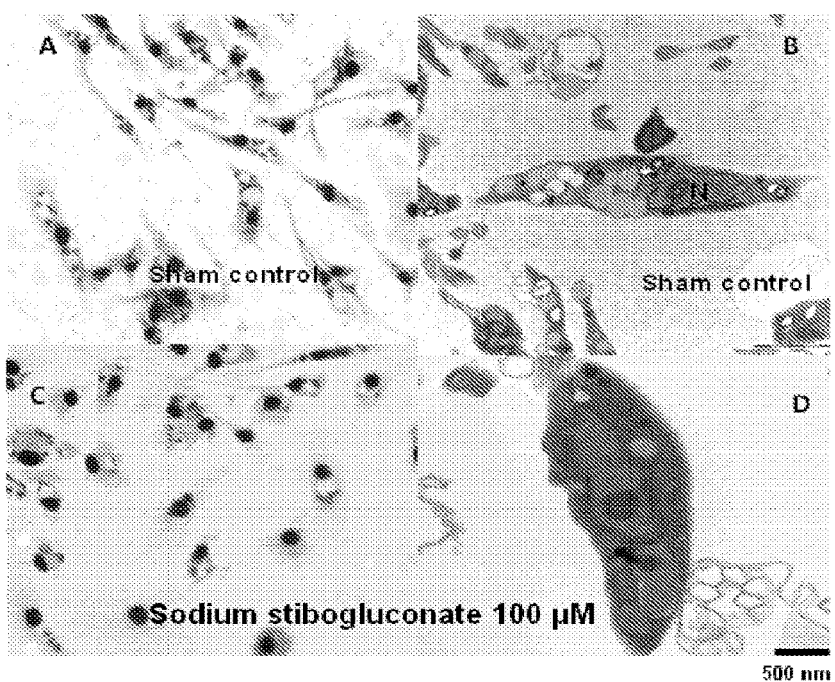
FIG. 8 shows representative data pertaining to in vitro antileishmanial activities of the isolated *P. andrieuxii* compounds.

All the isolated compounds (1-20) from the roots of *P. antrieuxii* were evaluated for their antileishmanial activity on both the promastigote and amastigote stages of *L. mexicana*. After 48 h of exposure against *L. mexicana* promastigotes, five sterols (1, 3, 4, 15, and 16) were found to show inhibitory effects and were more active than that observed for the reference compound, pentostam. Of these compounds, 6,7-dihydroneridienone (15) (FIG. 5, panel D) was the most potent principle, with an $IC_{50}$ value of 9.2 µM. The novel cholesterol analogue, cholest-4,20,24-trien-3-one (pantalinonsterol, 1) (FIG. 6, panel B) together with three additional sterols, cholest-4-en-3-one (4) (FIG. 7, panel B), 24-methylcholest-4,24(28)-dien-3-one (3) (FIG. 6, panel D) and neridienone (16) (FIG. 5, panel B), exhibited antileishmanial activity against promastigotes of *L. mexicana*. The sham control and pentosam positive control are shown in FIG. 8, panel B and D, respectively.

All five compounds with leishmanicidal activity against *L. mexicana* promastigotes, together with compound 7, which was considered inactive in the extracellular stage (FIG. 7, panel D), were observed to show significant activity against the amastigote stage. Among these compounds, 1 (FIG. 6, panel A), 3 (FIG. 6, panel C), 15 (FIG. 5, panel C), and 16 (FIG. 5, panel A), gave $IC_{50}$ values of 3.3, 3.5, 1.4 and 3.5 μM, respectively, and exhibited comparable potency to the positive control, pentostam ($IC_{50}$ 2.7 μM). Compound 7 (FIG. 7, panel C) was observed to be less active than pentostam (FIG. 8, panel C), with an $IC_{50}$ value of 14.5 μM. Compound 4 (FIG. 7, panel A) showed the most potent leishmanicidal activity on this intracellular stage, with an $IC_{50}$ value of 0.03 μM, nearly 100 times more potent than pentostam.

With the exception of compound 7, all the other active sterols with leishmanicidal activity in the present study were observed to share a common 4-ene-3-oxo functionality in the steroidal ring system, while most of sterols (8-14) with a 3-ol-5-ene moiety, no obvious antileishmanial activity was observed. Without wishing to be bound by a particular theory, it is believed that variation of the side chain on the five-membered D ring of these 4-ene-3-oxo sterols also influenced the resultant activity. Thus, compounds 5 and 6, two stigmasterol derivatives with an extra ethyl group at C-24 of the side chain when compared with the active cholesterol derivatives 1 and 4, were both inactive in the bioassays used. The novel compound, pentalinosterol (1), with double bonds at C-20 and C-24, was observed to be almost three times more active in the promastigote bioassay than cholest-4-en-3-one (4), for which the side chain is saturated. None of the 3-ol-5-ene sterols was found active in the promastigote assay. Compound 7, the only agent isolated with a 3-ol-5-ene functionality active in the amastigote assay, possesses the same side chain on the D ring as that in compound 1. For the two active $C_{21}$ sterols, 6,7-dihydroneridienone (15) and neridienone (16), both have an acetyl group on the D ring instead of a long alkyl chain that occurs in other active compounds. Compound 15 was observed to be more active than 16 in both the promastigote and amastigote bioassay, with the latter possessing an extra double bond at C-5 in the B ring.

The in vitro antileishmanial activities of the active compounds isolated from the roots of *Pentalinon andrieuxiia* were compared to sodium stibogluconate (Table 5). Compounds with $IC_{50} \geq 100$ μg/mL are not shown in the table below and the compound number corresponds to the numbering used in Table 2 above. The $IC_{50}$ values (μM) were calculated by linear regression analysis from the $K_C$ values at the concentrations used (1, 10, 50 and 100 μg/mL) at 48 hours in culture.

TABLE 5

| Compound | Promastigote $IC_{50}$ (μM) | Amastigote $IC_{50}$ (μM) |
| --- | --- | --- |
| 1 | 30.0 | 3.3 |
| 3 | 24.0 | 3.5 |
| 4 | 81.0 | 0.03 |
| 7 | >262 | 14.5 |
| 15 | 26.2 | 3.5 |
| 16 | 9.2 | 1.4 |
| Sodium stibogluconate | 346.1 | 2.7 |

Figure 9:
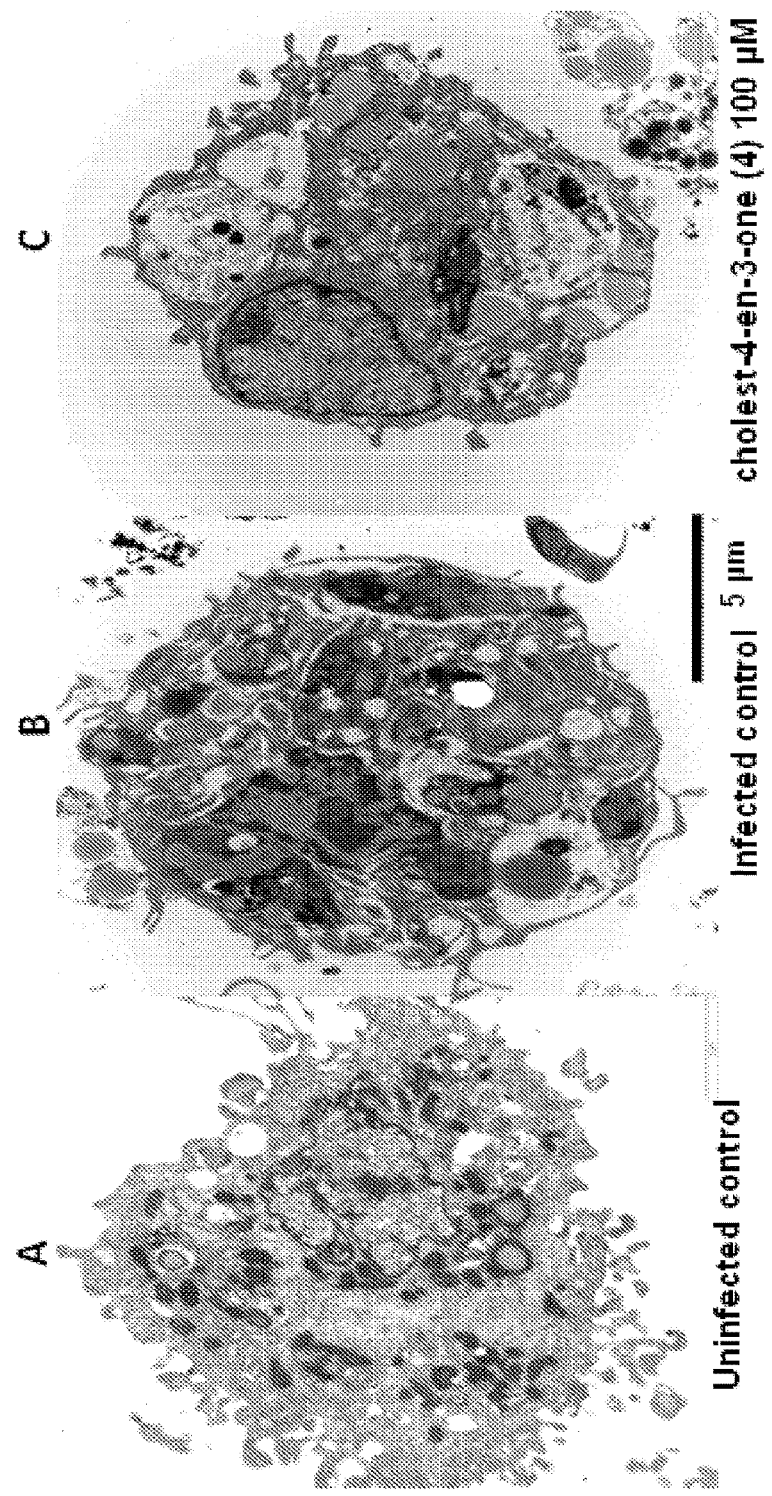
FIG. 9 shows representative data pertaining to in vitro antileishmanial activities of the isolated *P. andrieuxii* compounds.

All the isolates were also evaluated for cytotoxicity in non-infected bone marrow derived macrophages (FIG. 9, panel A) from C57BL16 mice, the host cells. None of the compounds were found active in this bioassay ($IC_{50}$>100 μg/mL), suggesting the compounds of the present invention are selective for the protozoal cell.

Figure 10:
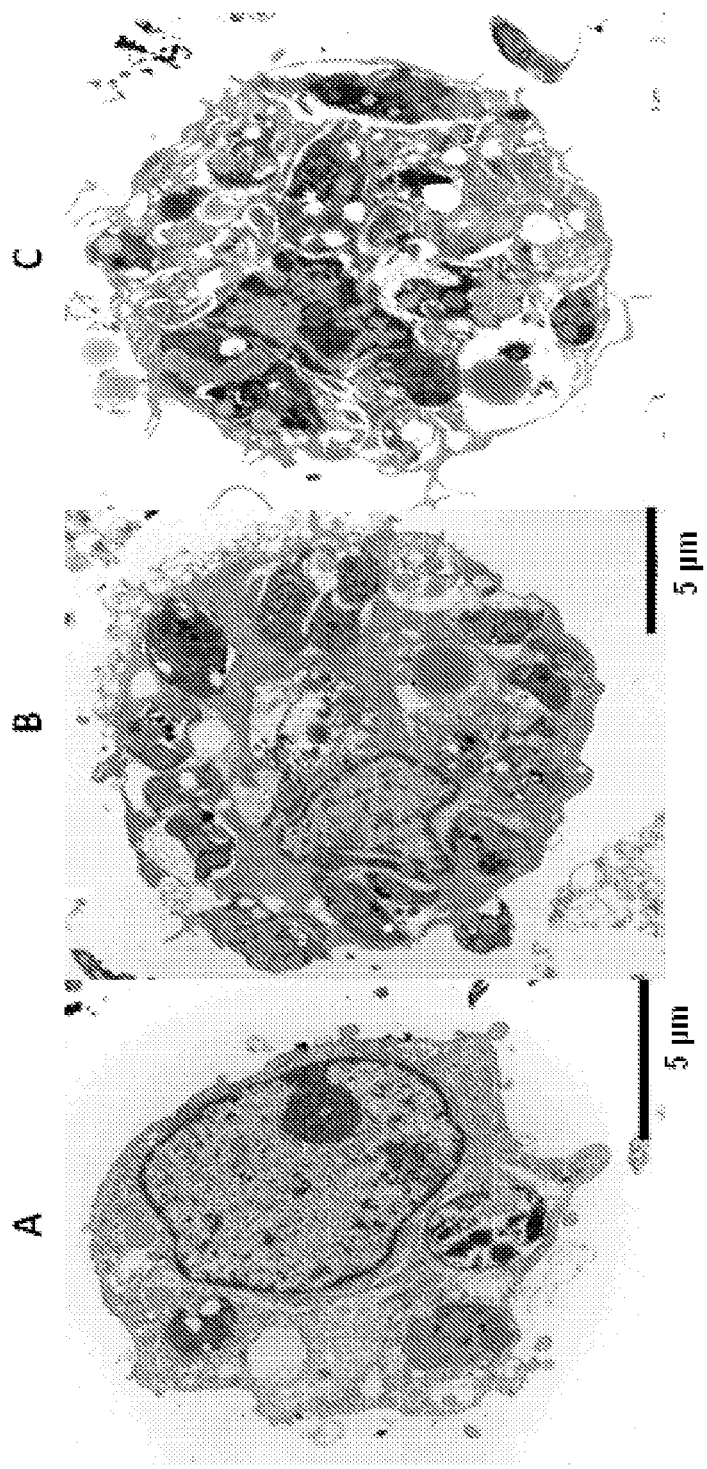
FIG. 10 shows representative data pertaining to in vitro antileishmanial activities of the isolated *P. andrieuxii* compounds.
Figure 11:
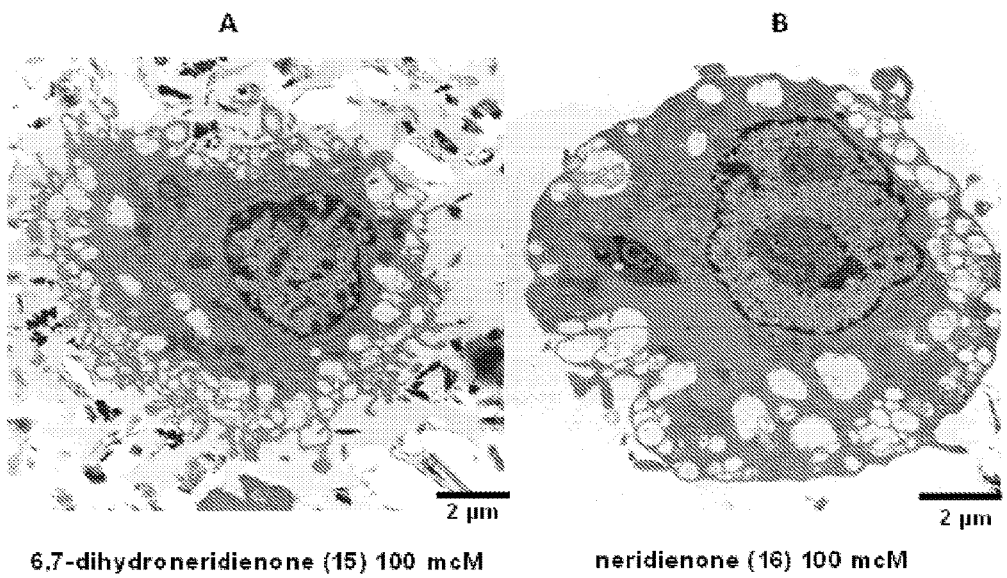
FIG. 11 shows representative data pertaining to in vitro antileishmanial activities of the isolated *P. andrieuxii* compounds.
Figure 12:
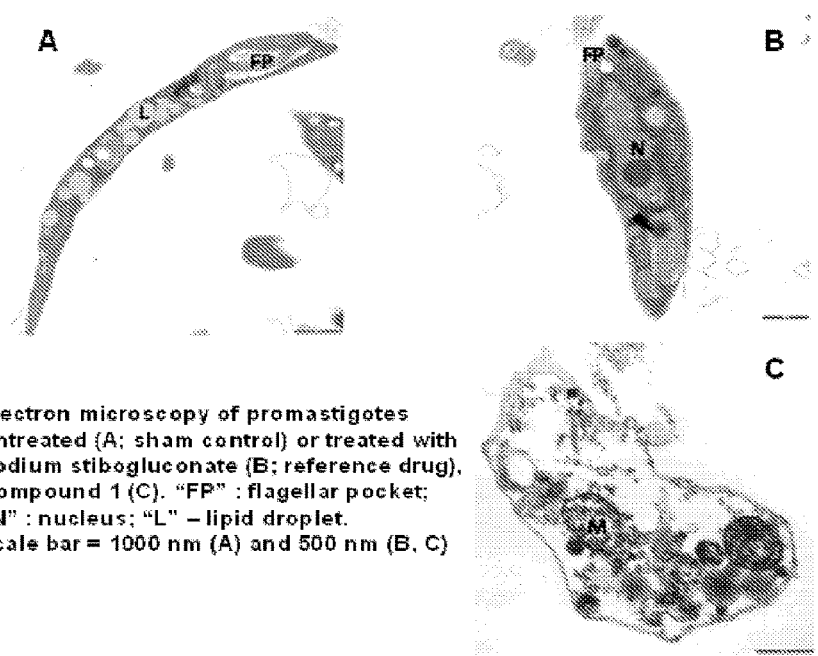
FIG. 12 shows representative data pertaining to in vitro antileishmanial activities of the isolated *P. andrieuxii* compounds.

Intracellular parasites treated with compounds 1, 3 (FIG. 10, panel A), 4 (FIG. 10, panel C), 15 (FIG. 7, panel C), and 16 were further studied by electron microscopy. The intracellular parasites were treated for 2 h at a 100 μM concentration of the individual bioactive molecules (compounds 1, 3, 4, 15, and 16). Electron microscopy shows morphological abnormalities (FIG. 12, panel C) and destruction as compared to sham control (FIG. 12, panel A) or reference drug-treated parasites (100 μM) (FIG. 12, panel C). Membrane alterations in the parasites were observed after treating the organisms with the active sterols. Without wishing to be bound by a particular theory, the morphological changes seen in the EM images suggests the active sterols can replace cholesterol during the membrane biosynthesis of the parasites and induce membrane instability and disruption.

10. Preparation of Liposomes for Use in In Vivo Studies

Liposomes were made by rehydration of a lipid cake. First, hydrogenated soy phosphatidylcholine (Avanti Polar Lipids, Inc., Alabaster, Ala.), cholesterol (Avanti Polar Lipids), 1,2-distearoyl-sn-glycero-3-[phospho-rac-(1-glycerol)] ("DSPG"; Avanti Polar Lipids,), and α-tocopherol (Sigma-Aldrich Corporation, St. Louis, Mo.) were dissolved in a chloroform and methanol (9:1, v/v). Compound 1 was dissolved in the lipid solution at a weight ratio of compound 1 to lipid of 1:9 (i.e. for clarity, the solution comprised 10% by weight of compound 1 and 90% by weight of the lipid solution). The solution was placed on at rotary evaporator for about 30 minutes and the liquid was completely evaporated. The lipids were reconstituted into liposomes in deionized water (3 mL) for 30 minutes in a 60° C. water bath, followed by 3 freeze-thaw cycles. The liposomes were extruded through an 80 nm polycarbonate filter (Avanti Polar Lipids). The extrusion step was repeated about 10-11 times. Liposomes containing compound 1 were passed over a PD-10 column (GE Healthcare, USA) with a deionized water mobile phase in order to remove any unencapsulated drug. Sucrose (300% of lipid weight) was added to the liposomes and the liposome-sucrose solution was lyophilized. Loading of liposomes was verified and quantified by HPLC.

11. In Vivo Activity of *Pentalinon andrieuxii* Root Extract and an Isolated Compound a. Antileishmanial Activity of a *Pentalinon andrieuxii* root Extract in *L. mexicana*.

Figure 13:
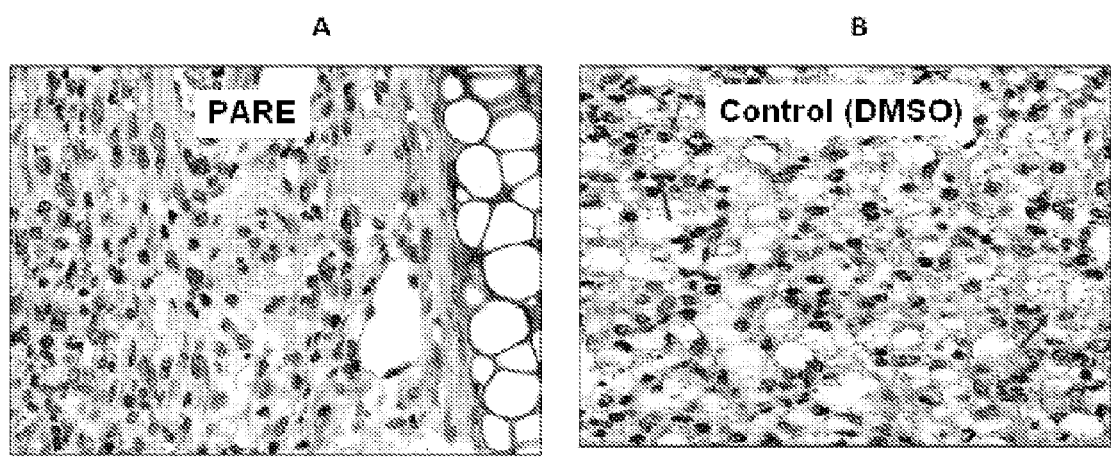
FIG. 13 shows data pertaining to in vivo antileishmanial activities of the *P. andrieuxii* root extracts.

A preliminary in vivo experiment with *Pentalinon andrieuxii* root extract (PARE), was performed to evaluate potential topical leishmanicidal activity. 10 week old male C57BL/6 mice were infected with *L. mexicana* promastigotes in the ear dermis. Following inoculation with *L. mexicana* promastigotes, the infected ear was treated topically once daily for 21 days with either drug (10 μg of PARE dissolved in 50 μl of DMSO/PBS) or control (DMSO). Lymphocytes and macrophages (white cells) from mice treated with PARE (FIG. 13, panel A) did not show the presence of parasites. In contrast, the lymphocytes and macrophages (white cells) from mice treated with control showed the intracellular presence of parasite (FIG. 13, Panel B). In conjunction with the overall bioassay testing results observed in this disclosure, this data suggest that PARE, and its sterol constituents, have leishmanicidal activity.

b. Antilieshmanial Activity of Liposomal Preparation of Compound 1 on *L. donovani*

In vivo studies were carried out with a liposomal formulation of compound 1 in order to evaluate parenteral leishmanicidal activity. Briefly, 8-10 week old *Leishmania*-susceptible BALB/c mice were injected with $2 \times 10^7$ *Leishmania donovani* (Strain LV9) amastigotes via the tail vein. The injection volume was 100 µL. Two weeks after infection, the mice were administered a liposomal preparation of compound 1 via injection of the tail vein. The liposomal preparation used in these studies was prepared as described above. Dose groups (n=3) were administered 100 µL of a liposomal suspension with or without compound. The liposomal preparation with compound (100 µL; 3.525 mg liposome preparation) comprised 415.53 µg lipids, 46.1 µg compound 1, and 3063.3 µg sucrose; the liposomal preparation without compound (100 µL; 3.525 mg liposome preparation) comprised 461.7 µg lipids and 3063.3 µg sucrose.

Figure 14:
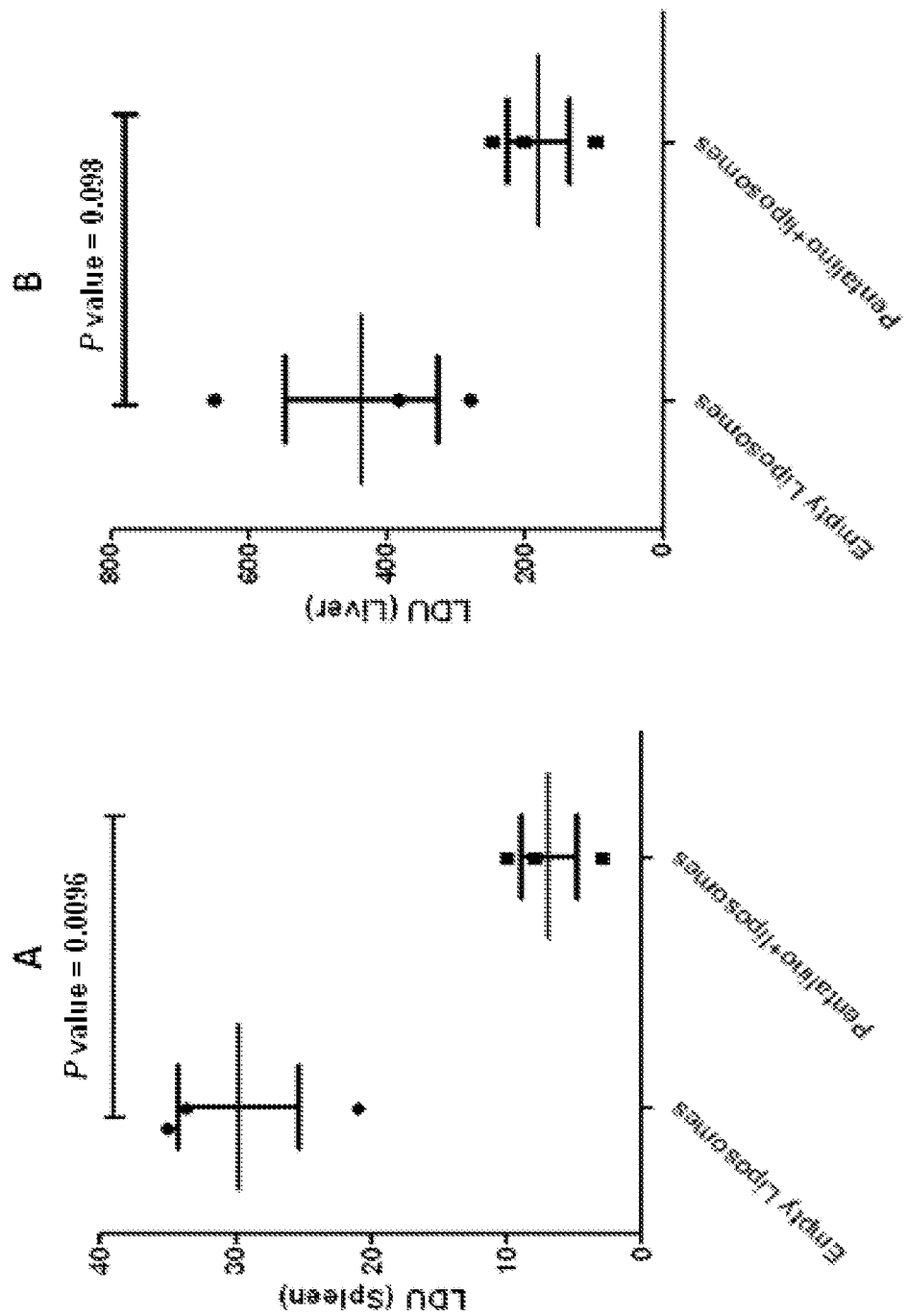
FIG. 14 shows representative data pertaining to in vivo antileishmanial activities of a liposomal formulation of compound 2.

One week after the treatment, the mice were euthanized and parasite loads in the liver and spleen were determined. Parasite loads in the spleen and liver were quantified as previously described (Murray, H. W. 2000. *Infect Immun.* 68: 6294-6299). Briefly, the liver and spleen impression smears were stained using Giemsa and parasite loads we quantified microscopically. LDU is determined by the number of amastigotes per 1000 nuclei multiplied by the weight (gm) of the liver or spleen. At this time, spleen cell suspensions were prepared and these cells were stimulated in vitro with 20 microgram/ml of *Leishmania donovani* antigen for 48-72 hrs to stimulate lymphocyte release. Proliferation of spleen cells were determined by Alamar blue assays and levels of cytokines including IFN-gamma in supernatant were quantified by ELISA using commercially available reagents from Biolegend and BD Biosciences. The parasite load detected in splenic cells (FIG. 14, panel A) and hepatic cells (FIG. 14, panel B) samples taken from the drug-treated mice showed a decreased parasite load, suggesting that compound 1 has leishmanicidal activity in vivo.

T cell proliferation was determined as previously described (Rosas, L. E., et al., 2006. *Am. J. Pathol.* 168: 158-169.). Briefly, $5 \times 10^5$ cells were added in quadruplicate to the wells of sterile 96-well, flat-bottom tissue culture plates and stimulated with freeze-thawed *L. donovani* Ag (20 µg/ml). The proliferation responses were measured by Alamar blue assay (Ansar-Ahmed, A., et al., 1994. *J. Immunol. Methods* 170: 211-214.). Supernatants were collected after 72 hours of incubation at 37° C. and analyzed for the production of IFN-γ and IL-10 by standard ELISA methods (BD Pharmingen, Inc., San Diego, Calif.).

Figure 15:
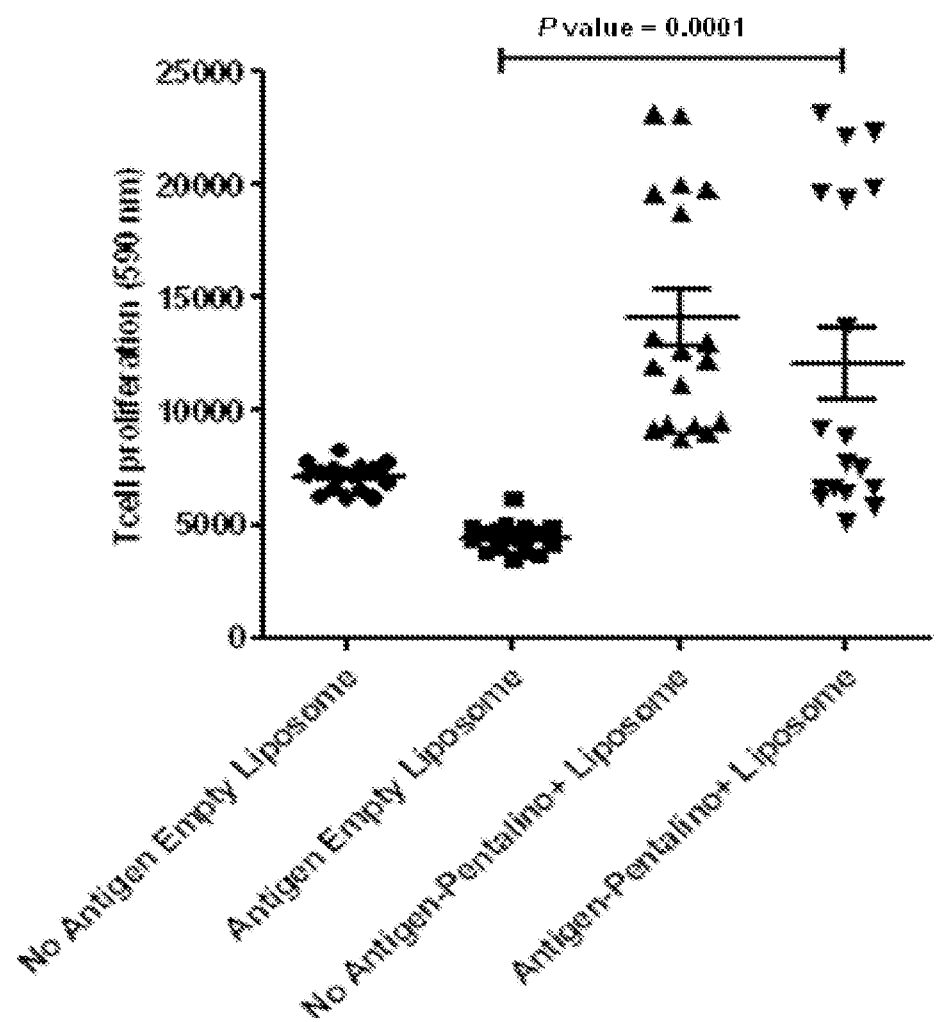
FIG. 15 shows representative data pertaining to the effect of a liposomal formulation of compound 2 on T-cell proliferation in an animal model of Leishmaniasis.
Figure 16:
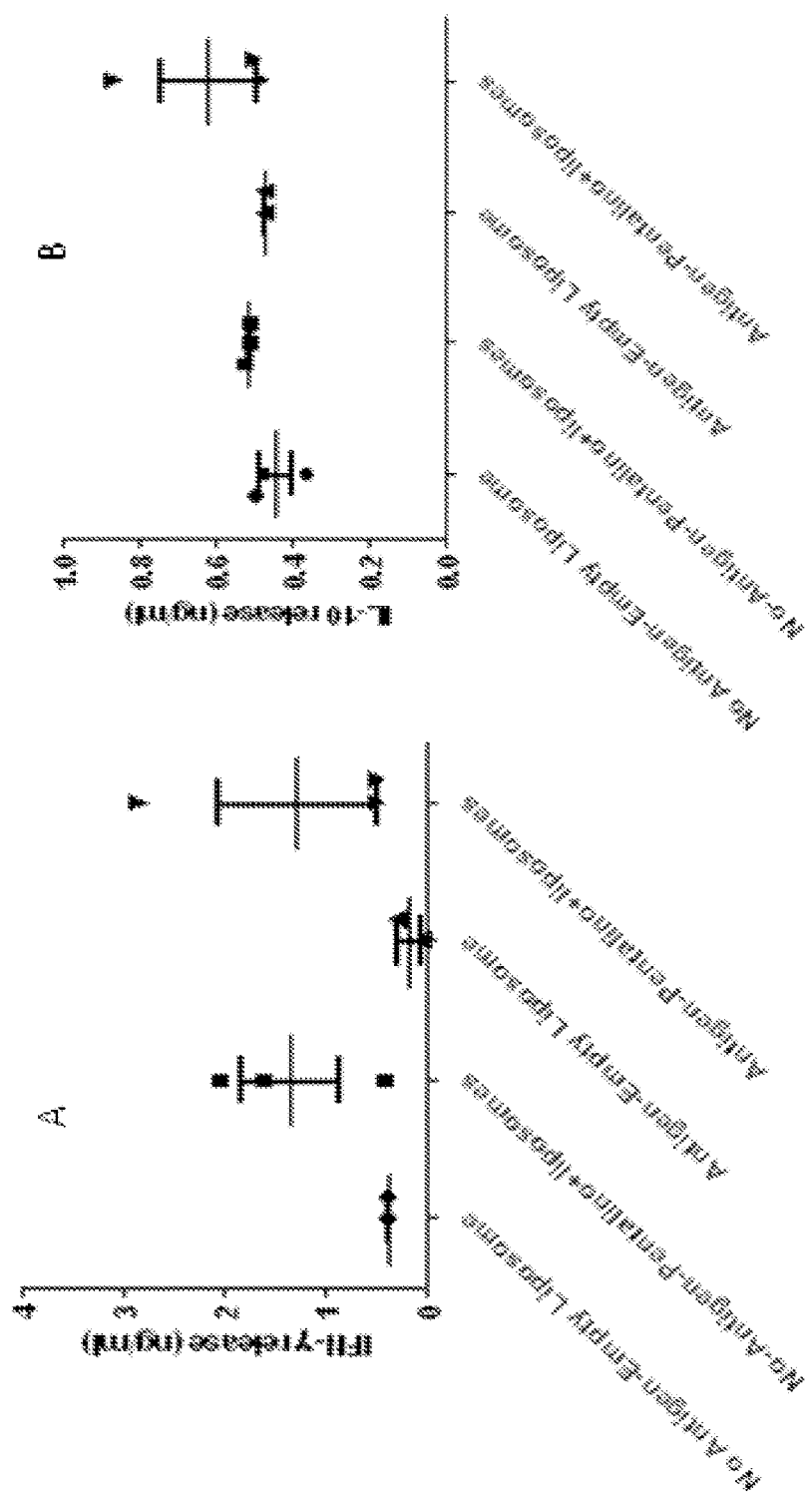
FIG. 16 shows representative data pertaining the effect of a liposomal formulation of compound 2 on cytokine release in an animal model of Leishmaniasis.

The data (FIG. 15) show that splenocytes from animals that were treated with compound 1 had a significant increase (P value<0.0001) in T cell proliferation upon stimulation with Leishmanial antigen compared to a parallel group that did not receive compound 1. The data show that splenocytes from animals that were treated with compound 1 had a significant increase (P value<0.01) in the secretion of IFN-γ upon with Leishmanial antigen stimulation (FIG. 16, panel A), whereas there was no significant change in the levels of IL-10 secreted from the same splenocyte samples (FIG. 16, panel B). Without wishing to be bound by a particular theory, increased levels of IFN-gamma and T-cell proliferation are believed to be a critical hallmarks for an effective protective immunity response to VL.

12. Prophetic Pharmaceutical Composition Examples

"Active ingredient" as used throughout these examples relates to one or more disclosed compounds, a product of a disclosed method of making, or a pharmaceutically acceptable salt, solvate, polymorph, hydrate or stereochemically isomeric form thereof. The following examples of the formulation of the compounds of the present invention in tablets and injectable formulations are prophetic. Typical examples of recipes for the formulations of the invention are as given below.

In the examples below, active ingredient can be replaced with the same amount of any of the compounds according to the present invention, in particular by the same amount of any of the exemplified compounds.

The amount of a disclosed compound in a pharmaceutical composition in terms of dosage unit, e.g. an ampule for single use administration or a table, for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per dosage unit.

a. Pharmaceutical Composition for Oral Administration

A tablet can be prepared as follows:

| Component | Amount |
| --- | --- |
| Active ingredient | 10 to 500 mg |
| Lactose | 100 mg |
| Crystalline cellulose | 60 mg |
| Magnesium stearate | 5 |
| Starch (e.g. potato starch) | Amount necessary to yield total weight indicated below |
| Total (per capsule) | 1000 mg |

Alternatively, about 100 mg of a disclosed compound, 50 mg of lactose (monohydrate), 50 mg of maize starch (native), 10 mg of polyvinylpyrrolidone (PVP 25) (e.g. from BASF, Ludwigshafen, Germany) and 2 mg of magnesium stearate are used per tablet. The mixture of active component, lactose and starch is granulated with a 5% solution (m/m) of the PVP in water. After drying, the granules are mixed with magnesium stearate for 5 min. This mixture is moulded using a customary tablet press (e.g. tablet format: diameter 8 mm, curvature radius 12 mm). The moulding force applied is typically about 15 kN.

Alternatively, a disclosed compound can be administered in a suspension formulated for oral use. For example, about 100-5000 mg of the desired disclosed compound, 1000 mg of ethanol (96%), 400 mg of xanthan gum, and 99 g of water are combined with stirring. A single dose of about 10-500 mg of the desired disclosed compound according can be provided by 10 ml of oral suspension.

In these Examples, active ingredient can be replaced with the same amount of any of the compounds according to the present invention, in particular by the same amount of any of the exemplified compounds. In some circumstances it may be desirable to use a capsule, e.g. a filled gelatin capsule, instead of a tablet form. The choice of tablet or capsule will depend, in part, upon physicochemical characteristics of the particular disclosed compound used.

Examples of alternative useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. These alternative carriers can be substituted for those given above as required for desired dissolution, absorption, and manufacturing characteristics.

The amount of a disclosed compound per tablet for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

b. Pharmaceutical Composition for Injectable Use: Pegylated Liposomes.

The compounds of the present invention can be used to produce pegylated liposomal formulations. Pegylated liposomes can be made using lipids that are covalently attached to polyethylene glycol (PEG). The size (or molecular weight) of the PEG chains can be varied to optimize the desired pharmacokinetic properties. By adding these lipids in small percentages to existing formulations, the circulation half life of the drug can be enhanced. Without wishing to be bound by a particular theory, this formulation can potentially allow for increased duration in blood circulation, and can allow potentially better penetration into the bone marrow for increased efficacy.

Liposomes are prepared by a simple film hydration method. For example, required quantities of soyaphosphotidylcholine, cholesterol (1:1, 2:1), MPEG 2000-DSPE (5 mol %)[14] and a disclosed compound, e.g. compound 1, (0.2 mg/ml) in appropriate molar ratios are dissolved in chloroform. Glass beads (10 g) are added to increase surface area available for film formation. Chloroform is evaporated under reduced pressure on a rotary evaporator to form a thin film on the inner surface of the flask. Lipid film is hydrated using above gel to liquid crystalline phase transition temperature (65°) of the lipids and cholesterol for two minutes and flask manually shaken vigorously for 5 min for formation of liposomes followed by heating it again for 2 min for annealing of liposomes. The dispersion is sonicated using bath sonicator for 15 or 45 s to get the liposomes of smaller size.

c. Pharmaceutical Composition for Injectable Use: Nanoparticles and Microparticles.

The compounds of the present invention can be used to produce nanoparticles and microparticles. Nanoparticles and microparticles can be made using hydrophobic degradable polymers to encapsulate hydrophobic drugs, such as pentalinosterol. By using emulsion processes, a disclosed compound, e.g. compound 1, can be incorporated into the polymeric matrix. Additionally, PEG can be incorporated into these particles to increase the circulation half life.

Microparticles containing pentalinosterol are prepared using an oil-in-water emulsion method. For example, a disclosed compound, e.g. compound 1, is dissolved in chloroform, and this solution is then used to dissolve (polylactide acid) PLA (100 mg). The resulting solution is added to an aqueous solution (2 mL, 3% w/w in PBS) of poly(vinyl alcohol) ("PVA," e.g. MW=13,000-23,000 g/mol, 87-89% hydrolyzed) and sonicated for 30 seconds on ice using a probe sonicator (Branson Sonifier 450, with a 0.5 in. flat tip) with an output setting of 3 and a duty cycle of 10%. The resulting single emulsion is immediately poured into a second PVA solution (10 ml, 0.3% w/w in PBS) and stirred for 4 hours to allow the organic solvent to evaporate. The particles are isolated by centrifugation (14,800×g, 15 min, 4° C.) and washed with $H_2O$ (e.g. double-distilled). The washed particles are re-suspended in $H_2O$ (2 mL, pH 9) and lyophilized.

In a further example, calculated amounts of poly(lactic-co-glycolic acid) (PLGA) and pentalinosterol are dissolved in acetone and injected in DSPEmPEG2000 emulsifier dissolved in water or PBS followed by immediate rigorous emulsification by a high power sonicator. This result in the synthesis of PEGylated nanoparticles (PNPs) of PLGA dispersed in the aqueous solution, with pentalinosterol entrapped in the hydrophobic PLGA matrix. The acetone can be removed acetone by rotary vacuum evaporation and purified drug-loaded nanoparticles by ultracentrifugation followed by rigorous washing (3×) with water or PBS and resuspension in PBS.

d. Pharmaceutical Composition for Injectable Use: Cyclodextrin Complexes

The compounds of the present invention can be used to produce cyclodextrin complexes. Cyclodextrins (CD) are capable of forming complexes with hydrophobic drugs and have been used for drug delivery. Depending on the size of the cyclodextrin (usually a six, seven or eight member ring) and the size of the hydrophobic drug, the complex will be formed. For example, a 1:1 or a 1:2 molar ratio of drug and CD is prepared by freeze drying an aqueous solution containing drug and various CDs (e.g. varying size and hydrophobicity characteristics). The solution is filtered, frozen and then freeze-dried at −52° C. for 48 h, thereby yielding a powder comprising the complex.

e. Pharmaceutical Composition for Injectable Use: Microemulsions and NanoEmulsions.

The compounds of the present invention can be used to produce microemulsion and nanoemulsions. Microemulsion droplets are composed of a lipid core comprising a mixture of oil (e.g., soybean oil) stabilized by a surfactant shell comprising a mixture of PEG-surfactants, and dispersed in an aqueous phase (e.g. saline). The microemulsion comprises the hydrophobic drug residing in the lipid core, and such emulsions can be readily used for the injection of the drug intravenously. Surfactants commonly used in this technique are Tween and Span. Nanoemulsions can be produced in a method similar to microemulsions, but high energy is required to decrease the size of the emulsion For example, a disclosed compound, e.g. compound 1 (30 mg), is dissolved in an oil such as castor oil (about 20 g). The resulting oil phase is mixed with polyethylene glycol (about 10.8 g), then mixed with Tween 80 (about 7.2 g), and water added so that it is about 60% by volume, and then the mixture is passed through high-pressure homogenizer.

Alternatively, a nanoemulsion can be prepared by mixing about 80 mg of drug with about 2.8 g of a solution of castor oil and middle-chain triglycerides (1:1, w/w), and then adding this mixture to about 200 ml of acetone and ethanol (1:1, v/v) containing about 2.0 g of soy lecithin. The oily phase is slowly added under magnetic stirring into about 400 ml of aqueous phase containing poloxamer 188 (about 600 mg) and glycerol (about 900 mg), thereby forming a nanoemulsion. Solvents and most water are removed under reduced pressure resulting in about 40 ml of a nanoemulsion formulation.

Alternatively, a nanoemulsion can also be prepared by dissolving a mixture of caprylic/capric triglyceride (70%), soya bean lecithin (27%), and cholesterol (3%) in chloroform-methanol (2:1, v/v). To this liquid mixture is added a disclosed compound (about 100 mg), e.g. compound 1. The mixture is dried under nitrogen flow and kept under vacuum overnight in order to remove organic solvent. Following removal of organic solvent, about 40 ml of tris(hydroxymethyl)aminomethane (TRIS)-HCl buffer (0.01 M, pH 8.05) is added and emulsified with a probe-type sonicator for 30 min at 50-60° C. The final dispersion is obtained after centrifugation at 150,000 g for 30 min to precipitate non-incorporated drug. The nanoemulsion is filtrated through a 0.22 µm membrane and stored at 4-25° C. protected from light.

f. Pharmaceutical Composition for Injectable Use: Polyersomes.

In various aspects, the compounds of the present invention can be used to produce polymersomes. Polymersomes are made from diblock or triblock co-polymers that form artificial vesicles. In general they are made in a method similar to that of liposomes described above.

g. Pharmaceutical Composition for Injectable Use: Micelles.

The compounds of the present invention can be used to produce micelles with the use of a surfactant wherein a disclosed compound is incorporated into the core of the micelles. Using the methods described herein, the micelle can self assemble and allow the drug to be solubilized by incorporation within the micelle.

A co-solvent evaporation method can be used for the self-assembly of MePEO-b-PCL block copolymers and drug encapsulation. "PEO" is polyethylene oxide and "PCL" is polycapralactone. The type of applied organic solvent, the ratio of organic to the aqueous phase, and the order of addition of the phases in the co-solvent evaporation method can be selected to optimize the micelle formed in terms of carrier size and encapsulation efficiency. For example, MePEO-b-PCL (about 30 mg) is dissolved in a suitable solvent such as acetone, tetrahydrofuran (THF) or acetonitrile. For this amount of MePEO-b-PCL, the volume of organic solvent can be either 0.5 or 1.5 mL, corresponding to a final 1:6 or 1:2 organic:aqueous phase ratio, respectively. The solution can be added drop-wise to water (3 mL), or alternatively water can be added drop-wise to this solution. The mixture is then stirred at room temperature for a suitable time, e.g. about 4 h. Vacuum is applied to remove the remainder of the organic solvent. Drug encapsulation is accomplished by dissolving about 3 mg of a disclosed compound, e.g. compound 1, in the organic solvent and following an identical procedure to the self-assembly condition. At the end of encapsulation process, the colloidal solution is centrifuged at 11,600×g for 5 min, to remove any precipitated disclosed compound.

h. Pharmaceutical Composition for Injectable Use: Suspensions.

In various aspects, the compounds of the present invention can be used to produce parenteral suspensions. In a preferred suspension formulation, insoluble particles should be uniformly dispersed and should redisperse uniformly in the continuous phase, upon moderate shaking, for a sufficient period of time. This allows the withdrawal of the correct amount of medication with minimal dose variation. The rate of settling can be decreased by using viscosity improving agents, and ease of redispersibility can be controlled by using flocculating agents. For example, surfactants can be used to stabilize the suspensions and serve as flocculating agents. However, there are only a limited numbers of nonionic and anionic surfactants that have been approved by regulatory agencies such as the FDA for use as excipients for parenteral use. Examples of approved excipients for parenteral use include phospholipids, polysorbate 80, and poloxamers.

For example, a parenteral suspension comprising a disclosed compound, e.g. compound 1, at a final concentration of about 50 mg/ml in sesame oil with about 20 mg/ml aluminum monostearate and 0.1% propylparaben.

Alternatively, a parenteral suspension comprising a disclosed compound, e.g. compound 1, at a final concentration of about 3 mg/ml in a physiological sodium phosphate solution (pH 6.8-7.2) with 0.1 mg/ml $Na_2$-EDTA and 0.2 mg/ml benzalkonium chloride.

Alternatively, a parenteral suspension comprising a disclosed compound, e.g. compound 1, at a final concentration of about 8 mg/ml in an aqueous solution comprising the following excepients: sodium carboxymethyl cellulose (CMC), 5 mg/ml; polysorbate 80, 0.75 mg/ml; sodium chloride, 6.7 mg/ml; creatinine, 5 mg/ml; sodium bisulfate, 1 mg/ml; and $Na_2$-EDTA, 0.5 mg/ml, pH 5-7.5.

i. Pharmaceutical Composition for Injectable Use: Solutions.

In various aspects, a biocompatible solution of a disclosed compound, e.g. compound 1, can be prepared using an organic solvent that is biocompatible. For example, propylene glycol, polyethylene glycols, ethanol), dimethyl sulfoxide, N-methyl-2-pyrrolidone, glycofurol, Solketal™, glycerol formal, acetone tetrahydrofurfuryl alcohol, diglyme, dimethyl isosorbide, cremophor, and ethyl lactate.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A pharmaceutical composition comprising a pharmaceutically acceptable carrier and a compound having the formula:

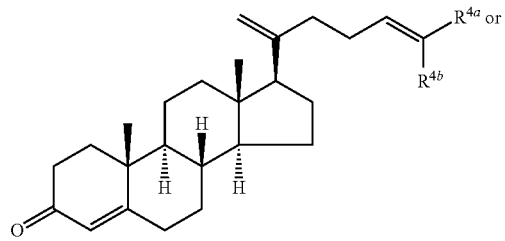

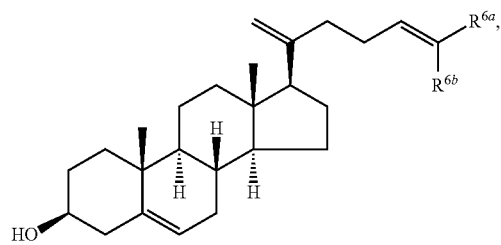

wherein each of $R^{4a}$ and $R^{4b}$ is independently selected from hydrogen and $C_1$-$C_{12}$ alkyl, and each of $R^{6a}$ and $R^{6b}$ is independently selected from hydrogen and $C_1$-$C_{12}$ alkyl;

or a pharmaceutically acceptable salt, solvate, or polymorph thereof;

wherein the pharmaceutically acceptable carrier is selected from the group consisting of a liposome, nanoparticle, microparticle, cyclodextrin, nanoemulsion, microemulsion, polymersome, surfactant, biocompatible organic solvent, and micelle, wherein the composition is sterile.

2. The composition of claim 1, wherein the compound is selected from:

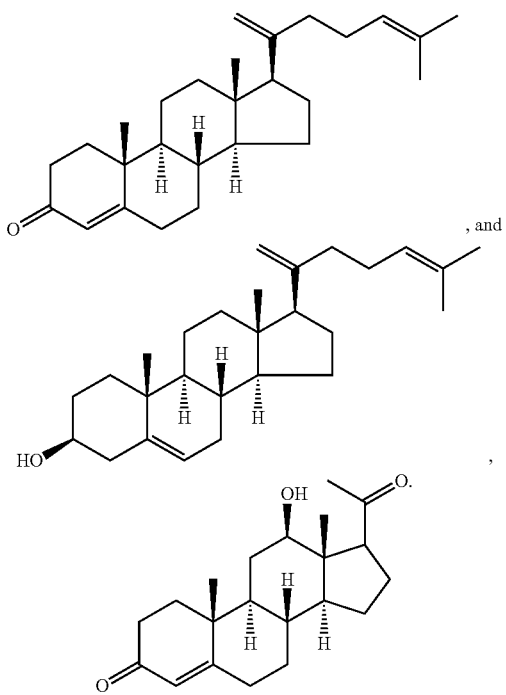

, and

3. The composition of claim 1, wherein the compound is:

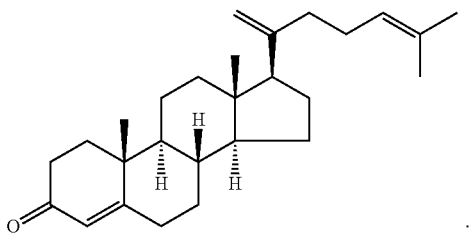

4. The composition of claim 1, wherein the pharmaceutically acceptable carrier is a liposome.

5. The composition of claim 4, wherein the liposome comprises a phospholipid.

6. The composition of claim 4, wherein the liposome comprises one or more lipids selected from phosphatidylcholine, tocopherol, cholesterol, and 1,2-distearoyl-phosphatidyl ethanolamine-methyl-polyethylene glycol conjugate.

7. The composition of claim 4, wherein the liposome comprises phosphatidylcholine and tocopherol.

8. The composition of claim 1, wherein the pharmaceutically acceptable carrier is a biocompatible organic solvent comprising propylene glycol, polyethylene glycol, ethanol, dimethyl sulfoxide, N-methyl-2-pyrrolidone, glycofurol, 2,2-dimethyl-1,3-dioxolane-4-methanol (Solketal™), glycerol formal, acetone tetrahydrofurfuryl alcohol, diglyme, dimethyl isosorbide, cremophor, or ethyl lactate.

9. The composition of claim 1, wherein the pharmaceutically acceptable carrier is a surfactant comprising a phospholipid, a poloxamer, or a polysorbate.

10. The composition of claim 1, wherein the composition is in the form of a powder, a granule, a solution, a suspension in an aqueous liquid, a non-aqueous liquid, an oil-in-water emulsion or a water-in-oil liquid emulsion.

11. The composition of claim 1, wherein the pharmaceutically acceptable carrier is a microemulsion or nanoemulsion.

12. The composition of claim 11, wherein the microemulsion or nanoemulsion comprises an oil, surfactant, and aqueous phase.

13. The composition of claim 12, wherein the oil comprises soybean oil or castor oil.

14. The composition of claim 12, wherein the surfactant comprises tween or span.

15. The composition of claim 1, further comprising at least one additional therapeutic agent.

16. The composition of claim 15, wherein the at least one additional therapeutic agent comprises a vaccine.

* * * * *

UNITED STATES PATENT AND TRADEMARK OFFICE
CERTIFICATE OF CORRECTION

PATENT NO. : 10,174,072 B2
APPLICATION NO. : 15/411249
DATED : January 8, 2019
INVENTOR(S) : Abhay R. Satoskar et al.

It is certified that error appears in the above-identified patent and that said Letters Patent is hereby corrected as shown below:

In the Claims

Claim 2, Column 99, Lines 1-30, should read as follows:
"The composition of claim 1, wherein the compound is selected from:

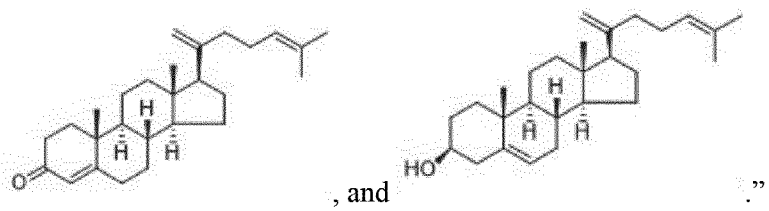

, and ."

Signed and Sealed this
Fourteenth Day of May, 2019

Andrei Iancu
*Director of the United States Patent and Trademark Office*

UNITED STATES PATENT AND TRADEMARK OFFICE
CERTIFICATE OF CORRECTION

| | | |
|---|---|---|
| PATENT NO. | : 10,174,072 B2 | Page 1 of 1 |
| APPLICATION NO. | : 15/411249 | |
| DATED | : January 8, 2019 | |
| INVENTOR(S) | : Abhay R. Satoskar et al. | |

It is certified that error appears in the above-identified patent and that said Letters Patent is hereby corrected as shown below:

In the Specification

Column 1, Lines 17-20 replace the Government Support Clause with:
--This invention was made with government support under grant numbers AI076309, AT004160, and AI090803 awarded by the National Institutes of Health. The government has certain rights in the invention.--

Signed and Sealed this
Thirteenth Day of October, 2020

Andrei Iancu
*Director of the United States Patent and Trademark Office*